United States Patent
Gielen-Haertwig et al.

(10) Patent No.: US 8,101,615 B2
(45) Date of Patent: *Jan. 24, 2012

(54) 1,4-DIARYL-DIHYDROPYRIMIDIN-2-ONES AND THEIR USE AS HUMAN NEUTROPHIL ELASTASE INHIBITORS

(75) Inventors: Heike Gielen-Haertwig, Monheim (DE); Barbara Albrecht, Wülfrath (DE); Jörg Keldenich, Wuppertal (DE); Volkhart Li, Velbert (DE); Josef Pernerstorfer, Hofheim (DE); Karl-Heinz Schlemmer, Wuppertal (DE); Leila Telan, Düsseldorf (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 719 days.

This patent is subject to a terminal disclaimer.

(21) Appl. No.: 10/590,770

(22) PCT Filed: Feb. 15, 2005

(86) PCT No.: PCT/EP2005/001486
§ 371 (c)(1),
(2), (4) Date: Jun. 18, 2007

(87) PCT Pub. No.: WO2005/082864
PCT Pub. Date: Sep. 9, 2005

(65) Prior Publication Data
US 2008/0064704 A1    Mar. 13, 2008

(30) Foreign Application Priority Data

Feb. 26, 2004  (EP) .................................... 04004314

(51) Int. Cl.
- *C07D 239/22* (2006.01)
- *C07D 401/06* (2006.01)
- *C07D 403/12* (2006.01)
- *A61K 31/506* (2006.01)

(52) U.S. Cl. ................... 514/252.14; 514/274; 544/295; 544/315

(58) Field of Classification Search ................. 544/295, 544/315; 514/252.14, 274
See application file for complete search history.

(56) References Cited

U.S. PATENT DOCUMENTS

| | | | |
|---|---|---|---|
| 5,532,366 A | 7/1996 | Edwards et al. | |
| 7,199,136 B2 | 4/2007 | Gielen-Haertwig et al. | |
| 7,687,510 B2 * | 3/2010 | Gielen-Haertwig et al. | 514/274 |
| 7,893,073 B2 | 2/2011 | Gielen-Haertwig et al. | |
| 2008/0045541 A1 | 2/2008 | Gielen-Haertwig et al. | |
| 2010/0184788 A1 | 7/2010 | Gielen-Haertwig et al. | |

FOREIGN PATENT DOCUMENTS

| | | |
|---|---|---|
| WO | 03/053930 | 7/2003 |
| WO | 2004/024700 | 3/2004 |
| WO | 2005037799 A1 | 4/2005 |
| WO | 2005082863 A2 | 9/2005 |

OTHER PUBLICATIONS

Ulrich, Chapter 4:Crystallization, Kirk-Othmer Encyclopedia of Chemical Technology, Aug. 2002.*
Vippagunta et al., Crystalline Solids, Advanced Drug Deliversy Reviews, 48, pp. 3-26, 2001.*
West, Solid Solutions, Solid State Chemistry and its applications, pp. 358 & 365, 1988.*
R.A. Stockley, Neutrophils and Protease/Antiprotease Imbalance, Am. J. Respir. Crit. Care Med., 160:549-552 (1999).
C.P. Tiefenbacher, et al., Inhibition of elastase improves myocardial function after repetitive ischaemia and myocardial infarction in the rat heart, Eur. J. Physiol., 433:563-570 (1997).
Dinerman, et al., Increased Neutrophil Elastase Release in Unstable Angina Pectoris and Acute Myocardial Infarction, J. Am. Coll. Cardiol., 15(7):1559-1563 (1990).
S.J. Gilbert et al., Increased expression of promatrix metalloproteinase-9 and neutrophil elastase in canine dilated cardiomyopathy, Cardiov. Res., 34:377-383 (1997).
Dollery, et al., Neutrophil Elastase in Human Atherosclerotic Plaques: Production by Macrophages, Circulation 107:2829-2836 (2003). Namazi, et al., Investigation the Chemical Reactivity of Positions N-3, C-5 and C 6 -Methyl Group in Biginelli Type Compounds and Synthesis of New Dihydropyrimidine Derivatives, J. Heterocyclic Chem., 38:1051-1054 (2001).
Ohmoto, et al., Development of Orally Active Nonpeptidic Inhibitors of Human Neutrophil Elastase; J. Med. Chem., 44, pp. 1268-1285 (2001).
Erian, et al., "A novel Synthesis of fused pyrazole systems as antimicrobial agents," Pharmazie, 53: 748-751 (1998).
Palomo et al. "Preparation of 3-Alkyl beta-Lactams via the Ketene-Imine Cycloaddition Reaction Using alpha-(Phenylthio)alkanoyl Halides as Starting Materials: Application to the Sysnthesis of (+/−)-Carbapenem Building Blocks and Related Compounds," J. Org. Chem. 56:4418-4428 (1991).

(Continued)

*Primary Examiner* — Deepak Rao
(74) *Attorney, Agent, or Firm* — Jonathan R. Harris; Thomas C. Blankinship; Karen B. King

(57) ABSTRACT

The invention relates to novel heterocyclic derivatives of the general formula (I), processes for their preparation, and their use in medicaments, especially for the treatment of chronic obstructive pulmonary diseases, acute coronary syndrome, acute myocardial infarction and heart failure development.

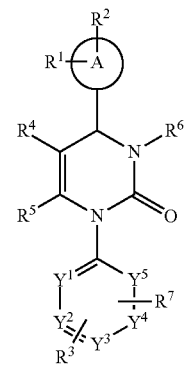

20 Claims, No Drawings

OTHER PUBLICATIONS

Walker et al. "Strategies for the Inhibition of Serine Proteases," CMLS, Cell. Mol. Life Sci. 58: 596-624 (2001).

Abbenante et al. "Protease Inhibitors in the Clinic," Medicinal Chemistry, 1:71-104 (2005).

Chughtai et al. "Potential Role of Inhibitors of Neutrophil Elastase in Treateing Diseases of the Airway," Journal of Aerosol Medicine, 17(4): 289-298 (2004).

Lewandowski, et al., "A combinatorial approach to recognition of chirality: preparation of highly enantioselective aryl-dihydropyrimidine selectors for chiral HPLC," J. Comb. Chem., 1:105-112 (1999).

Roghanian, et al., "Inflammatory Lung Secretions Inhibit Dendritic Cell Maturation and Function via Neutrophil Elastase," Am. J. of Respiratory and Critical Care Medicine, 174:1189-1109 (2006).

Hsieh, et al., "The evaluation and structure-activity relationships of 2-benzolaminobenzoic esters and their analogues as anti-inflammatory and anti-platelet aggregation agents," Bioorganic & Med. Chem. Lett., 17:1812-1817 (2007).

Kyne, et al., "The evaluation of structure-activity relationships of 2-benzoylamino benzoic esters and their analogues as anti-inflammatory and anti-platelet aggregation agents," Am. Heart J., 139(1): 94-100, (2000).

Pending U.S. Appl. No. 12/633,723, filed Dec. 8, 2009. Published as US2010-0814788, cited above.

Pending U.S. Appl. No. 10/589,907, filed Feb. 21, 2008. Published as US2008-0045541, cited above.

* cited by examiner

1,4-DIARYL-DIHYDROPYRIMIDIN-2-ONES AND THEIR USE AS HUMAN NEUTROPHIL ELASTASE INHIBITORS

The present invention relates to novel heterocyclic derivatives, processes for their preparation, and their use in medicaments, especially for the treatment of chronic obstructive pulmonary diseases, acute coronary syndrome, acute myocardial infarction and heart failure development.

The fibrous protein elastin, which comprises an appreciable percentage of all protein content in some tissues, such as the arteries, some ligaments, the lungs and the heart, can be hydrolysed or otherwise destroyed by a select group of enzymes classified as elastases. Human leukocyte elastase (HLE, EC 3.4.21.37), also known as human neutrophil elastase (HNE), is a glycosylated, strongly basic serine protease and is found in the azurophilic granules of human polymorphonuclear leukocytes (PMN). HNE is released from activated PMN and has been implicated causally in the pathogenesis of acute and chronic inflammatory diseases. HNE is capable of degrading a wide range of matrix proteins including elastin and collagen, and in addition to these actions on connective tissue HNE has a broad range of inflammatory actions including upregulation of IL-8 gene expression, oedema formation, mucus gland hyperplasia and mucus hypersecretion. It also acts as a mediator of tissue injury by hydrolysing collagen structures, e.g. in the heart after acute myocardial infarction or during the development of heart failure, thus damaging endothelial cells, promoting extravasation of neutrophils adhering to the endothelium and influencing the adhesion process itself.

Pulmonary diseases where HNE is believed to play a role include lung fibrosis, pneumonia, acute respiratory distress syndrome (ARDS), pulmonary emphysema, including smoking-induced emphysema, chronic obstructive pulmonary diseases (COPD) and cystic fibrosis. In cardiovascular diseases, HNE is involved in the enhanced generation of ischaemic tissue injury followed by myocardial dysfunction after acute myocardial infarction and in the remodelling processes occurring during the development of heart failure. HNE has also been causally implicated in rheumatoid arthritis, atherosclerosis, brain trauma, cancer and related conditions in which neutrophil participation is involved.

Thus, inhibitors of HLE activity can be potentially useful in the treatment of a number of inflammatory diseases, especially of chronic obstructive pulmonary diseases [R. A. Stockley, *Neutrophils and protease/antiprotease imbalance*, Am. J. Respir. Crit. Care 160, S49-S52 (1999)]. Inhibitors of HLE activity can also be potentially useful in the treatment of acute myocardial syndrome, unstable angina pectoris, acute myocardial infarction and coronary artery bypass grafts (CABG) [C. P. Tiefenbacher et al., *Inhibition of elastase improves myocardial function after repetitive ischaemia and myocardial infarction in the rat heart*, Eur. J. Physiol. 433, S563-S570 (1997); Dinerman et al., *Increased neutrophil elastase release in unstable angina pectoris and acute myocardial infarction*, J. Am. Coll. Cardiol. 15, 1559-1563 (1990)], of the development of heart failure [S. J. Gilbert et al., *Increased expression of promatrix metalloproteinase-9 and neutrophil elastase in canine dilated cardiomyopathy*, Cardiov. Res. 34, S377-S383 (1997)] and of atherosclerosis [Dollery et al., *Neutrophil elastase in human atherosclerotic plaque*, Circulation 107, 2829-2836 (2003)].

The synthesis of 5-ethoxycarbonyl-1-phenyl-6-methyl-4-(3-nitrophenyl)-3,4-dihydropyrimidin-2(1H)-one is described in J. Heterocyclic Chem. 38, 1051 (2001). A pharmacological activity of this compound is not mentioned.

The present invention relates to compounds of the general formula (I)

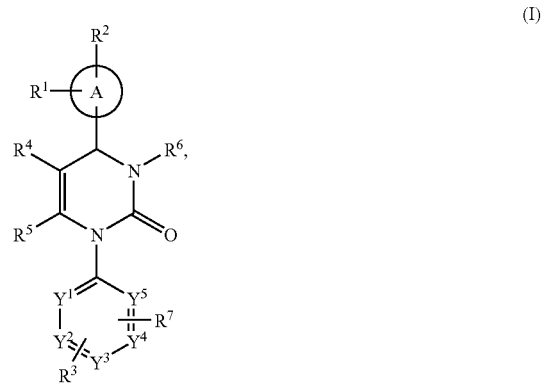

wherein

A represents an aryl or heteroaryl ring, $R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, $R^4$ represents $C_1$-$C_6$-alkyl which can be substituted by up to three radicals independently selected from the group consisting of hydroxy, $C_1$-$C_6$-alkoxycarbonyl and hydroxycarbonyl, $C_3$-$C_8$-cycloalkylcarbonyl which can be substituted by up to three radicals independently selected from the group consisting of $C_1$-$C_6$-alkyl, hydroxy, oxo, $C_1$-$C_6$-alkoxycarbonyl and hydroxycarbonyl, $C_1$-$C_6$-alkylcarbonyl which is substituted by phenyl-$C_1$-$C_6$-alkoxy or phenyl-$C_1$-$C_6$-alkoxycarbonyl which for their part, in the phenyl moiety, can be substituted by halogen, $C_1$-$C_6$-alkyl, hydroxy, $C_1$-$C_6$-alkoxy, $C_1$-$C_6$-alkoxycarbonyl or hydroxycarbonyl, $C_6$-$C_{10}$-arylcarbonyl which is substituted by one, two or three radicals independently selected from the group consisting of halogen, cyano, nitro, $C_1$-$C_6$-alkyl, trifluoromethyl, hydroxy, $C_1$-$C_6$-alkoxy, trifluoromethoxy, amino, $C_1$-$C_6$-alkoxycarbonyl, hydroxycarbonyl and phenyl, $C_1$-$C_6$-alkoxycarbonyl which is substituted by one or two radicals independently selected from the group consisting of phenyl-$C_1$-$C_6$-alkoxy, phenyl-$C_1$-$C_6$-alkoxycarbonyl, $C_1$-$C_6$-alkoxy, $C_1$-$C_6$-alkoxycarbonylamino and 5- or 6-membered heterocyclyl, wherein $C_1$-$C_6$-alkoxy is further substituted by $C_1$-$C_6$-alkoxycarbonyl or hydroxycarbonyl, and 5- or 6-membered heterocyclyl is further substituted by hydroxy, oxo, $C_1$-$C_6$-alkoxycarbonyl or hydroxycarbonyl, heteroarylcarbonyl which is substituted by one or two radicals independently selected from the group consisting of hydroxy, amino, halogen, $C_1$-$C_6$-alkoxy, $C_1$-$C_6$-alkoxycarbonyl and hydroxycarbonyl, and which can additionally be substituted by $C_1$-$C_6$-alkyl, mono- or di-$C_1$-$C_6$-alkylaminocarbonyl wherein the alkyl moiety or at least one alkyl moiety, respectively, is substituted by $C_6$-$C_{10}$-aryl which for its part can be further substituted by up to three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl and hydroxycarbonyl, $C_6$-$C_{10}$-arylaminocarbonyl or N—($C_1$-$C_6$-alkyl)-N—($C_6$-$C_{10}$-aryl)aminocarbonyl wherein aryl is substituted by one, two or three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl and hydroxycarbonyl, and wherein alkyl, when present, can be substituted by up to three radicals independently selected from the group consisting of hydroxy, $C_1$-$C_6$-alkoxy, $C_1$-$C_6$-alkoxycarbonyl and hydroxycarbonyl, $C_3$-$C_8$-cycloalkylaminocarbonyl or N—($C_1$-$C_6$-alkyl)-N—($C_3$-$C_8$-cycloalkyl)aminocarbonyl wherein cycloalkyl can be substituted by up to three radicals independently selected from the group consisting of $C_1$-$C_6$-alkyl, hydroxy, oxo, $C_1$-$C_6$-alkoxycarbonyl and hydroxycarbonyl, and wherein alkyl, when present, can be substituted by up to three radicals independently selected from the group consisting of hydroxy, $C_1$-$C_6$-alkoxy, $C_1$-$C_6$-alkoxycarbonyl and hydroxycarbonyl, heterocyclylcarbonyl which is substituted by one, two or three radicals independently selected from the group consisting of $C_1$-$C_6$-alkyl, hydroxy, oxo, $C_1$-$C_6$-alkoxy, $C_1$-$C_6$-alkoxycarbonyl, phenyl-$C_1$-$C_6$-alkoxycarbonyl, hydroxycarbonyl, 5- or 6-membered heterocyclyl, 5- or 6-membered heteroaryl and $C_6$-$C_{10}$-aryl, wherein $C_1$-$C_6$-alkyl is further substituted by hydroxy, $C_1$-$C_6$-alkoxy, $C_1$-$C_6$-alkoxycarbonyl or hydroxycarbonyl, and wherein $C_6$-$C_{10}$-aryl can be further substituted by up to three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl and hydroxycarbonyl, N-(heterocyclyl)aminocarbonyl wherein heterocyclyl can be further substituted by up to three radicals independently selected from the group consisting of $C_1$-$C_6$-alkyl, hydroxy, oxo, $C_1$-$C_6$-alkoxy, $C_1$-$C_6$-alkoxycarbonyl, hydroxycarbonyl and phenyl-$C_1$-$C_6$-alkyl, a group of the formula —C(=O)—NR$^a$—SO$_2$—R$^b$ wherein R$^a$ represents hydrogen or $C_1$-$C_6$-alkyl, and R$^b$ represents $C_1$-$C_6$-alkyl which can be substituted by trifluoromethyl, or R$^b$ represents $C_6$-$C_{10}$-aryl which can be substituted by $C_1$-$C_6$-alkyl, halogen, cyano, nitro or trifluoromethyl, or a group of the formula —P(=O)(OR$^c$)$_2$ wherein R$^c$ represents hydrogen or $C_1$-$C_6$-alkyl, R$^5$ represents $C_1$-$C_4$-alkyl, which can be substituted with one to three identical or different radicals selected from the group consisting of halogen, hydroxy, $C_1$-$C_6$-alkoxy, $C_2$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl and the radical —O—$C_1$-$C_4$-alkyl-O—$C_1$-$C_4$-alkyl, R$^6$ represents hydrogen, $C_1$-$C_6$-alkyl, formyl, aminocarbonyl, mono- or di-$C_1$-$C_4$-alkylaminocarbonyl, $C_3$-$C_8$-cycloalkylcarbonyl, $C_1$-$C_6$-alkylcarbonyl, $C_1$-$C_6$-alkoxycarbonyl, N—($C_1$-$C_4$-alkylsulfonyl)-aminocarbonyl, N—($C_1$-$C_4$-alkylsulfonyl)-N—($C_1$-$C_4$-alkyl)-aminocarbonyl, heteroaryl, heterocyclyl, heteroarylcarbonyl or heterocyclylcarbonyl, wherein $C_1$-$C_6$-alkyl, mono- and di-$C_1$-$C_4$-alkylaminocarbonyl, $C_1$-$C_6$-alkylcarbonyl, $C_1$-$C_6$-alkoxycarbonyl, heteroaryl and heterocyclyl can be substituted with one to three identical or different radicals selected from the group consisting of aryl, heteroaryl, hydroxy, $C_1$-$C_4$-alkoxy, hydroxycarbonyl, $C_1$-$C_6$-alkoxycarbonyl, aminocarbonyl, mono- and di-$C_1$-$C_4$-alkylaminocarbonyl, amino, mono- and di-$C_1$-$C_4$-alkylamino, $C_1$-$C_4$-alkylcarbonylamino, tri-($C_1$-$C_6$-alkyl)-silyl, cyano, N-(mono- or di-$C_1$-$C_4$-alkylamino-$C_1$-$C_4$-alkyl)-aminocarbonyl, N—($C_1$-$C_4$-alkoxy-$C_1$-$C_4$-alkyl)-aminocarbonyl and halogen, or R$^6$ represents a moiety of the formula

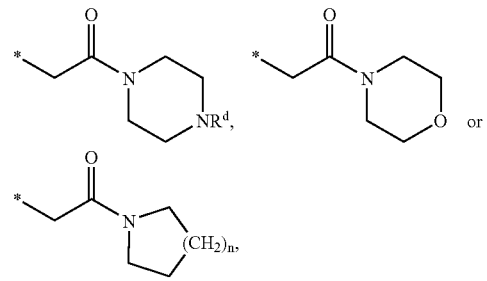

wherein

R$^d$ is selected from the group consisting of hydrogen and $C_1$-$C_6$-alkyl, and n represents an integer of 1 or 2, or R$^6$ represents a group of the formula -T-U wherein T represents a $C_1$-$C_6$-alkanediyl or $C_2$-$C_6$-alkenediyl group and U represents $C_6$-$C_{10}$-aryl or 5- or 6-membered heteroaryl each of which is substituted by one, two or three radicals independently selected from the group consisting of halogen, $C_1$-$C_6$-alkyl, 5- or 6-membered heteroaryl and a group of the formula —V—W wherein V represents a bond or a $C_1$-$C_6$-alkanediyl or $C_2$-$C_6$-alkenediyl group both of which can be further substituted by $C_3$-$C_8$-cycloalkyl, and W represents $C_1$-$C_6$-alkoxycarbonyl or hydroxycarbonyl, a group of the formula —C(=O)—NR$^e$—SO$_2$—R$^f$ wherein R$^e$ represents hydrogen or $C_1$-$C_6$-alkyl, and R$^f$ represents $C_1$-$C_6$-alkyl which can be substituted by trifluoromethyl, or R$^f$ represents $C_6$-$C_{10}$-aryl which can be substituted by $C_1$-$C_6$-alkyl, halogen, cyano, nitro or trifluoromethyl, a group of the formula —C(=O)—NR$^g$R$^h$ wherein R$^g$ represents hydrogen or $C_1$-$C_6$-alkyl, and R$^b$ represents $C_6$-$C_{10}$-aryl which can be substituted by $C_1$-$C_6$-alkoxycarbonyl or hydroxycarbonyl, a group of the formula —C(=O)—N$^j$—OR$^k$ wherein R$^i$ and R$^k$ independently from each other represent hydrogen or $C_1$-$C_6$-alkyl, or $C_6$-$C_{10}$-arylalkoxy which, in the aryl part, can be substituted by halogen, $C_1$-$C_6$-alkyl, $C_1$-$C_6$-alkoxycarbonyl or hydroxycarbonyl, or R$^6$ represents $C_3$-$C_8$-cycloalkyl which can be substituted by up to three radicals independently selected from the group consisting of $C_1$-$C_6$-alkyl, hydroxy, oxo, $C_1$-$C_6$-alkoxycarbonyl and hydroxycarbonyl, $C_2$-$C_6$-alkenyl which can be substituted by $C_1$-$C_6$-alkoxycarbonyl or hydroxycarbonyl, $C_1$-$C_6$-alkylcarbonyl which is substituted by $C_1$-$C_6$-alkoxycarbonylamino, $C_1$-$C_6$-alkoxycarbonyl which is substituted by phenyl-$C_1$-$C_6$-alkoxycarbonyl which for its part, in the phenyl moiety, can be further substituted by halogen, $C_1$-$C_6$-alkyl, $C_1$-$C_6$-alkoxycarbonyl or hydroxycarbonyl, or a group of the formula —$SO_2$—$R'''$ wherein $R'''$ represents $C_1$-$C_6$-alkyl which can be substituted by trifluoromethyl, or $R'''$ represents $C_6$-$C_{10}$-aryl which can be substituted by $C_1$-$C_6$-alkyl, halogen, cyano, nitro, trifluoromethyl, $C_1$-$C_6$-alkoxycarbonyl or hydroxycarbonyl, $R^7$ represents halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, and $Y^1, Y^2, Y^3, Y^4$ and $Y^5$ independently from each other represent CH or N, wherein the ring contains either 0, 1 or 2 nitrogen atoms.

The compounds according to this invention can also be present in the form of their salts, hydrates and/or solvates.

Physiologically acceptable salts are preferred in the context of the present invention.

Physiologically acceptable salts according to the invention are non-toxic salts which in general are accessible by reaction of the compounds (I) with an inorganic or organic base or acid conventionally used for this purpose. Non-limiting examples of pharmaceutically acceptable salts of compounds (I) include the alkali metal salts, e.g. lithium, potassium and sodium salts, the alkaline earth metal salts such as magnesium and calcium salts, the quaternary ammonium salts such as, for example, triethyl ammonium salts, acetates, benzene sulphonates, benzoates, dicarbonates, disulphates, ditartrates, borates, bromides, carbonates, chlorides, citrates, dihydrochlorides, fumarates, gluconates, glutamates, hexyl resorcinates, hydrobromides, hydrochlorides, hydroxynaphthoates, iodides, isothionates, lactates, laurates, malates, maleates, mandelates, mesylates, methylbromides, methylnitrates, methylsulphates, nitrates, oleates, oxalates, palmitates, pantothenates, phosphates, diphosphates, polygalacturonates, salicylates, stearates, sulphates, succinates, tartrates, tosylates, valerates, and other salts used for medicinal purposes.

Hydrates of the compounds of the invention or their salts are stoichiometric compositions of the compounds with water, such as for example hemi-, mono-, or dihydrates.

Solvates of the compounds of the invention or their salts are stoichiometric compositions of the compounds with solvents.

The present invention includes both the individual enantiomers or diastereomers and the corresponding racemates or diastereomeric mixtures of the compounds according to the invention and their respective salts. In addition, all possible tautomeric forms of the compounds described above are included according to the present invention. The diastereomeric mixtures can be separated into the individual isomers by chromatographic processes. The racemates can be resolved into the respective enantiomers either by chromatographic processes on chiral phases or by resolution.

In the context of the present invention, the substituents, if not stated otherwise, in general have the following meaning:

Alkyl in general represents a straight-chain or branched saturated hydrocarbon radical having 1 to 6, preferably 1 to 4 carbon atoms. Non-limiting examples include methyl, ethyl, n-propyl, isopropyl, n-butyl, isobutyl, sec.-butyl, tert.-butyl, pentyl, isopentyl, hexyl, isohexyl. The same applies to radicals such as alkoxy, alkylamino, alkylthio, alkylcarbonyl, alkoxycarbonyl, alkoxycarbonylamino and the like.

Alkanediyl in general represents a straight-chain or branched divalent alkane radical having 1 to 6, preferably 1 to 4 carbon atoms. Non-limiting examples include 1,2-ethylene, 1,3-propylene, propane-1,2-diyl, propane-2,2-diyl, 1,4-butylene, butane-1,3-diyl, butane-2,4-diyl, pentane-2,4-diyl, 2-methyl-pentane-2,4-diyl.

Alkenediyl in general represents a straight-chain or branched divalent alkene radical having 2 to 6, preferably 2 to 4 carbon atoms, and up to three double bonds. Non-limiting examples include ethene-1,2-diyl, ethene-1,1-diyl, propene-1,1-diyl, propene-1,2-diyl, propene-1,3-diyl, propene-3,3-diyl, propene-2,3-diyl, but-2-ene-1,4-diyl, 1,3-butadiene-1,4-diyl, pent-2-ene-1,4-diyl, hex-2-ene-1,4-diyl.

Alkoxy illustratively and preferably represents methoxy, ethoxy, n-propoxy, isopropoxy, tert.-butoxy, n-pentoxy and n-hexoxy.

Arylalkoxy and phenylalkoxy in general represent a straight-chain or branched alkoxy radical which is substituted with an aryl or a phenyl group, respectively. Non-limiting examples include benzyloxy, naphthylmethoxy, 1-phenylethoxy, 2-phenylethoxy, 2-naphthylethoxy, 3-phenylpropoxy, 4-phenylbutoxy. The same applies to the radical phenylalkoxycarbonyl.

Alkenoxy illustratively and preferably represents allyloxy, but-2-en-1-oxy, pent-3-en-1-oxy and hex-2-en-1-oxy.

Alkylcarbonyl in general represents a straight-chain or branched hydrocarbon radical having 1 to 6, preferably 1 to 4 carbon atoms which has a carbonyl function at the position of attachment. Non-limiting examples include formyl, acetyl, n-propionyl, n-butyryl, isobutyryl, pivaloyl, n-hexanoyl.

Alkylcarbonylamino in general represents a straight-chain or branched hydrocarbon radical having 1 to 6, preferably 1 to 4 carbon atoms which has a carbonylamino (—CO—NH—) function at the position of attachment and which is bonded to the carbonyl group. Non-limiting examples include formylamino, acetylamino, n-propionylamino, n-butyrylamino, isobutyrylamino, pivaloylamino, n-hexanoylamino.

Alkoxycarbonyl illustratively and preferably represents methoxycarbonyl, ethoxycarbonyl, n-propoxycarbonyl, isopropoxycarbonyl, tert.-butoxycarbonyl, n-pentoxycarbonyl and n-hexoxycarbonyl.

Alkenoxycarbonyl illustratively and preferably represents allyloxycarbonyl, but-2-en-1-oxycarbonyl, pent-3-en-1-oxycarbonyl and hex-2-en-1-oxycarbonyl.

Alkylamino represents an alkylamino radical having one or two (independently selected) alkyl residues, illustratively and preferably representing methylamino, ethylamino, n-propylamino, isopropylamino, tert.-butylanino, n-pentylamino, n-hexylamino, N,N-dimethylamino, N,N-diethylamino, N-ethyl-N-methylamino, N-methyl-N-n-propylamino, N-isopropyl-N-n-propylamino, N-tert.-butyl-N-methylamino, N-ethyl-N-n-pentylamino and N-n-hexyl-N-methylamino.

Alkylaminocarbonyl represents an alkylaminocarbonyl radical having one or two (independently selected) alkyl residues, illustratively and preferably representing methylaminocarbonyl, ethylaminocarbonyl, n-propylaminocarbonyl, isopropylaminocarbonyl, tert.-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert.-butyl-N-methylaminocarbonyl, N-ethyl-N-n-pentylamino-carbonyl and N-n-hexyl-N-methylaminocatbonyl.

Alkylsulfonyl in general represents a straight-chain or branched hydrocarbon radical having 1 to 6, preferably 1 to 4 carbon atoms which has a sulfonyl function at the position of attachment. Non-limiting examples include methylsulfonyl, ethylsulfonyl, n-propylsulfonyl, isopropylsulfonyl, n-butylsulfonyl, tert.-butylsulfonyl.

Cycloalkyl in general represents a cyclic saturated hydrocarbon radical having 3 to 8, preferably 3 to 6 carbon atoms. Non-limiting examples include cyclopropyl, cyclobutyl, cyclopentyl, cyclohexyl and cycloheptyl. The same applies to radicals such as cycloalkylcarbonyl.

Aryl in general represents a mono- to tricyclic aromatic carbocyclic radical having 6 to 14, preferably 6 to 10 carbon atoms, illustratively and preferably representing phenyl, naphthyl and phenanthrenyl. The same applies to radicals such as arylcarbonyl, arylalkoxy and arylaminocarbonyl.

Arylcarbonyl illustratively and preferably represents benzoyl and naphthoyl.

Arylaminocarbonyl illustratively and preferably represents phenylaminocarbonyl and naphthylaminocarbonyl.

Heteroaryl per se and in heteroarylcarbonyl in general represents an aromatic mono- or bicyclic radical having 5 to 10 and preferably 5 or 6 ring atoms, and up to 5 and preferably up to 4 heteroatoms selected from the group consisting of S, O and N, illustratively and preferably representing thienyl, furyl, pyrrolyl, thiazolyl, oxazolyl, isothiazolyl, isoxazolyl, imidazolyl, oxadiazolyl, thiadiazolyl, pyridyl, pyrimidyl, pyridazinyl, indolyl, indazolyl, benzofuranyl, benzothienyl, benzothiazolyl, quinolinyl, isoquinolinyl.

Heteroarylcarbonyl illustratively and preferably represents thienylcarbonyl, furylcarbonyl, pyrrolylcarbonyl, thiazolylcarbonyl, oxazolylcarbonyl, isothiazolylcarbonyl, isoxazolylcarbonyl, imidazolylcarbonyl, pyridylcarbonyl, pyrimidylcarbonyl, pyridazinylcarbonyl, indolylcarbonyl, indazolylcarbonyl, benzofuranylcarbonyl, benzothienylcarbonyl, quinolinylcarbonyl, isoquinolinylcarbonyl.

Heterocyclyl per se and in heterocyclylcarbonyl in general represents a mono- or polycyclic, preferably mono- or bicyclic, non-aromatic heterocyclic radical having 4 to 10 and preferably 5 to 8 ring atoms, and up to 3 and preferably up to 2 heteroatoms and/or hetero-groups selected from the group consisting of N, O, S, SO and $SO_2$. The heterocyclyl radicals can be saturated or partially unsaturated. Preference is given to 5- to 8-membered monocyclic saturated heterocyclyl radicals having up to two heteroatoms selected from the group consisting of O, N and S, such as illustratively and preferably tetrahydrofuran-2-yl, 1,3-dioxolan-4-yl, pyrrolidin-1-yl, pyrrolidin-2-yl, pyrrolidin-3-yl, pyrrolinyl, piperidinyl, piperazinyl, morpholinyl, thiomorpholinyl, perhydroazepinyl.

Heterocyclylcarbonyl illustratively and preferably represents tetrahydrofuran-2-carbonyl, 1,3-dioxolan-4-carbonyl, pyrrolidin-1-carbonyl, pyrrolidin-2-carbonyl, pyrrolidin-3-carbonyl, pyrrolincarbonyl, piperidincarbonyl, morpholincarbonyl, perhydroazepincarbonyl.

Halogen represents fluorine, chlorine, bromine and iodine.

When stated, that $Y^1$, $Y^2$, $Y^3$, $Y^4$ and $Y^5$ represent CH or N, CH shall also stand for a ring carbon atom, which is substituted with a substituent $R^3$ or $R^7$.

A * symbol next to a bond denotes the point of attachment in the molecule.

In another preferred embodiment, the present invention relates to compounds of general formula (I), wherein
A represents an aryl or heteroaryl ring,
$R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy,
$R^4$ represents
$C_1$-$C_6$-alkyl which can be substituted by up to three radicals independently selected from the group consisting of hydroxy, $C_1$-$C_6$-alkoxycarbonyl and hydroxycarbonyl,
$C_3$-$C_8$-cycloalkylcarbonyl which can be substituted by up to three radicals independently selected from the group consisting of $C_1$-$C_6$-alkyl, hydroxy, oxo, $C_1$-$C_6$-alkoxycarbonyl and hydroxycarbonyl,
$C_6$-$C_{10}$-arylcarbonyl which is substituted by one, two or three radicals independently selected from the group consisting of halogen, cyano, $C_1$-$C_6$-alkyl, trifluoromethyl, hydroxy, $C_1$-$C_6$-alkoxy, trifluoromethoxy, $C_1$-$C_6$-alkoxycarbonyl and hydroxycarbonyl,
$C_1$-$C_6$-alkoxycarbonyl which is substituted by one or two radicals independently selected from the group consisting of phenyl-$C_1$-$C_6$-alkoxy, phenyl-$C_1$-$C_6$-alkoxycarbonyl, $C_1$-$C_6$-alkoxy, $C_1$-$C_6$-alkoxycarbonylamino and 5- or 6-membered heterocyclyl, wherein $C_1$-$C_6$-alkoxy is further substituted by $C_1$-$C_6$-alkoxycarbonyl or hydroxycarbonyl, and 5- or 6-membered heterocyclyl is further substituted by hydroxy, oxo, $C_1$-$C_6$-alkoxycarbonyl or hydroxycarbonyl,
heteroarylcarbonyl which is substituted by one or two radicals independently selected from the group consisting of hydroxy, amino, halogen, $C_1$-$C_6$-alkoxy, $C_1$-$C_6$-alkoxycarbonyl and hydroxycarbonyl, and which can additionally be substituted by $C_1$-$C_6$-alkyl,
mono- or di-$C_1$-$C_6$-alkylaminocarbonyl wherein the alkyl moiety or at least one alkyl moiety, respectively, is substituted by $C_6$-$C_{10}$-aryl which for its part can be further substituted by up to three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl and hydroxycarbonyl,
heterocyclylcarbonyl which is substituted by one, two or three radicals independently selected from the group consisting of $C_1$-$C_6$-alkyl, hydroxy, oxo, $C_1$-$C_6$-alkoxy, $C_1$-$C_6$-alkoxycarbonyl, phenyl-$C_1$-$C_6$-alkoxycarbonyl, hydroxycarbonyl, 5- or 6-membered heterocyclyl, 5- or 6-membered heteroaryl and $C_6$-$C_{10}$-aryl, wherein $C_1$-$C_6$-alkyl is further substituted by hydroxy, $C_1$-$C_6$-alkoxy, $C_1$-$C_6$-alkoxycarbonyl or hydroxycarbonyl, and wherein $C_6$-$C_{10}$-aryl can be further substituted by up to three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl and hydroxycarbonyl,
or
a group of the formula —C(=O)—NH—$SO_2$—$R^b$ wherein $R^b$ represents $C_1$-$C_6$-alkyl which can be substituted by trifluoromethyl, or $R^b$ represents $C_6$-$C_{10}$-aryl which can be substituted by $C_1$-$C_6$-alkyl, halogen, cyano, nitro or trifluoromethyl,
$R^5$ represents $C_1$-$C_4$-alkyl, which can be substituted with one to three identical or different radicals selected from the group consisting of halogen, hydroxy, $C_1$-$C_6$-alkoxy, $C_2$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl and the radical —O—$C_1$-$C_4$-alkyl-O—$C_1$-$C_4$-alkyl,
$R^6$ represents hydrogen, $C_1$-$C_6$-alkyl, aminocarbonyl, mono- or di-$C_1$-$C_4$-alkylaminocarbonyl, $C_3$-$C_8$-cycloalkylcarbonyl, $C_1$-$C_6$-alkylcarbonyl, $C_1$-$C_6$-alkoxycarbonyl, N—($C_1$-$C_4$-alkylsulfonyl)-aminocarbonyl, N—($C_1$-$C_4$-alkylsulfonyl)-N—($C_1$-$C_4$-alkyl)-aminocarbonyl, heteroarylcarbonyl or heterocyclylcarbonyl, wherein $C_1$-$C_6$-alkyl, mono- and di-$C_1$-$C_4$-alkylaminocarbonyl, $C_1$-$C_6$-alkylcarbonyl and $C_1$-$C_6$-alkoxycarbonyl can be substituted with one to three identical or different radicals selected from the group consisting of aryl, heteroaryl, hydroxy, $C_1$-$C_4$-alkoxy, hydroxycarbonyl, $C_1$-$C_6$-alkoxycarbonyl, aminocarbonyl, mono- and di-$C_1$-$C_4$-alkylaminocarbonyl, amino, mono- and di-$C_1$-$C_4$-alkylamino, $C_1$-$C_4$-alkylcarbonylamino, N-(mono- or di-$C_1$-$C_4$-alkylamino-$C_1$-$C_4$-alkyl)-aminocarbonyl, N—($C_1$-$C_4$-alkoxy-$C_1$-$C_4$-alkyl)-aminocarbonyl and halogen, or $R^6$ represents a moiety of the formula

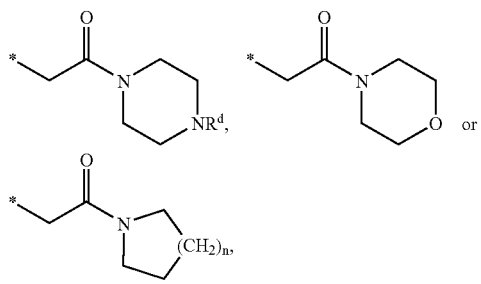

wherein $R^d$ is selected from the group consisting of hydrogen and $C_1$-$C_6$-alkyl, and n represents an integer of 1 or 2, or $R^6$ represents a group of the formula -T-U wherein T represents a $C_1$-$C_4$-alkanediyl or $C_2$-$C_4$-alkenediyl group and U represents $C_6$-$C_{10}$-aryl or 5- or 6-membered heteroaryl each of which is substituted by one, two or three radicals independently selected from the group consisting of halogen, $C_1$-$C_6$-alkyl, 5- or 6-membered heteroaryl and a group of the formula —V—W wherein V represents a bond, a $C_2$-$C_6$-alkenediyl group or a $C_1$-$C_6$-alkanediyl group the latter of which can be further substituted by $C_3$-$C_8$-cycloalkyl, and W represents $C_1$-$C_6$-alkoxycarbonyl or hydroxycarbonyl, a group of the formula —C(=O)—NH—SO$_2$—$R^f$ wherein $R^f$ represents $C_1$-$C_6$-alkyl which can be substituted by trifluoromethyl, or $R^f$ represents $C_6$-$C_{10}$-aryl which can be substituted by $C_1$-$C_6$-alkyl, halogen, cyano, nitro or trifluoromethyl, or a group of the formula —C(=O)—NHR$^h$ wherein $R^h$ represents $C_6$-$C_{10}$-aryl which can be substituted by $C_1$-$C_6$-alkoxycarbonyl or hydroxycarbonyl, or $R^6$ represents $C_3$-$C_8$-cycloalkyl which can be substituted by up to three radicals independently selected from the group consisting of $C_1$-$C_6$-alkyl, hydroxy, oxo, $C_1$-$C_6$-alkoxycarbonyl and hydroxycarbonyl, or $C_2$-$C_6$-alkenyl which can be substituted by $C_1$-$C_6$-alkoxycarbonyl or hydroxycarbonyl, $R^7$ represents halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, and $Y^1, Y^2, Y^3, Y^4$ and $Y^5$ independently from each other represent CH or N, wherein the ring contains either 0, 1 or 2 nitrogen atoms.

In another particularly preferred embodiment, the present invention relates to compounds of general formula (I), wherein A represents a phenyl, naphthyl or pyridyl ring, $R^1, R^2$ and $R^3$ independently from each other represent hydrogen, fluoro, chloro, bromo, nitro, cyano, methyl, ethyl, trifluoromethyl or trifluoromethoxy, $R^4$ represents $C_1$-$C_4$-alkyl which can be substituted by up to two radicals independently selected from the group consisting of hydroxy, $C_1$-$C_4$-alkoxycarbonyl and hydroxycarbonyl, $C_3$-$C_6$-cycloalkylcarbonyl which can be substituted by up to two radicals independently selected from the group consisting of $C_1$-$C_4$-alkyl, hydroxy, oxo, $C_1$-$C_4$-alkoxycarbonyl and hydroxycarbonyl, benzoyl which is substituted by one, two or three radicals independently selected from the group consisting of fluoro, chloro, bromo, cyano, $C_1$-$C_4$-alkyl, trifluoromethyl, hydroxy, $C_1$-$C_4$-alkoxy, trifluoromethoxy, $C_1$-$C_4$-alkoxycarbonyl and hydroxycarbonyl, $C_1$-$C_4$-alkoxycarbonyl which is substituted by one or two radicals independently selected from the group consisting of benzyloxy, benzyloxycarbonyl, $C_1$-$C_4$-alkoxy, $C_1$-$C_4$-alkoxycarbonylamino, pyrrolidinyl, piperidinyl and morpholinyl, wherein $C_1$-$C_4$-alkoxy is further substituted by $C_1$-$C_4$-alkoxycarbonyl or hydroxycarbonyl, and wherein pyrrolidinyl, piperidinyl and morpholinyl is further substituted by hydroxy, oxo, $C_1$-$C_4$-alkoxycarbonyl or hydroxycarbonyl, furylcarbonyl, thienylcarbonyl, oxazolylcarbonyl, thiazolylcarbonyl, pyridylcarbonyl or pyrimidinylcarbonyl each of which is substituted by one or two radicals independently selected from the group consisting of hydroxy, amino, fluoro, chloro, bromo, $C_1$-$C_4$-alkoxy, $C_1$-$C_4$-alkoxycarbonyl and hydroxycarbonyl, and each of which can additionally be substituted by $C_1$-$C_4$-alkyl, mono- or di-$C_1$-$C_4$-alkylaminocarbonyl wherein the alkyl moiety or at least one alkyl moiety, respectively, is substituted by phenyl which for its part can be further substituted by up to three radicals independently selected from the group consisting of fluoro, chloro, bromo, cyano, trifluoromethyl, $C_1$-$C_4$-alkyl, hydroxy, $C_1$-$C_4$-alkoxy, trifluoromethoxy, $C_1$-$C_4$-alkoxycarbonyl and hydroxycarbonyl, tetrahydrofurylcarbonyl, tetrahydropyranylcarbonyl, piperidinylcarbonyl, piperazinylcarbonyl or morpholinylcarbonyl each of which is substituted by one or two radicals independently selected from the group consisting of $C_1$-$C_4$-alkyl, hydroxy, oxo, $C_1$-$C_4$-alkoxy, $C_1$-$C_4$-alkoxycarbonyl, benzyloxycarbonyl, hydroxycarbonyl, piperidinyl, morpholinyl, pyridyl and phenyl, wherein $C_1$-$C_4$-alkyl is further substituted by hydroxy, $C_1$-$C_4$-alkoxy, $C_1$-$C_4$-alkoxycarbonyl or hydroxycarbonyl, and wherein phenyl can be further substituted by up to three radicals independently selected from the group consisting of fluoro, chloro, bromo, cyano, trifluoromethyl, $C_1$-$C_4$-alkyl, hydroxy, $C_1$-$C_4$-alkoxy, trifluoromethoxy, $C_1$-$C_4$-alkoxycarbonyl and hydroxycarbonyl, or
a group of the formula —C(=O)—NH—SO$_2$—R$^b$ wherein R$^b$ represents C$_1$-C$_4$-alkyl which can be substituted by trifluoromethyl, or R$^b$ represents phenyl which can be substituted by C$_1$-C$_4$-alkyl, fluoro, chloro, bromo, cyano, nitro or trifluoromethyl, R$^5$ represents methyl or ethyl, R$^6$ represents hydrogen, C$_1$-C$_6$-alkyl, mono- or di-C$_1$-C$_4$-alkylaminocarbonyl, C$_1$-C$_6$-alkylcarbonyl, C$_1$-C$_6$-alkoxycarbonyl or heterocyclylcarbonyl, wherein C$_1$-C$_6$-alkyl and C$_1$-C$_6$-alkoxycarbonyl can be substituted with one to three identical or different radicals selected from the group consisting of hydroxy, C$_1$-C$_4$-alkoxy, hydroxycarbonyl, C$_1$-C$_6$-alkoxycarbonyl, aminocarbonyl, mono- and di-C$_1$-C$_4$-alkylaminocarbonyl, amino, mono- and di-C$_1$-C$_4$-alkylamino, or R$^6$ represents a moiety of the formula

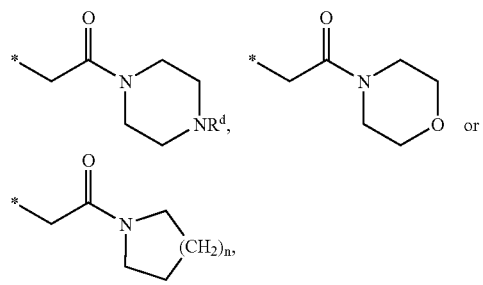

wherein
R$^d$ is selected from the group consisting of hydrogen and C$_1$-C$_4$-alkyl, and
n represents an integer of 1 or 2, or R$^6$ represents a group of the formula -T-U wherein
T represents a C$_1$-C$_4$-alkanediyl group
and
U represents
phenyl, furyl, thienyl, oxazolyl, thiazolyl or pyridyl each of which is substituted by one or two radicals independently selected from the group consisting of fluoro, chloro, bromo, C$_1$-C$_4$-alkyl, thienyl, pyridyl and a group of the formula —V—W wherein V represents a bond or a C$_1$-C$_4$-alkanediyl or C$_2$-C$_4$-alkenediyl group, and W represents C$_1$-C$_4$-alkoxycarbonyl or hydroxycarbonyl,
a group of the formula —C(=O)—NH—SO$_2$—R$^f$ wherein R$^f$ represents C$_1$-C$_4$-alkyl which can be substituted by trifluoromethyl, or R$^f$ represents phenyl which can be substituted by C$_1$-C$_4$-alkyl, fluoro, chloro, bromo, cyano, nitro or trifluoromethyl,
or
a group of the formula —C(=O)—NHR$^h$ wherein R$^h$ represents phenyl which can be substituted by C$_1$-C$_4$-alkoxycarbonyl or hydroxycarbonyl, or R$^6$ represents
C$_3$-C$_6$-cycloalkyl which can be substituted by up to two radicals independently selected from the group consisting of C$_1$-C$_4$-alkyl, hydroxy, oxo, C$_1$-C$_4$-alkoxycarbonyl and hydroxycarbonyl,
or
C$_2$-C$_4$-alkenyl which is substituted by C$_1$-C$_4$-alkoxycarbonyl or hydroxycarbonyl, R$^7$ represents halogen, nitro, cyano, trifluoromethyl, trifluoromethoxy, methyl or ethyl,
and
Y$^1$, Y$^2$, Y$^3$, Y$^4$ and Y$^5$ each represent CH.

In another very particularly preferred embodiment, the present invention relates to compounds of general formula (I), wherein
A represents a phenyl or a pyridyl ring,
R$^1$ and R$^3$ each represent hydrogen,
R$^2$ represents fluoro, chloro, bromo, nitro or cyano,
R$^4$ represents
C$_1$-C$_4$-alkyl which can be substituted by up to two radicals independently selected from the group consisting of hydroxy, C$_1$-C$_4$-alkoxycarbonyl and hydroxycarbonyl,
C$_3$-C$_6$-cycloalkylcarbonyl which can be substituted by up to two radicals independently selected from the group consisting of C$_1$-C$_4$-alkyl, hydroxy, oxo, C$_1$-C$_4$-alkoxycarbonyl and hydroxycarbonyl,
benzoyl which is substituted by one, two or three radicals independently selected from the group consisting of fluoro, chloro, bromo, cyano, C$_1$-C$_4$-alkyl, trifluoromethyl, hydroxy, C$_1$-C$_4$-alkoxy, trifluoromethoxy, C$_1$-C$_4$-alkoxycarbonyl and hydroxycarbonyl,
C$_1$-C$_4$-alkoxycarbonyl which is substituted by one or two radicals independently selected from the group consisting of benzyloxy, benzyloxycarbonyl, C$_1$-C$_4$-alkoxy, C$_1$-C$_4$-alkoxycarbonylamino, pyrrolidinyl, piperidinyl and morpholinyl, wherein C$_1$-C$_4$-alkoxy is further substituted by C$_1$-C$_4$-alkoxycarbonyl or hydroxycarbonyl, and wherein pyrrolidinyl, piperidinyl and morpholinyl is further substituted by hydroxy, oxo, C$_1$-C$_4$-alkoxycarbonyl or hydroxycarbonyl,
furylcarbonyl, oxazolylcarbonyl, thiazolylcarbonyl or pyridylcarbonyl each of which is substituted by one or two radicals independently selected from the group consisting of hydroxy, amino, fluoro, chloro, bromo, C$_1$-C$_4$-alkoxy, C$_1$-C$_4$-alkoxycarbonyl and hydroxycarbonyl, and each of which can additionally be substituted by C$_1$-C$_4$-alkyl,
mono- or di-C$_1$-C$_4$-alkylaminocarbonyl wherein the alkyl moiety or at least one alkyl moiety, respectively, is substituted by phenyl which for its part can be further substituted by up to three radicals independently selected from the group consisting of fluoro, chloro, bromo, cyano, trifluoromethyl, C$_1$-C$_4$-alkyl, hydroxy, C$_1$-C$_4$-alkoxy, trifluoromethoxy, C$_1$-C$_4$-alkoxycarbonyl and hydroxycarbonyl,
piperidinylcarbonyl, piperazinylcarbonyl or morpholinylcarbonyl each of which is substituted by one or two radicals independently selected from the group consisting of C$_1$-C$_4$-alkyl, hydroxy, oxo, C$_1$-C$_4$-alkoxy, C$_1$-C$_4$-alkoxycarbonyl, benzyloxycarbonyl, hydroxycarbonyl, piperidinyl, morpholinyl, pyridyl and phenyl, wherein C$_1$-C$_4$-alkyl is further substituted by hydroxy, C$_1$-C$_4$-alkoxy, C$_1$-C$_4$-alkoxycarbonyl or hydroxycarbonyl, and wherein phenyl can be further substituted by up to three radicals independently selected from the group consisting of fluoro, chloro, bromo, cyano, trifluoromethyl, C$_1$-C$_4$-alkyl, hydroxy, C$_1$-C$_4$-alkoxy, trifluoromethoxy, C$_1$-C$_4$-alkoxycarbonyl and hydroxycarbonyl,
or
a group of the formula —C(=O)—NH—SO$_2$—R$^b$ wherein R$^b$ represents C$_1$-C$_4$-alkyl which can be substituted by trifluoromethyl, or R$^b$ represents phenyl which can be substituted by C$_1$-C$_4$-alkyl, fluoro, chloro, bromo, cyano, nitro or trifluoromethyl, $R^5$ represents methyl, $R^6$ represents hydrogen, $C_1$-$C_4$-alkyl, mono- or di-$C_1$-$C_4$-alkylaminocarbonyl, $C_1$-$C_4$-alkylcarbonyl or $C_1$-$C_4$-alkoxycarbonyl, wherein $C_1$-$C_4$-alkyl and $C_1$-$C_4$-alkoxycarbonyl can be substituted with a radical selected from the group consisting of hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, amino, mono- and di-$C_1$-$C_4$-alkylamino, or $R^6$ represents a moiety of the formula

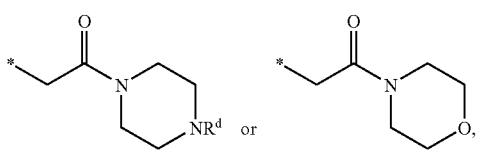

wherein
$R^d$ is selected from the group consisting of hydrogen and methyl, or $R^6$ represents a group of the formula -T-U wherein
T represents a —$CH_2$— group
and
U represents
phenyl, furyl or oxazolyl each of which is substituted by one or two radicals independently selected from the group consisting of fluoro, chloro, bromo, $C_1$-$C_4$-alkyl and a group of the formula —V—W wherein V represents a bond, a —$CH_2$— group or a —CH=CH— group, and W represents $C_1$-$C_4$-alkoxycarbonyl or hydroxycarbonyl, a group of the formula —C(=O)—NH—$SO_2$—$R^f$ wherein $R^f$ represents $C_1$-$C_4$-alkyl which can be substituted by trifluoromethyl, or $R^f$ represents phenyl which can be substituted by $C_1$-$C_4$-alkyl, fluoro, chloro, bromo, cyano, nitro or trifluoromethyl, or a group of the formula —C(=O)—$NHR^h$ wherein $R^h$ represents phenyl which can be substituted by $C_1$-$C_4$-alkoxycarbonyl or hydroxycarbonyl, or $R^6$ represents
$C_3$-$C_6$-cycloalkyl which can be substituted by $C_1$-$C_4$-alkoxycarbonyl or hydroxycarbonyl, or a —CH=CH— group which is substituted by $C_1$-$C_4$-alkoxycarbonyl or hydroxycarbonyl, $R^7$ represents trifluoromethyl or nitro, and $Y^1$, $Y^2$, $Y^3$, $Y^4$ and $Y^5$ each represent CH.

In another likewise preferred embodiment, the present invention relates to compounds according to general formula (I), wherein A is phenyl or pyridyl.

In another likewise preferred embodiment, the present invention relates to compounds according to general formula (I), wherein $R^1$ is hydrogen.

In another likewise preferred embodiment, the present invention relates to compounds according to general formula (I), wherein $R^2$ is cyano, especially wherein A is phenyl or pyridyl and $R^2$ is cyano located in para-position relative to the central dihydropyrimidinone ring.

In another likewise preferred embodiment, the present invention relates to compounds according to general formula (I), wherein $R^3$ is hydrogen.

In another likewise preferred embodiment, the present invention relates to compounds according to general formula (I), wherein $R^5$ is methyl.

In another likewise preferred embodiment, the present invention relates to compounds according to general formula (I), wherein $R^7$ is trifluoromethyl or nitro, especially wherein $R^7$ is trifluoromethyl located in meta-position relative to the central dihydropyrimidinone ring.

In another likewise particularly preferred embodiment, the present invention relates to compounds of general formula (IA)

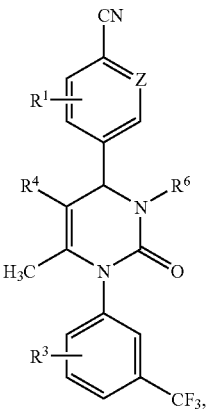

(IA)

wherein

Z represents CH or N, and $R^1$, $R^3$, $R^4$ and $R^6$ have the meaning indicated above.

The compounds of the present invention, wherein $R^6$ is hydrogen, can enolize into the corresponding hydroxyamidines:

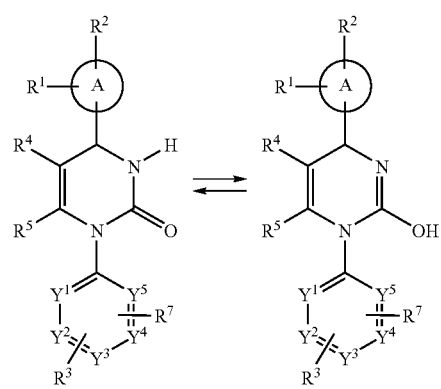

In another embodiment, the present invention relates to a process for synthesizing the compounds of general formula (I) or (IA), respectively.

The compounds of general formula (I) or (IA), respectively, can be synthesized by condensing compounds of general formula (II)

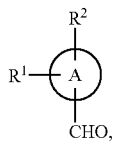
(II)

wherein A, $R^1$ and $R^2$ have the meaning indicated above, with compounds of general formula (III)

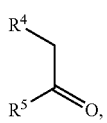
(III)

wherein $R^4$ and $R^5$ have the meaning indicated above, and compounds of general formula (IV)

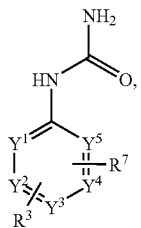
(IV)

wherein $R^3$, $R^7$, and $Y^1$ to $Y^5$ have the meaning indicated above,
in the presence of an acid or acid anhydride either in a three-component/one-step reaction or sequentially to give compounds of general formula (IB)

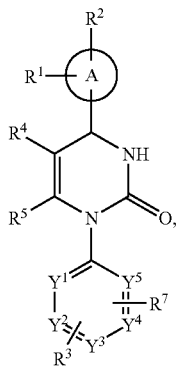
(IB)

wherein A, $R^1$ to $R^5$, $R^7$, and $Y^1$ to $Y^5$ have the meaning indicated above,
optionally followed, in case $R^6$ does not represent hydrogen, by reaction of the compounds of general formula (IB) with compounds of general formula (V)

$$R^{6*}—X \quad\quad (V),$$

wherein
$R^{6*}$ has the meaning of $R^6$ as indicated above, but does not represent hydrogen, and
X represents a leaving group, such as halogen, tosylate, mesylate or sulfate,
in the presence of a base.

Suitable solvents for the process (II)+(III)+(IV)→(IB) are generally customary organic solvents which do not change under the reaction conditions. These include ethers such as diethyl ether, diisopropyl ether, methyl t-butyl ether, 1,2-dimethoxyethane, dioxan or tetrahydrofuran, ethyl acetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is tetrahydrofuran or dioxan.

Suitable acids for the process (II)+(III)+(IV)→(IB) are generally inorganic or organic acids or acid anhydrides. These preferably include carboxylic acids, such as, for example, acetic acid or trifluoroacetic acid, sulfonic acids, such as, for example, methanesulfonic acid or p-toluenesulfonic acid, hydrochloric acid, phosphoric or phosphonic acids or anhydrides, such as polyphosphoric acid or propanephosphonic acid anhydride. Preference is given to polyphosphoric acid ethyl ester. The acid is employed in an amount from 0.25 mol to 100 mol, relative to 1 mol of the compound of the general formula (III).

The process is in general carried out in a temperature range from +20° C. to +150° C., preferably from +60° C. to +100° C.

The process is generally carried out at normal pressure. However, it is also possible to carry it out at elevated pressure or at reduced pressure (for example in a range from 0.5 to 5 bar).

Suitable solvents for the process (IB)+(V)→(I) are generally customary organic solvents which do not change under the reaction conditions. These include ethers such as diethyl ether, diisopropyl ether, 1,2-dimethoxyethane, dioxan or tetrahydrofuran, ethyl acetate, acetone, acetonitrile, dimethylsulfoxide, dimethylformamide, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is tetrahydrofuran or dimethylformamide.

Suitable bases for the process (IB)+(V)→(I) are generally inorganic or organic bases. These preferably include alkali carbonates such as sodium or potassium carbonate or hydrogencarbonate, cyclic amines such as, for example, N-methylmorpholine, N-methylpiperidine, pyridine or 4-N,N-dimethylaminopyridine, or ($C_1$-$C_4$)-trialkylamines such as, for example, triethylamine or diisopropylethylamine, or alkali hydrides such as sodium or potassium hydride. Preference is given to potassium carbonate or sodium hydride. The base is employed in an amount from 0.1 mol to 10 mol, preferably from 1 mol to 3 mol, relative to 1 mol of the compound of general formula (IV).

The process is in general carried out in a temperature range from 0° C. to +150° C., preferably from +20° C. to +80° C., especially at room temperature.

The process is generally carried out at normal pressure. However, it is also possible to carry it out at elevated pressure or at reduced pressure (for example in a range from 0.5 to 5 bar).

The compounds of the general formulas (II), (III), (IV) and (V) are known per se, or they can be prepared by customary methods.

The compounds of the present invention can also be prepared, if appropriate, by functional group transformations of individual substituents, especially those listed under $R^4$ and $R^6$, of the compounds of general formula (I) obtained by the process described above. These transformations are carried out using standard synthetic methods, e.g. by esterification, ester cleavage/hydrolysis, amide formation, catalytic hydrogenation, alkylation and/or aryl coupling reactions.

The above-mentioned method can be illustrated by the following scheme:

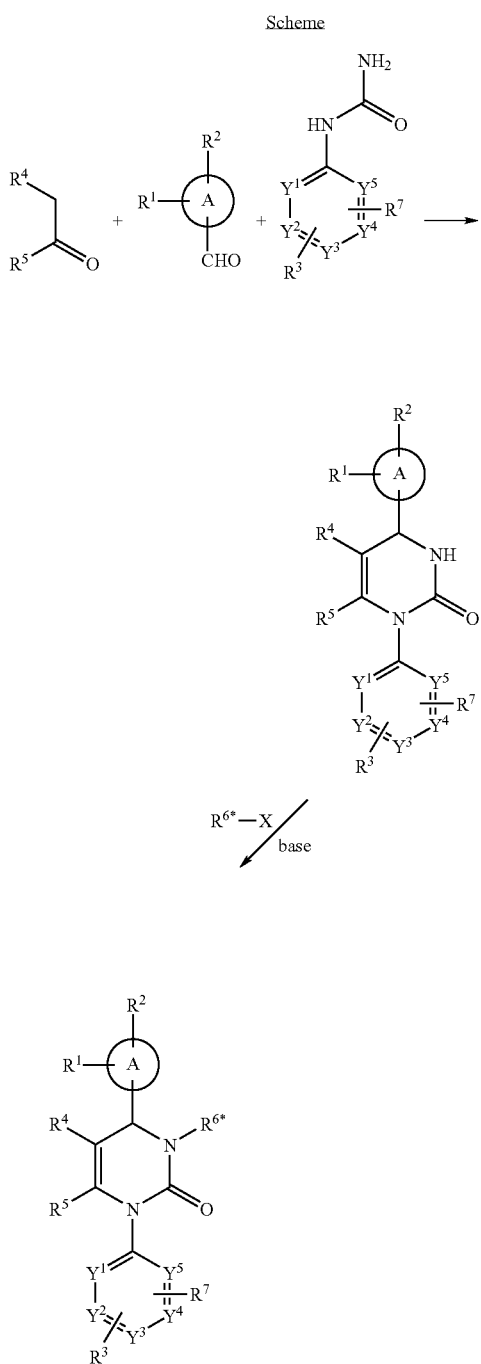

Scheme

The compounds according to the invention exhibit an unforeseeable, useful pharmacological and pharmacokinetic activity spectrum. They are therefore suitable for use as medicaments for the treatment and/or prophylaxis of disorders in humans and animals.

Surprisingly, the compounds of the present invention show human neutrophil elastase (HNE) inhibitory activity and are therefore suitable for the preparation of medicaments for the treatment of diseases associated with HNE activity. They may thus provide an effective treatment of acute and chronic inflammatory processes, such as rheumatoid arthritis, atherosclerosis, and especially of acute and chronic pulmonary diseases, such as lung fibrosis, cystic fibrosis, pneumonia, acute respiratory distress syndrome (ARDS), in particular pulmonary emphysema, including smoking-induced emphysema, and chronic obstructive pulmonary diseases (COPD), chronic bronchitis and bronchiectasis. The compounds of the present invention may further provide an effective treatment for cardiovascular ischaemic diseases such as acute coronary syndrome, acute myocardial infarction, unstable and stable angina pectoris, coronary artery bypass grafts (CABG) and heart failure development, for atherosclerosis, mitral valvular disease, atrial septal defects, percutaneous transluminal coronary angioplasty (PTCA), inflammation after open heart surgery and for pulmonary hypertension. They may also prove useful for an effective treatment of rheumatoid arthritis, acute inflammatory arthritis, cancer, acute pancreatitis, ulcerative colitis, periodontal disease, Chury-Strauss syndrome, acute and chronic atopic dermatitis, psoriasis, systemic lupus erythematosus, bullous pemphigus, sepsis, alcoholic hepatitis, liver fibrosis, Behcet's disease, allergic fungal sinusitis, allergic sinusitis, Crohn's disease, Kawasaki disease, glomerulonephritis, acute pyelonephritis, colorectal diseases, chronic suppurative otitis media, chronic venous leg ulcers, inflammatory bowel disease, bacterial and viral infections, brain trauma, stroke and other conditions in which neutrophil participation is involved.

The present invention further provides medicaments containing at least one compound according to the invention, preferably together with one or more pharmacologically safe excipient or carrier substances, and also their use for the above-mentioned purposes.

The active component can act systemically and/or locally. For this purpose, it can be applied in a suitable manner, for example orally, parenterally, pulmonally, nasally, sublingually, lingually, buccally, rectally, transdermally, conjunctivally, otically or as an implant.

For these application routes, the active component can be administered in suitable application forms.

Useful oral application forms include application forms which release the active component rapidly and/or in modified form, such as for example tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include for example inhalatory pharmaceutical forms (including powder inhalers, nebulizers), nasal drops/solutions, sprays; tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders or implants.

The active components can be converted into the recited application forms in a manner known per se. This is carried out using inert non-toxic, pharmaceutically suitable excipients. These include inter alia carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

For human use, in the case of oral administration, it is recommendable to administer doses of from 0.001 to 50 mg/kg, preferably of 0.01 mg/kg to 20 mg/kg. In the case of parenteral administration, such as, for example, intravenously or via mucous membranes nasally, buccally or inhalationally, it is recommendable to use doses of 0.001 mg/kg to 0.5 mg/kg.

In spite of this, it can be necessary in certain circumstances to depart from the amounts mentioned, namely as a function of body weight, application route, individual behaviour towards the active component, manner of preparation and time or interval at which application takes place. It can for instance be sufficient in some cases to use less than the aforementioned minimum amount, while in other cases the upper limit mentioned will have to be exceeded. In the case of the application of larger amounts, it can be advisable to divide them into a plurality of individual doses spread through the day.

The percentages in the tests and examples which follows are, unless otherwise stated, by weight; parts are by weight. Solvent ratios, dilution ratios and concentrations reported for liquid/liquid solutions are each based on the volume.

Evaluation of Physiological Activity

The potential of the compounds of the invention to inhibit neutrophil elastase activity may be demonstrated, for example, using the following assays:

I. In vitro Enzyme Assays of Human Neutrophil Elastase (HNE)

Assay Contents:

assay buffer: 0.1 M HEPES-NaOH buffer pH 7.4, 0.5 M NaCl, 0.1% (w/v) bovine serum albumin;

suitable concentration (see below) of HNE (18 U/mg lyophil, #20927.01, SERVA Electrophoresis GmbH, Heidelberg, Germany) in assay buffer;

suitable concentration (see below) of substrate in assay buffer;

suitable concentration of test compounds diluted with assay buffer from a 10 mM stock solution in DMSO.

Example I-A

In vitro Inhibition of HNE Using a Fluorogenic Peptide Substrate (Continuous Read-out Signal, 384 MTP Assay Format):

In this protocol, the elastase substrate MeOSuc-Ala-Ala-Pro-Val-AMC (#324740, Calbiochem-Novabiochem Corporation, Merck KGaA, Darmstadt, Germany) is used. The test solution is prepared by mixing 10 µl of test compound dilution, 20 µl of HNE enzyme dilution (final concentration 8-0.4 µU/ml, routinely 2.1 µU/ml) and 20 µl of substrate dilution (final concentration 1 mM-1 µM, routinely 20 µM), respectively. The solution is incubated for 0-2 hrs at 37° C. (routinely one hour). The fluorescence of the liberated AMC due to the enzymatic reaction is measured at 37° C. (TECAN spectra fluor plus plate reader). The rate of increase of the fluorescence (ex. 395 nm, em. 460 nm) is proportional to elastase activity. $IC_{50}$ values are determined by RFU-versus-[I] plots. $K_m$ and $K_{m(app.)}$ values are determined by Lineweaver-Burk plots and converted to $K_i$ values by Dixon plots.

The preparation examples have $IC_{50}$ values within the range of 5 nM-5 µM in this assay. Representative data are given in Table 1:

TABLE 1

| Example No. | $IC_{50}$ [nM] |
|---|---|
| 1 | 20 |
| 5 | 5 |
| 6 | 200 |
| 14 | 1000 |
| 21 | 130 |
| 43 | 23 |
| 45 | 20 |
| 69 | 50 |
| 73 | 1000 |
| 78 | 50 |

Example I-B

In vitro Inhibition of HNE Using a Fluorogenic, Unsoluble Elastin Substrate (Discontinuous Read-out Signal, 96 MTP Assay Format):

In this protocol the elastase substrate elastin-fluorescein (#100620, ICN Biomedicals GmbH, Eschwege, Germany) is used. The test solution is prepared by mixing 3 µl of test compound dilution, 77 µl of HNE enzyme dilution (final concentration 0.22 U/ml-2.2 mU/ml, routinely 21.7 µU/ml) and 80 µl substrate suspension (final concentration 2 mg/ml). The suspension is incubated for 0-16 hrs at 37° C. (routinely four hours) under slightly shaking conditions. To stop the enzymatic reaction, 160 µl of 0.1 M acetic acid are added to the test solution (final concentration 50 mM). The polymeric elastin-fluorescein is pulled down by centrifugation (Eppendorf 5804 centrifuge, 3.000 rpm, 10 min). The supernatant is transferred into a new MTP and the fluorescence of the liberated peptide fluorescein due to the enzymatic reaction is measured (BMG Fluostar plate reader). The rate of fluorescence (ex. 490 nm, em. 520 nm) is proportional to elastase activity. $IC_{50}$ values are determined by RFU-versus-[I] plots.

II. In vitro Human Neutrophil Assays

Example II-A

In vitro PMN Elastolysis Assay

This assay is used to determine the elastolytic potential of human polymorphonuclear cells (PMNs) and assess the proportion of degradation due to neutrophil elastase [cf. Z. W. She et al., Am. J. Respir. Cell. Mol. Biol. 9, 386-392 (1993)].

Tritiated elastin, in suspension, is coated on to a 96 well plate at 10 µg per well. Test and reference [ZD-0892 (J. Med. Chem. 40, 1876-1885, 3173-3181 (1997), WO 95/21855) and α1 protease inhibitor (α1PI)] compounds are added to the wells at the appropriate concentrations. Human PMNs are separated from peripheral venous blood of healthy donors and resuspended in culture media. The neutrophils are added to the coated wells at concentrations ranging between $1\times10^6$ to $1\times10^5$ cells per well. Porcine pancreatic elastase (1.3 µM)

is used as a positive control for the assay, and α1PI (1.2 μM) is used as the positive inhibitor of neutrophil elastase. The cellular control is PMNs without compound at each appropriate cell density. The cells plus compounds are incubated in a humidified incubator at 37° C. for 4 hours. The plates are centrifuged to allow the harvest of cell supernatant only. The supernatant is transferred in 75 μl volumes to corresponding wells of a 96 well Lumaplate™ (solid scintillant containing plates). The plates are dried until no liquid is visible in the wells and read in a beta counter for 3 minutes per well.

Elastolysis of the $^3$H-elastin results in an increase in counts in the supernatant. An inhibition of this elastolysis shows a decrease, from the cellular control, of tritium in the supernatant. α1PI gave 83.46±3.97% (mean±s.e.m.) inhibition at 1.2 μM (n=3 different donors at $3.6 \times 10^5$ cells per well). $IC_{50}$ values were obtained for the reference compound ZD-0892 of 45.50±7.75 nM (mean±s.e.m.) (n=2 different donors at $3.6 \times 10^5$ cells per well).

Given that ZD-0892 is a selective inhibitor of PMN elastase along with the data from α1PI inhibition, these results indicate that the majority of elastin degradation by PMNs is due to the release of neutrophil elastase, and not to another elastolytic enzyme such as matrix metalloproteases (MMPs). The compounds of this invention are evaluated for their inhibitory activity in this HNE-dependent model of neutrophil elastolysis.

Example II-B

In Vitro Inhibition of Membrane Bound Elastase

Measurement of the inhibition of elastase bound to neutrophil membranes is performed using a human neutrophil assay. Neutrophils are stimulated with LPS at 37° C. for 35 min and then spun at 1600 rpm. Subsequently, the membrane bound elastase is fixed to the neutrophils with 3% paraformaldehyde and 0.25% glutaraldehyde for 3 min at 4° C. The neutrophils are then spun, and vehicle and the compound under evaluation are added, followed by addition of the substrate MeO-Suc-Ala-Ala-Pro-Val-AMC (#324740, Calbiochem-Novabiochem Corporation, Merck KGaA, Darmstadt, Germany) at 200 μM. Following a 25 min incubation at 37° C., the reaction is terminated with PMSF (phenylmethanesulfonyl fluoride), and the fluorescence is read at ex: 400 nm and em: 505 nm. $IC_{50}$ values are determined by interpolation from plots of relative fluorescence vs. inhibitor concentration.

III. In vivo Models

Example III-A

In Vivo Model of Acute Lung Injury in the Rat

Instillation of human neutrophil elastase (HNE) into rat lung causes acute lung damage. The extent of this injury can be assessed by measuring lung haemorrhage.

Rats are anaesthetised with Hypnorm/Hypnovel/water and instilled with HNE or saline delivered by microsprayer into the lungs. Test compounds are administered by intravenous injection, by oral gavage or by inhalation at set times prior to the administration of HNE. Sixty minutes after the administration of elastase animals are killed by an anaesthetic overdose (sodium pentobarbitone) and the lungs lavaged with 2 ml heparinised phosphate buffered saline (PBS). Bronchoalveolar lavage (BAL) volume is recorded and the samples kept on ice. Each BAL sample is centrifuged at 900 r.p.m. for 10 minutes at 4-10° C. The supernatant is discarded and the cell pellet resuspended in PBS and the sample spun down again. The supernatant is again discarded and the cell pellet resuspended in 1 ml 0.1% cetyltrimethyl-ammonium bromide (CTAB/PBS to lyse the cells. Samples are frozen until blood content is assayed. Prior to the haemorrhage assay the samples are defrosted and mixed. 100 μl of each sample are placed into a separate well of a 96 well flat-bottomed plate. All samples are tested in duplicate. 100 μl 0.1% CTAB/PBS is included as a blank. The absorbance of the well contents is measured at 415 nm using a spectrophotometer. A standard curve is constructed by measuring the OD at 415 nm of different concentrations of blood in 0.1% CTAB/PBS. Blood content values are calculated by comparison to the standard curve (included in each plate) and normalised for the volume of BAL fluid retrieved.

The compounds of this invention are evaluated intravenously, orally or by inhalation for their inhibitory activity in this model of HNE-induced haemorrhage in the rat.

Example III-B

In Vivo Model of Acute Myocardial Infarction in the Rat

Elastase inhibitors are tested in a rat thread infarct model. Male Wistar rats (weighing >300 g) receive 10 mg/kg aspirin 30 min prior to surgery. They are anaesthetized by isofluran and ventilated (120-130 strokes/min, 200-250 μl stroke volume; MiniVent Type 845, Hugo Sachs Elektronik, Germany) during the whole surgery. Following a left thoracotomy at the fourth inter-costal space, the pericardium is opened and the heart briefly exteriorized. A thread is turned around the left coronary artery (LAD) without occluding the artery. The thread is passed under the skin to the neck of the animal. The thorax is closed and the animal is allowed to recover for 4 days. At the fifth day, rats are anaesthetized with ether for 3 min, and the thread is tied and the LAD occluded under ECG control. Test compounds are administered before or after LAD occlusion per os, intraperitoneally or intravenously (bolus or permanent infusion). After 1 hr occlusion, the thread is reopened to allow reperfusion. Hearts are excised, and infarct sizes are determined 48 hours later by staining of the re-occluded hearts with Evans blue, followed by TTC (triphenyltetrazolium chloride) staining of 2 mm heart sections. Normoxic (not occluded tissue) areas stain blue, ischemic (occluded but surviving tissue) areas stain red and necrotic (occluded dead tissue) areas remain white. Each tissue section is scanned and infarct sizes are determined by computer planimetry.

B. EXAMPLES

Abbreviations aq. aqueous
c concentration
conc. concentrated
DMF N,N-dimethylformamide
DMSO dimethylsulfoxide
EI electron impact ionisation (for MS)
ESI electro-spray ionisation (for MS)
h hour(s)
HPLC high pressure liquid chromatography
LC-MS liquid chromatography coupled with mass spectroscopy
min minute(s)
Mp. melting point
MS mass spectroscopy NMR nuclear magnetic resonance spectroscopy
of th. of theoretical (yield)
RP reverse phase (for HPLC)
$R_t$ retention time (for HPLC)
THF tetrahydrofuran General Methods:

All reactions are carried out under an argon atmosphere unless otherwise noted. Solvents are used as purchased from Aldrich without further purification. 'Silica gel' or 'Silica' refers to Silica gel 60 (0.040 mm-0.063 mm) from Merck KGaA company. Melting points are obtained with a Büchi 512 or similar melting point device and are uncorrected.

Compounds purified by preparative HPLC are purified over a RP18-column with acetonitrile and water as the eluent, using a 1:9 to 9:1 gradient.

LC-MS/HPLC Methods:

HPLC Method 1

Instrument: HP 1100 with DAD detection; column: Kromasil RP-18, 60 mm×2 mm, 3.5 µm; eluent A: 5 ml $HClO_4$/l water, eluent B: acetonitrile; gradient: 0 min 2% B→0.5 min 2% B→4.5 min 90% B→9 min 90% B; flow: 0.75 ml/min; oven: 30° C.; UV detection: 210 nm.

LC-MS Method 2

Instrument: Micromass Quattro LCZ with HPLC Agilent Series 1100; column: Grom-Sil120 ODS-4HE, 50 mm×2.0 mm, 3 µm; eluent A: 1 l water+1 ml 50% formic acid, eluent B: 1 l acetonitrile+1 ml 50% formic acid; gradient: 0.0 min 100% A→0.2 min 100% A→2.9 min 30% A→3.1 min 10% A→4.5 min 10% A; oven: 55° C.; flow: 0.8 ml/min; UV detection: 208-400 nm.

LC-MS Method 3

Instrument MS: Micromass ZQ; Instrument HPLC: Waters Alliance 2795; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min 2.5 min/3.0 min/ 4.5 min 2 ml/min; oven: 50° C.; UV detection: 210 nm.

HPLC Method 4

Instrument MS: Micromass ZQ; Instrument HPLC: HP 1100 Series with DAD detection; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; oven: 50° C.; UV detection: 210 nm.

LC-MS Method 5

Instrument: Micromass Quattro LCZ with HPLC Agilent Series 1100; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; oven: 50° C.; UV detection: 208-400 nm.

HPLC Method 6

Instrument: HP 1100 with DAD detection; column: Kromasil RP-18, 60 mm×2 mm, 3.5 µm; eluent A: 5 ml $HClO_4$/l water, eluent B: acetonitrile; gradient: 0 min 2% B→0.5 min 2% B→4.5 min 90% B→6.5 min 90% B; flow: 0.75 ml/min; oven: 30° C.; UV detection: 210 nm.

Starting Materials and Intermediates:

Example 1A

Ethyl 4-(4-cyanophenyl)-6-methyl-2-oxo-1-[3-(trifluoromethyl)phenyl]-1,2,3,4-tetrahydro-5-pyrimidinecarboxylate

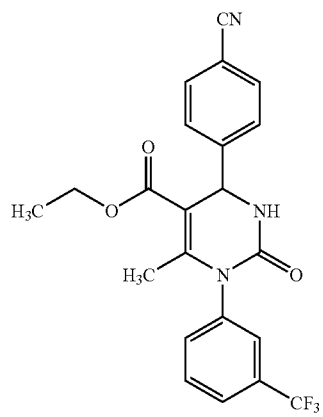

7.0 g (34.29 mmol) N-[3-(trifluoromethyl)phenyl]urea, 8.99 g (68.58 mmol) 4-cyanobenzaldehyde, 8.92 g (68.58 mmol) ethyl 3-oxobutanoate and 20 g polyphosphoric acid ethyl ester are suspended in 250 ml of tetrahydrofuran. The mixture is stirred at reflux for 18 hours. After cooling down to room temperature, the solvent is removed in vacuo and the residue is purified by column chromatography on silica with cyclohexane/ethyl acetate as eluent.

Yield: 13.4 g (91% of th.)

$^1$H-NMR (200 MHz, DMSO-$d_6$): δ=1.1 (t, 3H), 2.0 (s, 3H), 4.0 (q, 2H), 5.4 (d, 1H), 7.6 (m, 3H), 7.7 (m, 3H), 7.9 (m, 2H), 8.4 (d, 1H) ppm.

Example 2A

Allyl 4-(4-cyanophenyl)-6-methyl-2-oxo-1-[3-(trifluoromethyl)phenyl]-1,2,3,4-tetrahydropyrimidine-5-carboxylate

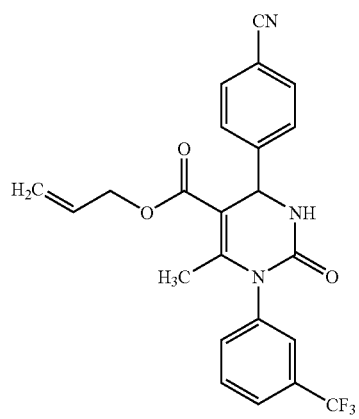

45.0 g ethyl polyphosphate are dissolved in 150 ml dioxane, 15.0 g (73.5 mmol) N-[3-(trifluoromethyl)phenyl]urea, 19.3 g (147 mmol) 4-cyanobenzaldehyde and 20.9 g (147 mmol) allyl acetoacetate are added and the mixture is stirred under reflux overnight. Volatiles are evaporated in vacuo, the remainder is dissolved in ethyl acetate and sequentially washed with saturated aqueous sodium hydrogencarbonate, sodium hydrogensulfite and sodium chloride solution. The organic phase is dried over magnesium sulfate, filtered and evaporated to dryness in vacuo. The crude product is purified by column chromatography on silica gel (eluent: cyclohexane/ethyl acetate).

Yield: 18.4 g (50% of th.)

$^1$H-NMR (400 MHz, DMSO-$d_6$): δ=2.08 (s, 3H), 4.55 (d, 2H), 5.05-5.18 (m, 2H), 5.41 (d, 1H), 5.82 (dddd, 1H), 7.54-7.92 (m, 8H), 8.41 (d, 1H) ppm.

Example 3A

Allyl (4R)-4-(4-cyanophenyl)-6-methyl-2-oxo-1-[3-(trifluoromethyl)phenyl]-1,2,3,4-tetrahydropyrimidine-5-carboxylate

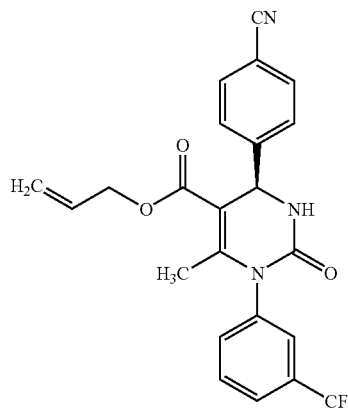

The enantiomers of Example 2A are separated by preparative HPLC on a chiral phase [chiral silica gel selector based on monomer N-methacryloyl-L-leucine-1-menthylamide, cf. EP-A-379 917; 250 mm×20 mm; eluent: ethyl acetate→methanol→ethyl acetate; flow 50 ml/min; temperature 24° C.; detection 280 nm].

$^1$H-NMR (400 MHz, DMSO-$d_6$): δ=2.08 (s, 3H), 4.55 (d, 2H), 5.05-5.18 (m, 2H), 5.41 (d, 1H), 5.82 (dddd, 1H), 7.54-7.92 (m, 8H), 8.41 (d, 1H) ppm.

$[α]^{20}$=+25.9° (λ=589 nm, methanol, c=540 mg/100 ml).

Example 4A

4-{5-Acetyl-6-methyl-2-oxo-1-[3-(trifluoromethyl)phenyl]-1,2,3,4-tetrahydro-4-pyrimidinyl}benzonitrile

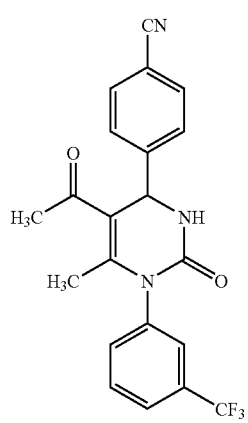

30 g (147 mmol) N-[3-(trifluoromethyl)phenyl]urea, 19.3 g (147 mmol) 4-cyanobenzaldehyde and 14.7 g (147 mmol) 2,4-pentanedione are suspended in 300 ml of tetrahydrofuran, and 90 g polyphosphoric acid ethyl ester are added. The mixture is stirred at reflux for 4 hours. After cooling down to room temperature, the solvent is removed in vacuo, the remainder is dissolved in ethyl acetate and sequentially washed with saturated aqueous sodium hydrogencarbonate and sodium chloride solution. The organic phase is dried over magnesium sulfate, filtered and evaporated to dryness in vacuo. The crude product is purified by column chromatography over silica gel (eluent: cyclohexane/ethyl acetate).

Yield: 16.8 g (29% of th.)

$^1$H-NMR (200 MHz, DMSO-$d_6$): δ=2.0 (s, 3H), 2.2 (s, 3H), 5.5 (d, 1H), 7.5 (m, 1H), 7.6 (m, 3H), 7.7 (m, 1H), 7.8 (m, 1H), 7.9 (m, 2H), 8.5 (d, 1H) ppm.

Example 5A 4-(4-Cyanophenyl)-6-methyl-2-oxo-1-[3-(trifluoromethyl)phenyl]-1,2,3,4-tetrahydro-5-pyrimidinecarboxylic acid

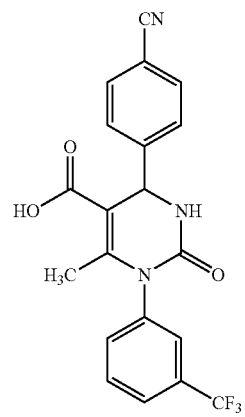

Method A:

3 g (7 mmol) of Example 1A are dissolved in a mixture of 50 ml water and 100 ml 5% potassium hydroxide in ethanol. The reaction mixture is stirred at room temperature for 18 hours. The solvent is removed in vacuo and the residue is purified by column chromatography on silica with dichloromethane/methanol as eluent.

Yield: 1.27 g (45% of th.)

$^{1}$H-NMR (300 MHz, DMSO-d$_{6}$): δ=2.0 (s, 3H), 5.4 (d, 1H), 7.6 (m, 1H), 7.6 (m, 2H), 7.7 (m, 1H), 7.8 (m, 1H), 7.9 (m, 3H), 8.3 (d, 1H), 12.5 (s, 1H) ppm.

Method B:

3.00 g (6.80 mmol) of Example 2A and 888 mg (10.2 mmol) morpholine are dissolved under argon in 30 ml tetrahydrofuran at room temperature. 392 mg (0.34 mmol) tetrakis(triphenylphosphine)-palladium(0) are added, and the mixture is reacted for 15 minutes at room temperature. The solvent is evaporated in vacuo, the remainder is dissolved in ethyl acetate and washed sequentially with 2 N hydrochloric acid, water and saturated sodium chloride solution. The organic phase is dried over magnesium sulfate and evaporated to dryness. The crude product is purified by preparative RP-HPLC with a water/acetonitrile gradient.

Yield: 1.51 g (52% of th.)

$^{1}$H-NMR: see above.

Example 6A (4R)-4-(4-Cyanophenyl)-6-methyl-2-oxo-1-[3-(trifluoromethyl)phenyl]-1,2,3,4-tetrahydro-5-pyrimidinecarboxylic acid

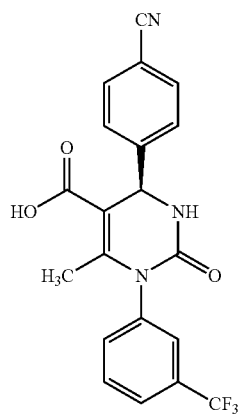

Method A:

The enantiomers of Example 5A are separated by preparative HPLC on a chiral phase [chiral silica gel selector based on monomer N-methacryloyl-L-leucine-1-menthylamide, cf EP-A-379 917; 250 mm×20 mm; eluent: ethyl acetate→methanol→ethyl acetate; flow 25 ml/min; temperature 23° C.; detection 254 nm].

$^{1}$H-NMR (300 MHz, DMSO-d$_{6}$): δ=2.0 (s, 3H), 5.4 (d, 1H), 7.6 (m, 1H), 7.6 (m, 2H), 7.7 (m, 2H), 7.8 (m, 1H), 7.9 (m, 2H), 8.3 (d, 1H), 12.5 (s, 1H) ppm.

[α]$^{20}$=+2.5° (λ=589 nm, methanol, c=505 mg/100 ml).

Method B:

In analogy to Example 5A (method B), this compound is prepared from Example 3A in 87% yield.

Example 7A

2-Hydroxyethyl (4R)-4-(4-cyanophenyl)-6-methyl-2-oxo-1-[3-(trifluoromethyl)phenyl]-1,2,3,4-tetrahydro-5-pyrimidinecarboxylate

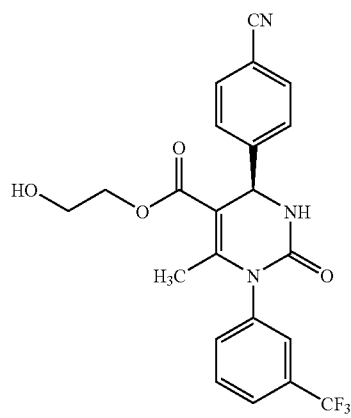

Under argon, 1560 mg (3.89 mmol) of Example 6A are added to 19.6 ml dimethylformamide. After addition of 1.095 ml (7.86 mmol) triethylamine and 1.11 ml (15.7 mmol) 2-bromoethanol, the reaction mixture is stirred at ca. 70° C. for 8 hours. After cooling to room temperature, the reaction mixture is concentrated in vacuo. The residue is taken up in ethyl acetate and washed with water. After drying with magnesium sulfate, the organic phase is evaporated in vacuo. The residue is taken up in 8 ml methanol and purified by preparative HPLC (column: Nucleosil 100-5 C18 Nautilus, 20×50 mm, 5 μm; solvent A: acetonitrile, solvent B: water+0.3% formic acid; gradient: 0 min 10% A→2 min 10% A→6 min 90% A→7 min 90% A→7.1 min 10% A→8 min 10% A; wavelength: 220 nm; injection volume: ca. 500 μl; number of injections: 18). The product containing fractions are combined and lyophilized.

Yield: 1290 mg (74.5% of th.)

MS (EI): m/z=446 (M+H)$^{+}$ $^{1}$H-NMR (300 MHz, DMSO-d$_{6}$): δ=2.05 (d, 3H), 3.5 (q, 2H), 3.95-4.15 (m, 2H), 4.75 (tr, 1H), 5.45 (d, 1H), 7.55-7.75 (m, 5H), 7.75 (d, 1H), 7.85 (d, 2H), 8.35 (d, 1H) ppm.

[α]$^{20}$=+14.3° (λ=589 nm, methanol, c=455 mg/100 ml).

Example 8A 5-(Benzyloxy)-hexane-2,4-dione

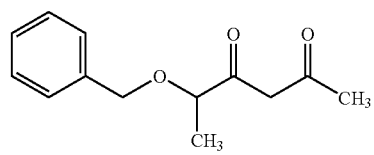

To a solution of ethyl 3-(benzyloxy)-2-methylpropanoate (13.4 g, 64 mmol) in dimethylsulfoxide (50 ml) is added sodium hydride (2.57 g, 64.34 mmol; 60% dispersion in mineral oil). After 5 minutes stirring, a solution of acetone (2.37 ml, 32.1 mmol) in dimethylsulfoxide (30 ml) is added, and the reaction is stirred at 60° C. overnight. After cooling to room temperature, saturated aqueous ammonium chloride (100 ml) is added and the product is extracted with ethyl acetate (3×150 ml). The combined organic phases are washed with brine, dried over anhydrous magnesium sulfate, filtered and concentrated. The residue is purified by flash chromatography over silica gel 60 (300 g) using cyclohexane/ethyl acetate (10:1 to 5:1) as eluent. The title compound is isolated as a mixture of enol ethers.

Yield: 4.92 g (69% of th.)

HPLC (method 1): $R_t$=4.17 min and 4.75 min, $\lambda_{max}$=280 nm

MS (ESIpos): m/z=220 (M+H)$^+$

Example 9A

1-Benzyl 2-ethyl piperidine-1,2-dicarboxylate

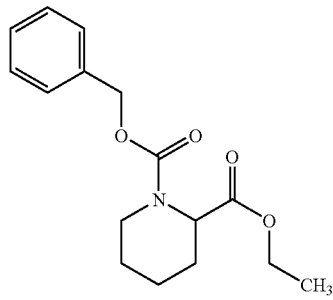

To a stirred solution of ethyl piperidine-2-carboxylate (15 g, 95 mmol), triethylamine (27 ml, 191 mmol) and 4-dimethylaminopyridine (0.58 g, 4.8 mmol) in dichloromethane (100 ml) at 0° C. is added a solution of benzyl chloridocarbonate (17 g, 100 mmol) dropwise. The reaction is allowed to warm slowly to room temperature. It is stirred at room temperature overnight (16 h), then allowed to stand for 2 days. The crude product is extracted with dichloromethane, washed with 1 N hydrochloric acid, saturated aqueous sodium bicarbonate solution and brine. The organic phase is dried with anhydrous magnesium sulfate, filtered and concentrated in vacuo. The residue is purified by flash chromatography over silica gel 60 (300 g) with cyclohexane/ethyl acetate as eluent to afford a pale yellow oil.

Yield: 17.9 g (62% of th.)
HPLC (method 6): $R_t$=4.91 min, $\lambda_{max}$=202 nm
MS (ESIpos): m/z=309 (M+NH$_4$)$^+$

Example 10A

Benzyl 2-acetoacetylpiperidine-1-carboxylate

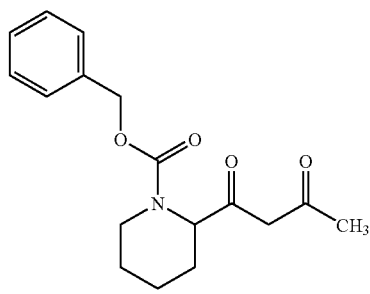

The title compound is prepared according to the procedure described in Example 8A and is isolated as the enol ether.

Yield: 2.13 g (82% of th.)
HPLC (method 1): $R_t$=4.45 and 4.98 min, $\lambda_{max}$=276 nm
MS (ESIpos): m/z=321 (M+NH$_4$)$^+$
$^1$H-NMR (300 MHz, CDCl$_3$): δ=15.4 (br s, 1H), 7.45-7.20 (m, 5H), 5.62-4.68 (m, 3H), 4.29-3.63 (m, 2H), 3.15-2.80 (m, 1H), 2.37-1.10 (m, 6H), 2.01 (s, 3H) ppm.

Example 11A 2-(Benzyloxy)-1-[(benzyloxy)methyl]ethyl 3-oxobutanoate

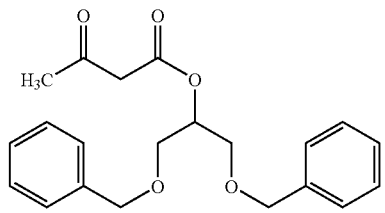

1.00 g (3.67 mmol) 1,3-dibenzyloxy-2-propanol is dissolved in 10 ml toluene, 3.72 mg (0.04 mmol) triethylamine are added, and the mixture is stirred at 90° C. 401 mg (4.77 mmol) diketene are added, and stirring is continued for 1 h. The mixture is cooled to room temperature, diluted with ice-water and extracted with toluene. The organic layer is dried over magnesium sulfate and evaporated to dryness. The crude product is purified by column chromatography on silica gel (eluent: cyclohexane/ethylacetate 2:1).

Yield: 1.03 g (69% of th.)

$^1$H-NMR (300 MHz, DMSO-d$_6$): δ=2.15 (s, 3H), 3.55-3.65 (m, 6H), 4.44 (dd, 2H), 5.67 (q, 1H), 7.23-7.40 (m, 10H) ppm.

Example 12A (1S)-2-(Benzyloxy)-1-methyl-2-oxoethyl 3-oxobutanoate

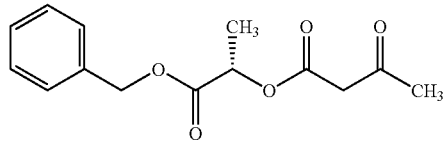

In analogy to the procedure of Example 11A, the title compound is synthesized using (S)-benzyl lactate with a yield of 80% of th.

$^1$H-NMR (200 MHz, DMSO-$d_6$): δ=1.42 (d, 3H), 2.18 (s, 3H), 3.66 (s, 2H), 5.11 (q, 1H), 5.17 (s, 2H), 7.30-7.43 (m, 5H) ppm.

Example 13A

Allyl 3-(2-tert.-butoxy-2-oxoethyl)-4-(4-cyanophenyl)-6-methyl-2-oxo-1-[3-(trifluoromethyl)phenyl]-1,2,3,4-tetrahydropyrimidine-5-carboxylate

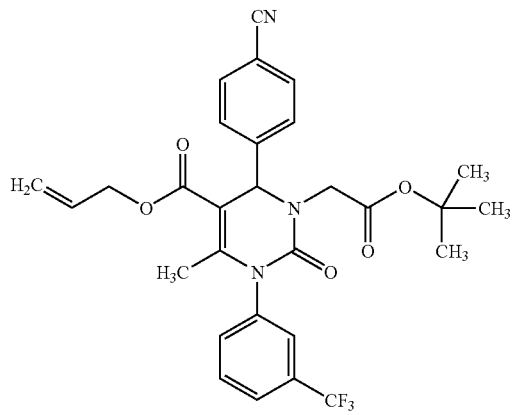

1000 mg (2.27 mmol) of Example 2A are dissolved in 10 ml dimethylformamide, 344 mg (2.49 mmol) potassium carbonate and 486 mg (2.49 mmol) tert.-butyl bromoacetate are added, and the suspension is stirred at room temperature overnight. The mixture is partitioned between ethyl acetate and aqueous potassium dihydrogenphosphate/disodium hydrogenphosphate buffer (pH 7). The combined organic extracts are washed with water and aqueous sodium chloride solution, dried over magnesium sulfate, and evaporated in vacuo. The crude product is purified by column chromatography on silica gel (eluent: cyclohexane/ethyl acetate 3:1).

Yield: 985 mg (78% of th.)

$^1$H-NMR (200 MHz, DMSO-$d_6$): δ=1.29 (s, 9H), 2.08 (s, 3H), 3.88 (d, 1H), 4.09 (d, 1H), 4.52 (d, 2H), 5.09-5.15 (m, 2H), 5.60 (s, 1H), 5.71-5.92 (m, 1H), 7.60-7.93 (m, 8H) ppm.

Example 14A 3-(2-tert.-Butoxy-2-oxoethyl)-4-(4-cyanophenyl)-6-methyl-2-oxo-1-[3-(trifluoromethyl)phenyl]-1,2,3,4-tetrahydropyrimidine-5-carboxylic acid

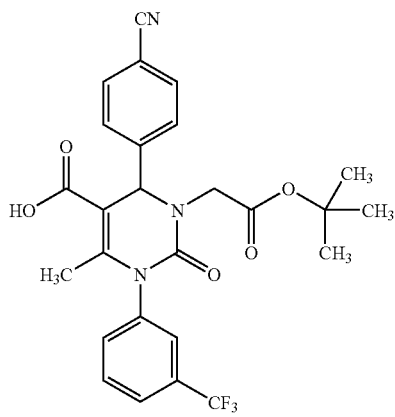

985 mg (1.77 mmol) of Example 13A and 231 mg (2.66 mmol) morpholine are dissolved in 10 ml tetrahydrofuran at room temperature under an argon atmosphere. 102 mg (0.09 mmol) tetrakis-(triphenylphosphine)palladium(0) are added, and the solution is stirred for 30 minutes. The solvent is evaporated in vacuo, the remainder is dissolved in ethyl acetate and washed with 2 M hydrochloric acid, water and aqueous sodium chloride solution, dried over magnesium sulfate and evaporated in vacuo. The crude product is purified using RP-HPLC with a water/acetonitrile gradient.

Yield: 662 mg (70% of th.)

$^1$H-NMR (200 MHz, DMSO-$d_6$): δ=1.30 (s, 9H), 2.05 (s, 3H), 3.85 (d, 1H), 4.09 (d, 1H), 5.55 (s, 1H), 7.57-7.90 (m, 8H), 12.6 (br s, 1H) ppm.

Example 15A tert.-Butyl [6-(4-cyanophenyl)-5-(1H-imidazol-1-ylcarbonyl)-4-methyl-2-oxo-3-[3-(trifluoromethyl)phenyl]-3,6-dihydropyrimidin-1(2H)-yl]acetate

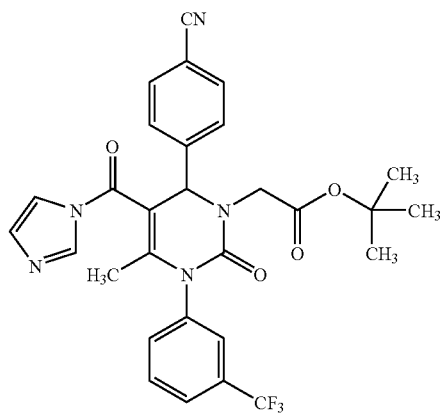

372 mg (0.72 mmol) of Example 14A are dissolved in 5 ml dimethylformamide, 351 mg (2.17 mmol) 1,1'-carbonyldiimidazole are added, and the mixture is stirred at room temperature overnight. The mixture is partitioned between water and ethyl acetate, the combined organic extracts are washed with aqueous sodium hydrogencarbonate solution, water and aqueous sodium chloride solution, dried over magnesium sulfate, filtered and evaporated to dryness in vacuo.

Yield: 392 mg (90% of th.)

$^1$H-NMR (300 MHz, DMSO-$d_6$): δ=1.30 (s, 9H), 1.48 (s, 3H), 3.83 (d, 1H), 4.05 (d, 1H), 5.65 (s, 1H), 7.05 (s, 1H), 7.62 (s, 1H), 7.68-7.90 (m, 7H), 7.98 (s, 1H), 8.37 (s, 1H) ppm.

Example 16A

4-{5-[(1H-1,2,3-Benzotriazol-1-yloxy)carbonyl]-6-methyl-2-oxo-1-[3-(trifluoromethyl)phenyl]-1,2,3,4-tetrahydropyrimidin-4-yl}benzonitrile

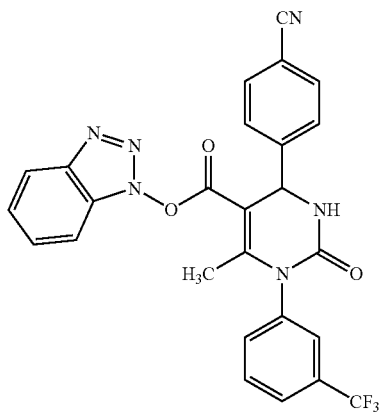

500 mg (1.25 mmol) of Example 5A, 310 mg (1.62 mmol) 1-ethyl-3-(3-(dimethylamino)propyl)carbodiimid-hydrochloride and 202 mg (1.49 mmol) 1-hydroxybenzotriazole are dissolved in 2 ml dimethylformamide and stirred at room temperature overnight. The reaction mixture is partitioned between ethyl acetate and water, the organic phase is washed with saturated sodium chloride solution, dried over magnesium sulfate and evaporated to dryness in vacuo. The crude product is used directly for further reactions.

Yield: 580 mg (76% of th.)

$^1$H-NMR (400 MHz, DMSO-$d_6$): δ=2.17 (s, 3H), 5.82 (d, 1H), 7.23 (d, 1H), 7.35-8.03 (m, 10H), 8.10 (d, 1H), 8.82 (d, 1H) ppm.

Example 17A

Tribenzyl 2-{4-(4-cyanophenyl)-6-methyl-2-oxo-1-[3-(trifluoromethyl)phenyl]-1,2,3,4-tetrahydropyrimidin-5-yl}ethane-1,1,1-tricarboxylate

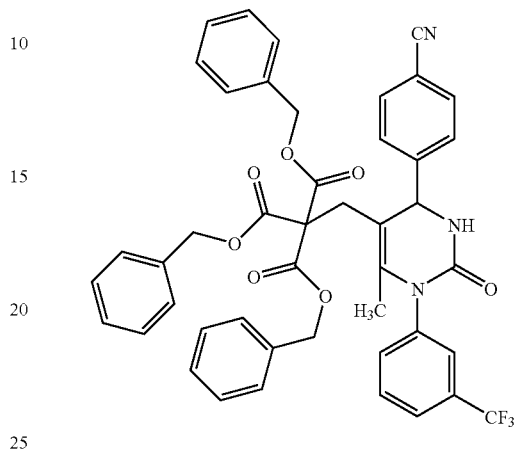

200 mg (0.52 mmol) of Example 1, 259 mg (0.62 mmol) tribenzyl methanetricarboxylate and 203 mg (0.77 mmol) triphenylphosphine are dissolved in 3 ml tetrahydrofuran under an argon atmosphere. The solution is cooled to 0° C., and 156 mg (0.77 mmol) diisopropyl azodicarboxylate are added slowly. The mixture is warmed to room temperature overnight, evaporated to dryness and purified directly by vacuum flash chromatography on silica (eluent: petrol ether/ethyl acetate 2:1→1:1) and thereafter by RP-HPLC (eluent: acetonitrile/water gradient).

Yield: 60 mg (14% of th.)

$^1$H-NMR (400 MHz, DMSO-$d_6$): δ=1.32 (s, 3H), 2.74 (d, 1H), 3.21 (d, 1H), 4.80 (d, 1H), 5.16 (s, 6H), 7.18-7.33 (m, 15H), 7.38 (d, 1H), 7.46 (s, 1H), 7.54 (d, 2H), 7.62 (t, 1H), 7.70 (d, 1H), 7.32-7.38 (m, 3H) ppm.

Example 18A (4R)-4-{5-Acetyl-6-methyl-2-oxo-1-[3-(trifluoromethyl)phenyl]-1,2,3,4-tetrahydro-4-pyrimidinyl}benzonitrile

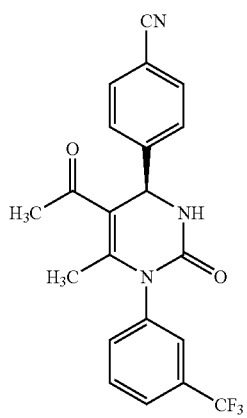

The enantiomers of Example 4A are separated by preparative HPLC on a chiral phase [chiral silica gel selector based on monomer N-methacryloyl-L-leucine-1-menthylamide, cf EP-A-379 917; 250 mm×20 mm; eluent: ethyl acetate→methanol→ethyl acetate; flow 25 ml/min; temperature 23° C.; detection 254 nm].

$^1$H-NMR (200 MHz, DMSO-d$_6$): δ=2.0 (s, 3H), 2.2 (s, 3H), 5.5 (d, 1H), 7.5 (m, 1H), 7.6 (m, 3H), 7.7 (m, 1H), 7.8 (m, 1H), 7.9 (m, 2H), 8.5 (d, 1H) ppm.

[α]$^{20}$=+45.9° (λ=589 nm, methanol, c=530 mg/100 ml).

Example 19A (4R)-Tribenzyl 2-{4-(4-cyanophenyl)-6-methyl-2-oxo-1-[3-(trifluoromethyl)phenyl]-1,2,3,4-tetrahydropyrimidin-5-yl}ethane-1,1,1-tricarboxylate

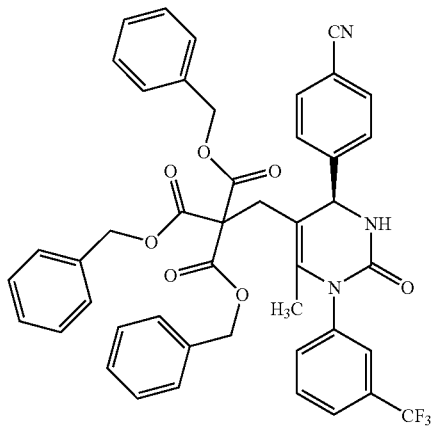

1.0 g (2.58 mmol) of Example 4, 1.3 g (3.10 mmol) tribenzyl methanetricarboxylate and 1.02 g (3.87 mmol) triphenylphosphine are dissolved in 15 ml tetrahydrofuran under an argon atmosphere. The solution is cooled to 0° C., and 0.67 g (3.87 mmol) diisopropyl azodicarboxylate are added slowly. The mixture is warmed to room temperature overnight, evaporated to dryness and purified directly by vacuum flash chromatography on silica (eluent: cyclohexane/ethyl acetate 2:1→1:1).

Yield: 0.65 mg (31% of th.)

$^1$H-NMR (400 MHz, DMSO-d$_6$): δ=1.3 (s, 3H), 2.7 (d, 1H), 3.2 (d, 1H), 4.8 (d, 1H), 5.2 (s, 6H), 7.2 (m, 6H), 7.3 (m, 9H), 7.4 (m, 1H), 7.5 (m, 1H), 7.5 (m, 2H), 7.6 (m, 1H), 7.7 (m, 1H), 7.8 (m, 3H) ppm.

Example 20A 1-(2,2-Dimethyl-1,3-dioxolan-4-yl)-butane-1,3-dione

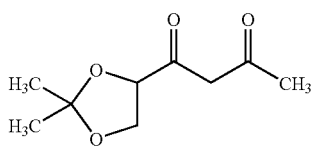

To sodium hydride (3.7 g, 93 mmol; 60% dispersion in mineral oil) under an argon atmosphere is added DMSO (30 ml) followed by a solution of methyl 2,2-dimethyl-1,3-dioxolane-4-carboxylate (15 g, 93 mmol) in DMSO (50 ml). A solution of acetone (2.7 g, 45 mmol) in DMSO (50 ml) is then added dropwise over 1 hour. The solution is stirred at room temperature for 16 h, then quenched with saturated aqueous ammonium chloride solution (350 ml) and extracted with diethyl ether (1 l). The ether layer is washed with brine, dried over anhydrous magnesium sulfate, filtered and concentrated in vacuo. The crude product is chromatographed over silica gel 60 with dichloromethane as eluent. The compound is isolated as its enol ether.

Yield: 3.98 g (46% of Th.)

$^1$H-NMR (300 MHz, CDCl$_3$): δ=5.90 (s, 1H), 4.56-4.44 (m, 1H), 4.32-4.23 (m, 1H), 4.04-3.96 (m, 1H), 2.11 (s, 3H), 1.49 (s, 3H), 1.41 (s, 3H) ppm.

PREPARATION EXAMPLES

Example 1

4-{5-(Hydroxymethyl)-6-methyl-2-oxo-1-[3-(trifluoromethyl)phenyl]-1,2,3,4-tetrahydropyrimidin-4-yl}benzonitrile

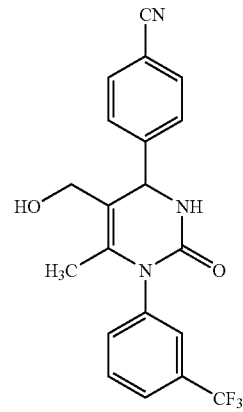

2.05 g (4.77 mmol) of Example 1A are dissolved in 40 ml tetrahydrofuran. At 0° C., 9.55 ml (9.55 mmol) of 1 M lithium aluminiumhydride in tetrahydrofuran are added dropwise. The solution is stirred at 0° C. for two hours and then quenched with methanol. The solvent is removed in vacuo and the residue is purified by column chromatography on silica with dichloromethane/methanol mixtures as eluent.

Yield: 1.08 g (58% of th.)

$^1$H-NMR (300 MHz, DMSO-d$_6$): δ=1.5 (s, 3H), 3.7 (dd, 1H), 4.1 (dd, 1H), 4.8 (dd, 1H), 5.1 (d, 1H), 7.5-7.7 (m, 6H), 7.9 (m, 3H) ppm.

Examples 2 and 3

4-{5-(1-Hydroxyethyl)-6-methyl-2-oxo-1-[3-(trifluoromethyl)phenyl]-1,2,3,4-tetrahydropyrimidin-4-yl}benzonitrile

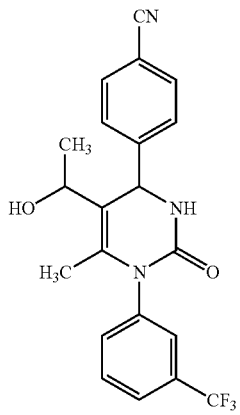

200 mg (0.5 mmol) of Example 4A and 49 mg (0.6 mmol) sodium acetate are dissolved in 5 ml ethanol. 47 mg (1.25 mmol) sodium borohydride are added. The solution is stirred at room temperature for 16 hours, then water is added. The product precipitates as mixture of diastereomers (94 mg). The diastereomers are separated by preparative HPLC.

Example 2
(Diastereomer I)

Yield: 52 mg (26% of th.)
$^1$H-NMR (300 MHz, DMSO-$d_6$): δ=0.8 (d, 3H), 1.6 (s, 3H), 4.6 (m, 1H), 4.9 (d, 1H), 5.1 (d, 1H), 7.5-7.7 (m, 6H), 7.8 (d, 1H), 7.9 (m, 2H) ppm.

Example 3
(Diastereomer II)

Yield: 41 mg (20% of th.)
$^1$H-NMR (300 MHz, DMSO-$d_6$): δ=1.2 (d, 3H), 1.6 (s, 3H), 4.6 (m, 2H), 4.9 (d, 1H), 7.5 (m, 2H), 7.6 (m, 4H), 7.8 (m, 2H), 7.9 (d, 1H) ppm.

Example 4

(4R)-4-{-5-(Hydroxymethyl)-6-methyl-2-oxo-1-[3-(trifluoromethyl)phenyl]-1,2,3,4-tetrahydropyrimidin-4-yl}benzonitrile

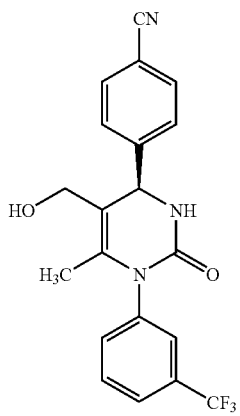

3.00 g (6.80 mmol) of Example 3A are dissolved in 20 ml dry tetrahydrofuran, 6.80 ml (6.80 mmol) of 1 M lithium aluminiumhydride in tetrahydrofuran are added slowly, and stirring is continued for 30 minutes at 0° C. Saturated ammonium chloride solution is added cautiously to hydrolyze excess of lithium aluminiumhydride, followed by 50 ml ethyl acetate and dropwise addition of water to precipitate inorganic salts. The organic phase is decanted, washed with water, dried over magnesium sulfate and evaporated to dryness. The crude product is purified by column chromatography over silica gel (eluent: dichloromethane/methanol 100:0→95:5).
Yield: 1.38 g (40% of th.)
$^1$H-NMR (200 MHz, DMSO-$d_6$): δ=1.55 (s, 3H), 3.67 (dd, 1H), 4.10 (dd, 1H), 4.77 (t, 1H), 5.09 (d, 1H), 7.50 (d, 1H), 7.55-7.75 (m, 5H), 7.82 (d, 1H), 7.87 (d, 2H) ppm.

Example 5

(4R)-[5-{[2-(Carboxymethoxy)ethoxy]carbonyl}-6-(4-cyanophenyl)-4-methyl-2-oxo-3-[3-(trifluoromethyl)phenyl]-3,6-dihydropyrimidin-1(2H)-yl]acetic acid

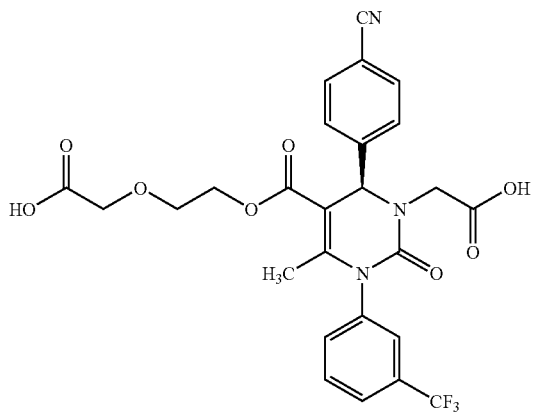

80 mg (0.18 mmol) of Example 7A are dissolved in 4 ml tetrahydrofuran, and 36 mg (0.9 mmol) sodium hydride (60% suspension in mineral oil) are added. After stirring for one hour at room temperature, 50 mg (0.36 mmol) bromoacetic acid are added. After stirring at room temperature for four hours, the mixture is quenched with methanol, the solvent is removed in vacuo and the residue is purified by preparative HPLC.
Yield: 21 mg (21% of th.)
$^1$H-NMR (300 MHz, DMSO-$d_6$): δ=2.0 (s, 3H), 2.9 (d, 1H), 3.5-3.7 (m, 3H), 4.0 (m, 2H), 4.3 (m, 2H), 5.9 (s, 1H), 7.6-7.7 (m, 6H), 7.8 (m, 3H) ppm.

Example 6

4-(4-Cyanophenyl)-N-cyclopropyl-6-methyl-2-oxo-1-[3-(trifluoromethyl)phenyl]-1,2,3,4-tetrahydropyrimidine-5-carboxamide

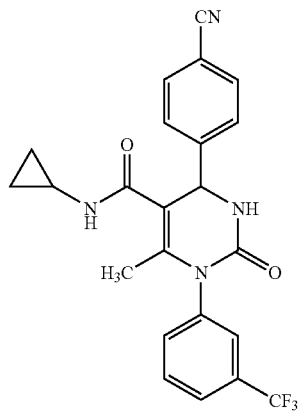

100 mg (0.25 mmol) of Example 5A are dissolved in 2 ml tetrahydrofuran, and 3 mg (0.02 mmol) 4-N,N-dimethylaminopyridine, 39 mg (0.3 mmol) N,N-diisopropylethylamine and 156 mg (0.3 mmol) benzotriazol-1-yloxy-tris(pyrrolidino)phosphonium hexafluorophosphate are added. The reaction mixture is stirred at room temperature for 15 minutes, then 29 mg (0.5 mmol) cyclopropylamine are added. The reaction mixture is stirred at room temperature for 72 hours. The mixture is evaporated to dryness in vacuo and the crude product is purified by preparative HPLC.

Yield: 71 mg (62% of th.)
LC-MS (method 2): $R_t$=3.98 min
MS (ESIpos): m/z=441 (M+H)$^+$.

In analogy to the procedure for Example 6, the following compounds are prepared:

| Example No. | Structure | Starting materials | Yield [%] | $R_t$ [min] (method) | Mass [M + H]$^+$ |
|---|---|---|---|---|---|
| 7 | 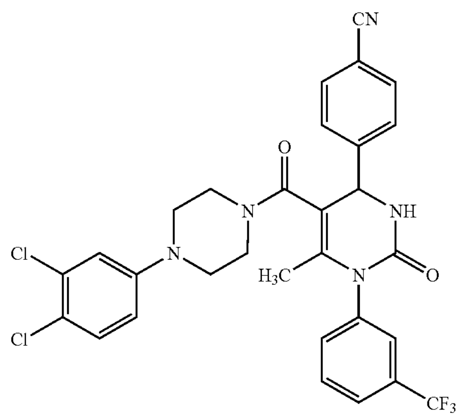 | Example 5A; 1-(3,4-dichlorophenyl)-piperazine | 61 | 4.32 (2) | 614 |
| 8 | 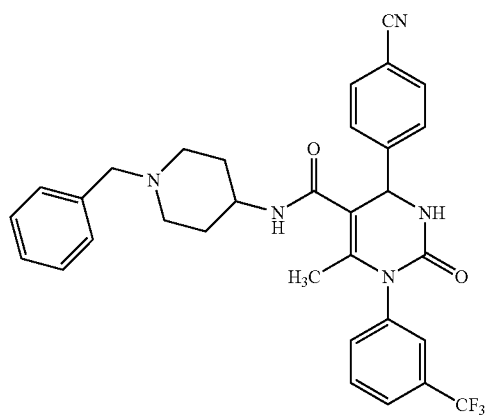 | Example 5A; 1-benzyl-piperidin-4-amine | 26 | 3.49 (2) | 574 |
| 9 | 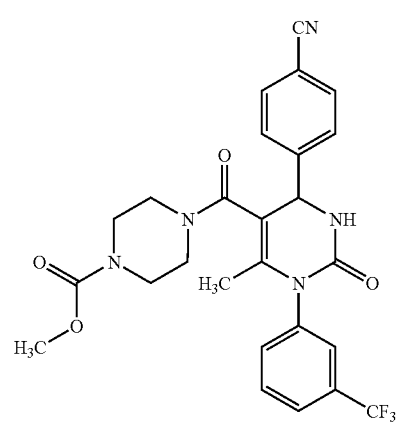 | Example 5A; methyl piperazine-1-carboxylate | 66 | 3.96 (2) | 528 |

-continued

| Example No. | Structure | Starting materials | Yield [%] | R_r [min] (method) | Mass [M + H]+ |
|---|---|---|---|---|---|
| 10 | 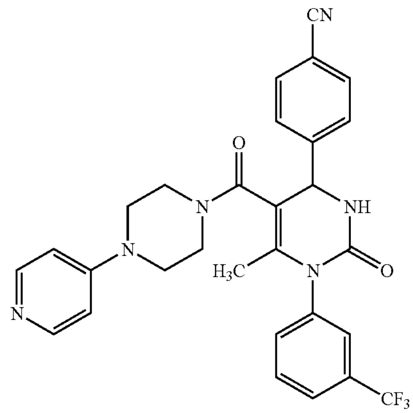 | Example 5A; 1-pyridin-4-yl-piperazine | 30 | 3.34 (2) | 547 |
| 11 | 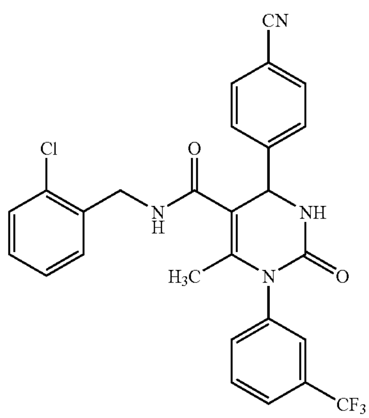 | Example 5A; 1-(2-chlorophenyl)methanamine | 44 | 4.20 (2) | 525 |
| 12 | 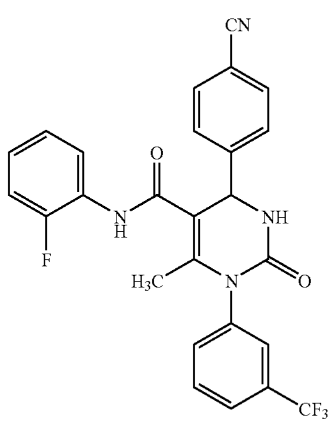 | Example 5A; 2-fluoroaniline | 20 | 4.24 (2) | 495 |

-continued

| Example No. | Structure | Starting materials | Yield [%] | R$_t$ [min] (method) | Mass [M + H]$^+$ |
|---|---|---|---|---|---|
| 13 | 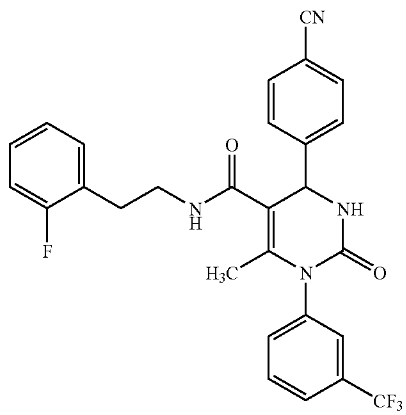 | Example 5A; 2-(2-fluorophenyl)ethanamine | 59 | 4.19 (2) | 523 |
| 14 | 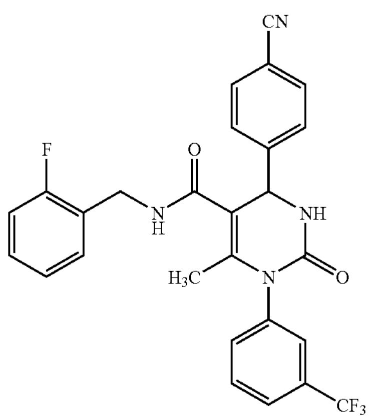 | Example 5A; 1-(2-fluorophenyl)methanamine | 56 | 4.15 (2) | 509 |
| 15 | 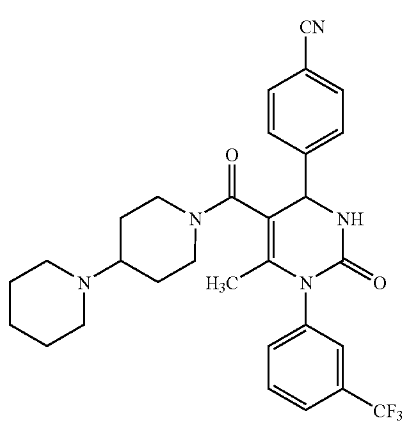 | Example 5A; 1,4'-bipiperidine | 23 | 3.35 (2) | 552 |

| Example No. | Structure | Starting materials | Yield [%] | $R_t$ [min] (method) | Mass $[M + H]^+$ |
|---|---|---|---|---|---|
| 16 | 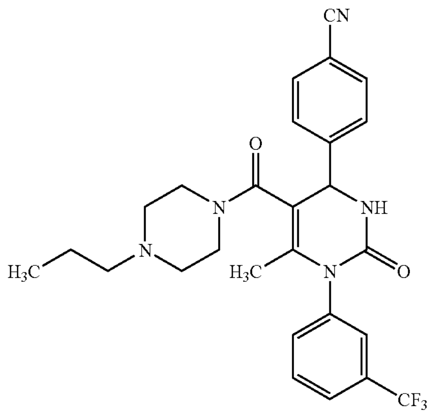 | Example 5A; 1-propyl-piperazine | 64 | 3.24 (2) | 514 |
| 17 | 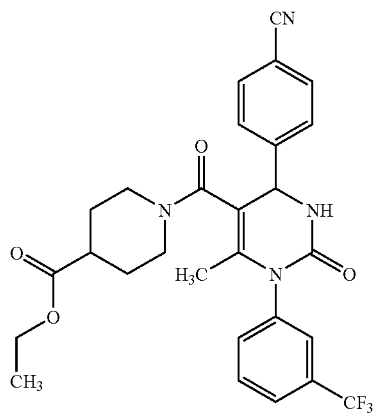 | Example 5A; ethyl piperidine-4-carboxylate | 73 | 4.10 (2) | 541 |

Examples 18 and 19

4-{5-[2-(Benzyloxy)propanoyl]-6-methyl-2-oxo-1-[3-(trifluoromethyl)phenyl]-1,2,3,4-tetrahydropyrimidin-4-yl}benzonitrile

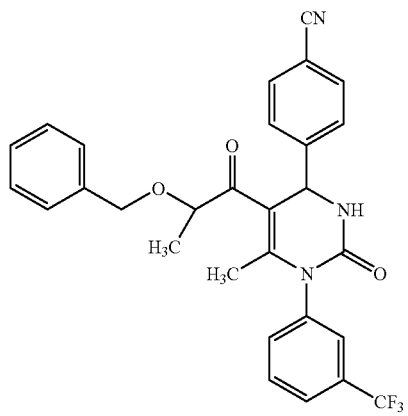

To a stirred solution of 5-(benzyloxy)hexane-2,4-dione (250 mg, 1.13 mmol; Example 8A), 4-cyanobenzaldehyde (149 mg, 1.13 mmol) and N-[3-(trifluoromethyl)phenyl]urea (232 mg, 1.13 mmol) in tetrahydrofuran (5 ml) is added polyphosphoric acid ethyl ester (700 mg). After 16 hours, the reaction solution is purified directly by preparative HPLC (RP18 column; eluent: acetonitrile/0.1% aq. formic acid 10:90→90:10). The fractions containing product are concentrated and again purified by preparative HPLC (RP18 column; eluent: acetonitrile/0.1% aq. formic acid 10:90→90:10).

Example 18

(Diastereomer I)

Yield: 28 mg (4.75% of th.)
HPLC (method 1): $R_t$=4.86 min, $\lambda_{max}$=234 nm
MS (ESIpos): m/z=520 (M+H)$^+$
$^1$H-NMR (300 MHz, DMSO-d$_6$): δ=8.46 (d, 1H, J=2.8Hz), 7.93-7.12 (m, 13H), 5.59 (d, 1H, J=2.8Hz), 4.30-4.11 (m, 3H), 1.87 (s, 3H), 1.32-1.11 (m, 3H) ppm.

Example 19

(Diastereomer II)

Yield: 24.3 mg (4.12% of th.)
HPLC (method 1): $R_t$=4.93 min, $\lambda_{max}$=232 nm
MS (ESIpos): m/z=520 (M+H)$^+$ $^1$H-NMR (300 MHz, DMSO-d$_6$): δ=8.48 (d, 1H, J=3.2Hz), 7.90-7.13 (m, 13H), 5.48 (d, 1H, J=2.8Hz), 4.50-4.27 (m, 3H), 1.88 (s, 3H), 1.14 (d, 3H, J=6.4Hz) ppm.

Example 20

4-{5-(Cyclobutylcarbonyl)-6-methyl-2-oxo-1-[3-(trifluoromethyl)phenyl]-1,2,3,4-tetrahydropyrimidin-4-yl}benzonitrile

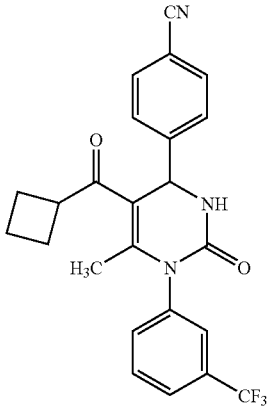

To a stirred suspension of 1-cyclobutylbutane-1,3-dione (69 mg, 0.49 mmol), N-[3-(trifluoromethyl)phenyl]urea (100 mg, 0.49 mmol) and 4-cyanobenzaldehyde (64.2 mg, 0.49 mmol) in tetrahydrofuran (250 ml) is added polyphosphoric acid ethyl ester (300 mg). The reaction mixture is stirred at reflux for 18 hours. After cooling to room temperature, the solvent is removed in vacuo and the crude product is purified by preparative HPLC (RP18 column; eluent: acetonitrile/ 0.1% aq. formic acid 10:90→90:10).

Yield: 54.6 mg (20% of th.)
LC-MS (method 5): R$_t$=2.57 min
HPLC (method 6): R$_t$=4.91 min, λ$_{max}$=200 nm
MS (ESIpos): m/z=457 (M+NH$_4$)$^+$
$^1$H-NMR (300 MHz, DMSO-d$_6$): δ=8.39 (d, 1H, J=3.7Hz), 7.98-7.48 (m, 8H), 5.36 (d, 1H, J=3.7Hz), 3.56-3.43 (m, 1H), 2.22-1.40 (m, 6H), 1.94 (s, 3H) ppm.

Example 21

4-{5-(Cyclohexylcarbonyl)-6-methyl-2-oxo-1-[3-(trifluoromethyl)phenyl]-1,2,3,4-tetrahydropyrimidin-4-yl}benzonitrile

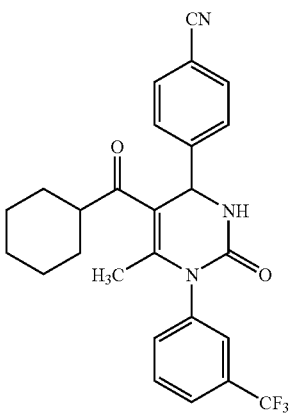

The title compound is prepared according to the procedure described for Example 20.

Yield: 72.8 mg (27% of th.)
LC-MS (method 3): R$_t$=2.63 min
HPLC (method 6): R$_t$=5.18 min, 196 nm
MS (ESIpos): m/z=485 (M+NH$_4$)$^+$
$^1$H-NMR (300 MHz, DMSO-d$_6$): δ=8.35 (d, 1H), 7.95-7.47 (m, 8H), 5.47 (d, 1H), 2.69 (m, 1H), 1.84 (s, 3H), 1.88-0.92 (m, 10H) ppm.

Example 22

4-{5-(Cyclopropylcarbonyl)-6-methyl-2-oxo-1-[3-(trifluoromethyl)phenyl]-1,2,3,4-tetrahydropyrimidin-4-yl}benzonitrile

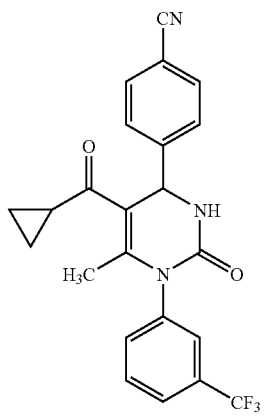

The title compound is prepared according to the procedure described for Example 18.

Yield: 113 mg (52% of th.)
LC-MS (method 5): R$_t$=2.46 min
HPLC (method 6): R$_t$=4.72 min, λ$_{max}$=202 nm
MS (ESIpos): m/z=443 (M+NH$_4$)$^+$
$^1$H-NMR (300 MHz, DMSO-d$_6$): δ=8.38 (d, 1H, J=3.6Hz), 7.91-7.51 (m, 8H), 5.53 (d, 1H, J=3.4Hz), 3.56-3.43 (m, 1H), 1.98 (s, 3H), 0.93-0.72 (m, 4H) ppm.

Example 23

(4R)-4-{5-(Cyclopropylcarbonyl)-6-methyl-2-oxo-1-[3-(trifluoromethyl)phenyl]-1,2,3,4-tetrahydropyrimidin-4-yl}benzonitrile

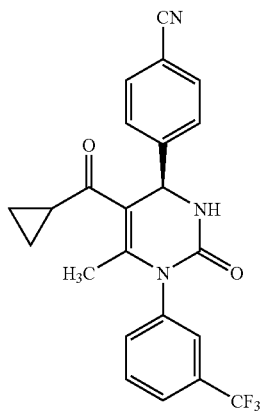

The enantiomers of Example 22 are separated by preparative HPLC on a chiral phase [chiral silica gel selector based on poly(N-methacryloyl-L-leucine-dicyclopropylmethylamide); column: 250 mm×20 mm; gradient: 0-6 minutes ethyl acetate, 6-8 minutes methanol, 8-10 minutes ethyl acetate; flow: 25 ml/min; detection: UV 254 nm].

$[\alpha]^{20}=+32.0°$ ($\lambda=589$ nm, methanol, c=633 mg/100 ml).

Example 24

4-{5-(4-Methoxybenzoyl)-6-methyl-2-oxo-1-[3-(trifluoromethyl)phenyl]-1,2,3,4-tetrahydropyrimidine-4-yl}benzonitrile

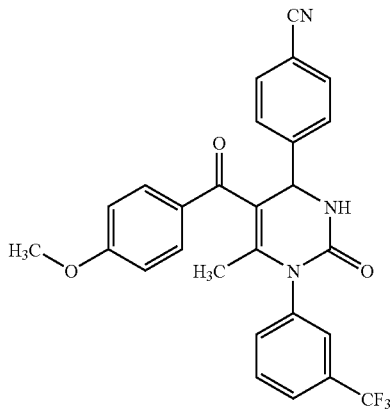

The title compound is prepared according to the procedure described for Example 18.

Yield: 69.7 mg (28% of th.)
LC-MS (method 4): $R_t=2.58$ min
HPLC (method 6): $R_t=4.83$ min, $\lambda_{max}=200$ nm
MS (ESIpos): m/z=492 (M+H)$^+$
$^1$H-NMR (300 MHz, CDCl$_3$): δ=7.75-7.39 (m, 10H), 6.89 (d, 2H), 5.67 (m, 2H), 3.85 (s, 3H), 1.49 (s, 3H) ppm.

Example 25

4-{5-[(2-Amino-4-methyl-1,3-thiazol-5-yl)carbonyl]-6-methyl-2-oxo-1-[3-(trifluoromethyl)phenyl]-1,2,3,4-tetrahydropyrimidin-4-yl}benzonitrile

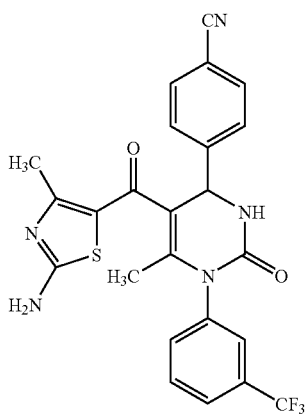

The title compound is prepared according to the procedure described for Example 18.

Yield: 63 mg (26% of th.)
LC-MS (method 3): $R_t=2.22$ min
MS (ESIpos): m/z=498 (M+H)$^+$
$^1$H-NMR (400 MHz, CDCl$_3$): δ=7.78-7.20 (m, 9H), 6.56-6.40 (m, 2H), 5.69 (br s, 1H), 2.24 (s, 3H), 1.93 (s, 3H) ppm.

Example 26 tert.-Butyl [6-(4-cyanophenyl)-5-(cyclobutylcarbonyl)-4-methyl-2-oxo-3-[3-(trifluoromethyl)phenyl]-3,6-dihydropyrimidine-1(2H)-yl]acetate

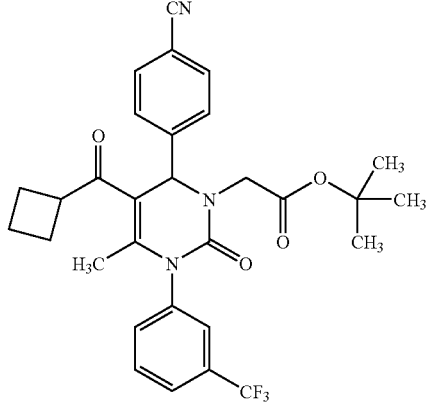

A stirred suspension of 4-{5-(cyclobutylcarbonyl)-6-methyl-2-oxo-1-[3-(trifluoromethyl)phenyl]-1,2,3,4-tetrahydropyrimidin-4-yl}benzonitrile (Example 20) (29 mg, 0.066 mmol) and potassium carbonate (16.4 mg, 0.12 mmol) in dimethylformamide (1 ml) is treated with tert.-butyl bromoacetate (14.2 mg, 0.073 mmol), and then stirred at room temperature overnight (16 h). The reaction solution is quenched with water (3 ml) and extracted with diethyl ether (2×5 ml). The combined organic phases are washed with brine, dried over anhydrous magnesium sulfate, filtered and concentrated.

Yield: 40 mg (94.4% of th.)
LC-MS (method 4): $R_t=3.05$ min
HPLC (method 1): $R_t=5.43$ min, $\lambda_{max}=234$ nm
MS (ESIpos): m/z=554 (M+H)$^+$
$^1$H-NMR (300 MHz, DMSO-d$_6$): δ=7.80-7.55 (m, 8H), 5.58 (br s, 1H), 4.19-3.91 (m, 2H), 3.60-3.47 (m, 1H), 2.40-0.85 (m, 6H), 1.94 (s, 3H), 1.26 (s, 9H) ppm.

Example 27 tert.-Butyl [6-(4-cyanophenyl)-5-(cyclopropylcarbonyl)-4-methyl-2-oxo-3-[3-(trifluoromethyl)phenyl]-3,6-dihydropyrimidin-1(2H)-yl]acetate

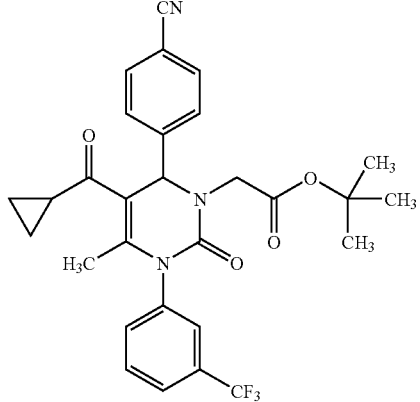

The title compound is prepared from Example 22 according to the procedure described for Example 26.
Yield: 89 mg (100% of th.)
LC-MS (method 4): $R_t$=2.93 min
HPLC (method 1): $R_t$=5.27 min, $\lambda_{max}$=200 nm
MS (ESIpos): m/z=540 (M+H)$^+$
$^1$H-NMR (300 MHz, DMSO-d$_6$): δ=7.95-7.54 (m, 8H), 5.73 (s, 1H), 4.16-3.83 (m, 2H), 2.23 (m, 1H), 1.98 (s, 3H), 1.29 (s, 9H), 0.91-0.72 (m, 4H) ppm.

Example 28 tert.-Butyl [6-(4-cyanophenyl)-5-(cyclohexylcarbonyl)-4-methyl-2-oxo-3-[3-(trifluoromethyl)phenyl]-3,6-dihydropyrimidin-1(2H)-yl]acetate

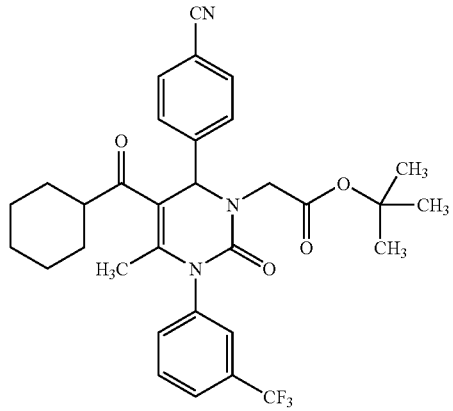

The title compound is prepared from Example 21 according to the procedure described for Example 26.
Yield: 65 mg (90% of th.)
HPLC (method 1): $R_t$=5.65 min, $\lambda_{max}$=234 nm
MS (ESIpos): m/z=582 (M+H)$^+$
$^1$H-NMR (300 MHz, DMSO-d$_6$): δ=7.90-7.52 (m, 8H), 5.68 (s, 1H), 4.20-3.88 (m, 2H), 2.78-2.66 (m, 1H), 1.72 (s, 3H), 1.69-1.00 (m, 10H), 1.29 (s, 9H) ppm.

Example 29 tert.-Butyl [5-[(2-amino-4-methyl-1,3-thiazol-5-yl)carbonyl]-6-(4-cyanophenyl)-4-methyl-2-oxo-3-[3-(trifluoromethyl)phenyl]-3,6-dihydropyrimidin-1(2H)-yl]acetate

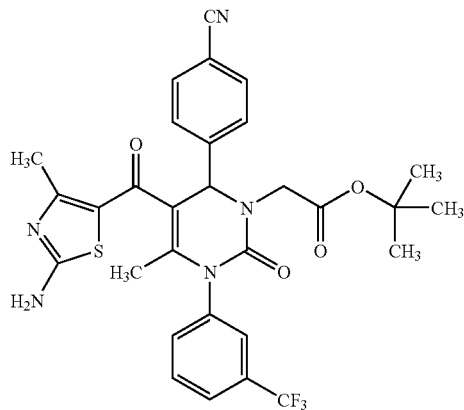

The title compound is prepared from Example 25 according to the procedure described for Example 26.
Yield: 38 mg (60% of th.)
LC-MS (method 4): $R_t$=2.11 min
MS (ESIpos): m/z=611 (M+H)$^+$
$^1$H-NMR (300 MHz, CDCl$_3$): δ=7.75-7.20 (m, 8H), 6.28 (s, 1H), 5.96 (d, 1H), 5.62 (d, 1H), 4.72 (d, 1H), 4.55 (d, 1H), 1.47-1.35 (m, 15H) ppm.

Example 30

[6-(4-Cyanophenyl)-5-(cyclobutylcarbonyl)-4-methyl-2-oxo-3-[3-(trifluoromethyl)phenyl]-3,6-dihydropyrimidin-1(2H)-yl]acetic acid

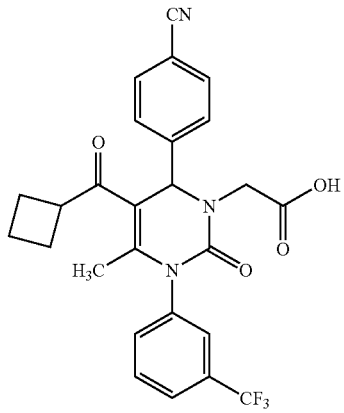

tert.-Butyl [6-(4-cyanophenyl)-5-(cyclobutylcarbonyl)-4-methyl-2-oxo-3-[3-(trifluoromethyl)phenyl]-3,6-dihydropyrimidine-1(2H)-yl]acetate (Example 26) (35 mg, 0.063 mmol) is dissolved in trifluoroacetic acid (1 ml). After 5 minutes stirring, the solution is concentrated in vacuo and the residue is purified by HPLC (RP18 column; eluent: acetonitrile/0.1% aq. formic acid 10:90→90:10).
Yield: 23.7 mg (65% of th.)
LC-MS (method 4): $R_t$=2.51 min
HPLC (method 1): $R_t$=4.82 min, $\lambda_{max}$=234 nm
MS (ESIpos): m/z=498 (M+H)$^+$
$^1$H-NMR (300 MHz, DMSO-d$_6$): δ=12.5 (br s, 1H), 7.96-7.54 (m, 8H), 5.61 (s, 1H), 4.19 (d, 1H), 3.85 (d, 1H), 2.30-1.60 (m, 7H), 1.91 (s, 3H) ppm.

Example 31

[6-(4-Cyanophenyl)-5-(cyclopropylcarbonyl)-4-methyl-2-oxo-3-[3-(trifluoromethyl)phenyl]-3,6-dihydropyrimidin-1(2H)-yl]acetic acid

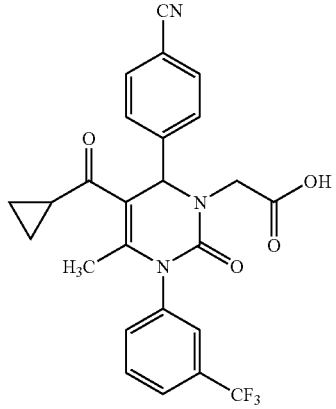

The title compound is prepared from Example 27 according to the procedure described for Example 30.
Yield: 27.1 mg (35% of th.)
LC-MS (method 3): $R_t$=2.20 min
HPLC (method 6): $R_t$=4.47 min, $\lambda_{max}$=234 nm
MS (ESIpos): m/z=484 (M+H)$^+$
$^1$H-NMR (300 MHz, DMSO-d$_6$): δ=13.0 (br s, 1H), 7.93-7.53 (m, 8H), 5.76 (s, 1H), 4.23-3.71 (m, 2H), 2.26 (m, 1H), 1.98 (s, 3H), 0.96-0.73 (m, 4H) ppm.

Example 32

[6-(4-Cyanophenyl)-5-(cyclohexylcarbonyl)-4-methyl-2-oxo-3-[3-(trifluoromethyl)phenyl]-3,6-dihydropyrimidine-1(2H)-yl]acetic acid

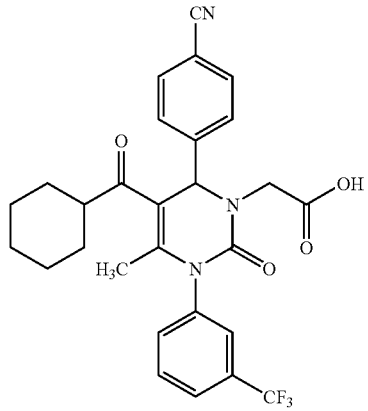

The title compound is prepared from Example 28 according to the procedure described for Example 30.
Yield: 18 mg (39% of th.)
LC-MS (method 4): $R_t$=2.69 min
HPLC (method 6): $R_t$=5.01 min, $\lambda_{max}$=236 nm
MS (ESIpos): m/z=526 (M+H)$^+$
$^1$H-NMR (300 MHz, DMSO-d$_6$): δ=12.5 (br s, 1H), 7.99-7.50 (m, 8H), 5.70 (s, 1H), 4.25-3.74 (m, 2H), 2.75 (m, 1H), 1.85 (s, 3H), 1.78-0.80 (m, 10H) ppm.

Example 33 tert.-Butyl [6-(4-cyanophenyl)-5-(4-methoxybenzoyl)-4-methyl-2-oxo-3-[3-(trifluoromethyl)phenyl]-3,6-dihydropyrimidin-1(2H)-yl]acetate

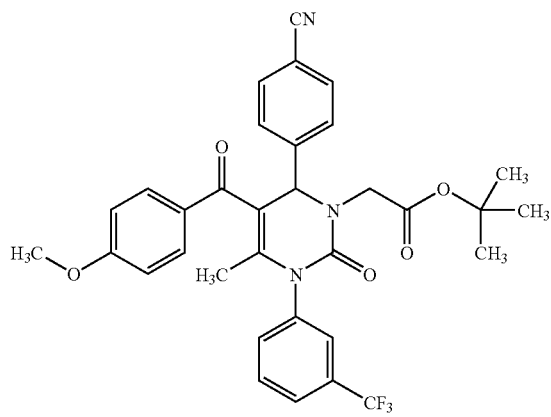

The title compound is prepared from Example 24 according to the procedure described for Example 26.
Yield: 141.2 mg (76% of th.)
HPLC (method 6): $R_t$=5.36 min, $\lambda_{max}$=189 nm
MS (ESIpos): m/z=606 (M+H)$^+$
$^1$H-NMR (300 MHz, CDCl$_3$): δ=7.79-7.40 (m, 8H), 7.38 (d, 2H), 6.92 (d, 2H), 5.62 (s, 1H), 4.61 (d, 1H), 3.88 (s, 3H), 3.39 (d, 1H), 1.55 (s, 3H), 1.49 (s, 9H) ppm.

Example 34

[6-(4-Cyanophenyl)-5-(4-methoxybenzoyl)-4-methyl-2-oxo-3-[3-(trifluoromethyl)phenyl]-3,6-dihydropyrimidine-1(2H)-yl]acetic acid

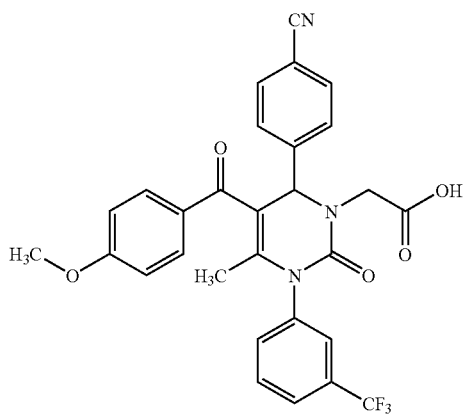

The title compound is prepared from Example 33 according to the procedure described for Example 30.
Yield: 81 mg (81% of th.)
LC-MS (method 3): $R_t$=2.34 min
HPLC (method 6): $R_t$=4.75 min, $\lambda_{max}$=200 nm
MS (ESIpos): m/z=550 (M+H)$^+$
$^1$H-NMR (300 MHz, DMSO-d$_6$): δ=12.72 (br s, 1H), 7.96-7.54 (m, 10H), 6.98 (d, 2H), 5.66 (s, 1H), 4.21 (d, 1H), 3.81 (s, 3H), 3.19 (d, 1H), 1.41 (s, 3H) ppm.

Example 35 tert.-Butyl 3-{[6-(4-cyanophenyl)-5-(cyclopropylcarbonyl)-4-methyl-2-oxo-3-[3-(trifluoro-methyl)phenyl]-3,6-dihydropyrimidin-1(2H)-yl]methyl}benzoate

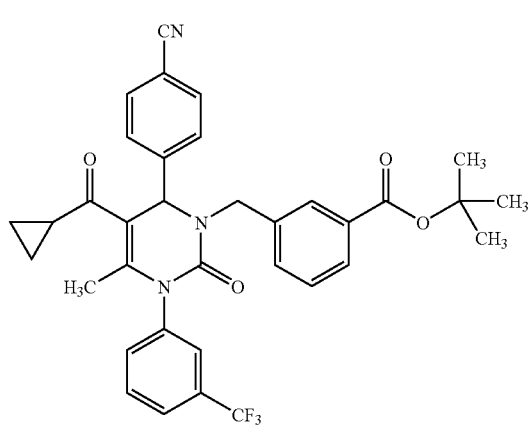

Sodium hydride (12.1 mg, 0.31 mmol; 60% suspension in mineral oil) is washed with pentane (3×3 ml), then treated with a solution of 4-{5-(cyclopropylcarbonyl)-6-methyl-2-oxo-1-[3-(trifluoromethyl)phenyl]-1,2,3,4-tetrahydropyrimidin-4-yl}benzonitrile (Example 22) (100 mg, 0.235 mmol) in tetrahydrofuran (5 ml). After 5 minutes, the reaction is treated with a solution of tert.-butyl 3-(bromomethyl)benzoate (77 mg, 0.28 mmol) in tetrahydrofuran (5 ml) and then stirred at room temperature overnight (16 h). The reaction mixture is quenched with water (50 ml) and extracted with ethyl acetate (3×150 ml). The combined organic phases are washed with brine, dried over anhydrous magnesium sulfate, filtered and concentrated in vacuo. The crude product is purified by preparative HPLC (RP18 column; eluent: acetonitrile/0.1% aq. formic acid 10:90→90:10).

Yield: 124 mg (84% of th.)

LC-MS (method 3): $R_t$=3.04 min

HPLC (method 6): $R_t$=5.59 min, $\lambda_{max}$=198 nm

MS (ESIpos): m/z=616 (M+H)$^+$ $^1$H-NMR (300 MHz, CDCl$_3$): δ=7.93-7.83 (m, 2H), 7.73-7.58 (m, 4H), 7.54-7.35 (m, 6H), 5.50 (s, 1H), 5.21 (d, 1H), 4.00 (d, 1H), 2.01 (s, 3H), 1.94 (m, 1H), 1.60 (s, 9H), 1.08-0.79 (m, 4H) ppm.

Example 36

3-{[6-(4-Cyanophenyl)-5-(cyclopropylcarbonyl)-4-methyl-2-oxo-3-[3-(trifluoromethyl)phenyl]-3,6-dihydropyrimidin-1(2H)-yl]methyl}benzoic acid

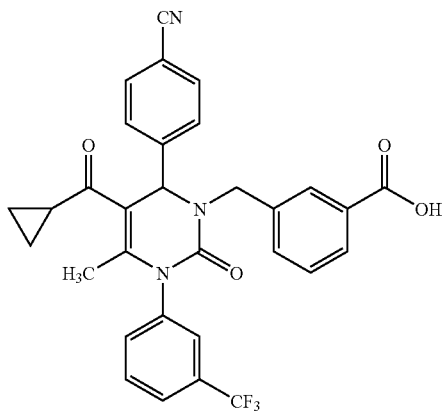

The title compound is prepared from Example 35 according to the procedure described for Example 30, with the exception that the reaction time is 30 minutes, and the title compound is purified by preparative HPLC (RP18 column; eluent: acetonitrile/water 30:70→90:10).

Yield: 67 mg (82% of th.)

LC-MS (method 4): $R_t$=2.59 min

MS (ESIpos): m/z=560 (M+H)$^+$ $^1$H-NMR (300 MHz, DMSO-d$_6$): δ=12.90 (br s, 1H), 7.86-7.35 (m, 12H), 5.68 (s, 1H), 4.90 (d, 1H), 4.30 (d, 1H), 2.21 (m, 1H), 1.95 (s, 3H), 0.95-0.76 (m, 4H) ppm.

Example 37 tert.-Butyl 4-({4-(4-cyanophenyl)-6-methyl-2-oxo-1-[3-(trifluoromethyl)phenyl]-1,2,3,4-tetrahydropyrimidin-5-yl}carbonyl)piperidine-1-carboxylate

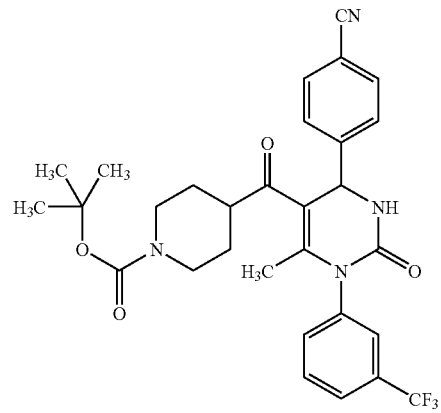

The title compound is prepared according to the procedure described for Example 18.

Yield: 20 mg (2% of th.)

LC-MS (method 4): $R_t$=2.73 min

HPLC (method 6): $R_t$=5.09 min, $\lambda_{max}$=196 nm

MS (ESIpos): m/z=569 (M+H)$^+$ $^1$H-NMR (300 MHz, DMSO-d$_6$): δ=8.40 (br d, 1H), 8.17-7.19 (m, 8H), 5.51 (br d, 1H), 4.00-3.70 (m, 1H), 3.03-2.39 (m, 3H), 1.85 (s, 3H), 1.80-1.66 (m, 2H), 1.37 (s, 9H), 1.56-1.00 (m, 2H) ppm.

Example 38 tert.-Butyl 3-{[6-(4-cyanophenyl)-5-(cyclohexylcarbonyl)-4-methyl-2-oxo-3-[3-(trifluoromethyl)phenyl]-3,6-dihydropyrimidin-1(2H)-yl]methyl}benzoate

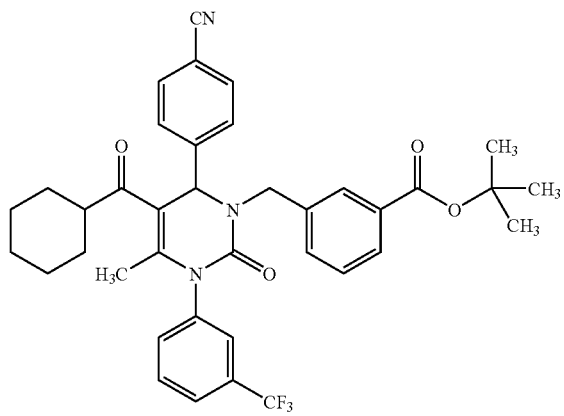

The title compound is prepared from Example 21 according to the procedure described for Example 35.

Yield: 65 mg (46% of th.)

LC-MS (method 3): $R_t$=3.31 min

MS (ESIpos): m/z=658 (M+H)$^+$ $^1$H-NMR (200 MHz, DMSO-d$_6$): δ=7.90-7.39 (m, 12H), 5.58 (s, 1H), 4.97 (d, 1H), 4.31 (d, 1H), 2.67 (m, 1H), 1.80 (s, 3H), 1.52 (s, 9H), 1.70-0.85 (m, 10H) ppm.

Example 39 tert.-Butyl 4-({3-(2-tert.-butoxy-2-oxoethyl)-4-(4-cyanophenyl)-6-methyl-2-oxo-1-[3-(trifluoromethyl)phenyl]-1,2,3,4-tetrahydropyrimidin-5-yl}carbonyl)piperidine-1-carboxylate

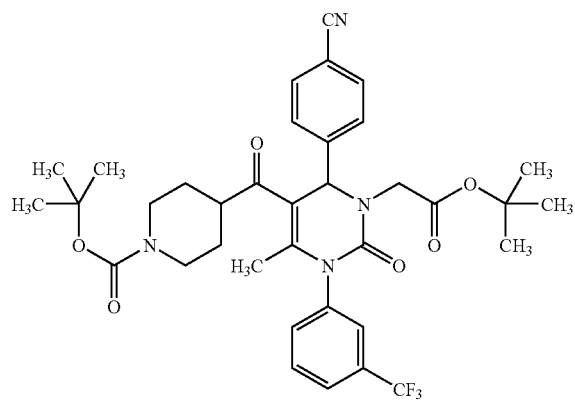

A stirred suspension of tert.-butyl 4-({4-(4-cyanophenyl)-6-methyl-2-oxo-1-[3-(trifluoromethyl) phenyl]-1,2,3,4-tetrahydropyrimidin-5-yl}carbonyl)piperidine-1-carboxylate (Example 37) (43 mg, 0.08 mmol) and potassium carbonate (19 mg, 0.14 mmol) in dimethylformamide (1.5 ml) is treated with tert.-butyl bromoacetate (16 mg, 0.08 mmol), then stirred at room temperature overnight (16 h). The reaction solution is then diluted with methanol (7 ml) and purified directly by preparative HPLC (RP18 column; eluent: acetonitrile/water 10:90→90:10).

Yield: 26.5 mg (51% of th.)

LC-MS (method 3): $R_t$=3.02 min

MS (ESIpos): m/z=682 (M+H)$^+$

HPLC (method 6): $R_t$=5.44 min, $\lambda_{max}$=234 nm $^1$H-NMR (300 MHz, DMSO-d$_6$): δ=8.43-7.34 (m, 8H), 5.71 (s, 1H), 4.22-3.74 (m, 4H), 3.10-2.39 (m, 4H), 1.84 (s, 3H), 1.88-1.69 (m, 1H), 1.54-1.00 (s, 20H) ppm.

Example 40

3-{[6-(4-Cyanophenyl)-5-(cyclohexylcarbonyl)-4-methyl-2-oxo-3-[3-(trifluoromethyl)phenyl]-3,6-dihydropyrimidin-1(2H)-yl]methyl}benzoic acid

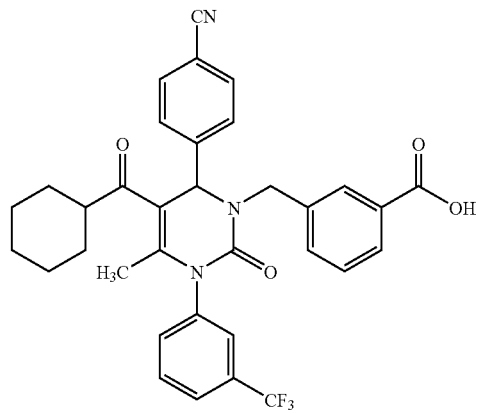

The title compound is prepared from Example 38 according to the procedure described for Example 30, with the exception that the reaction time is 30 minutes, and the title compound is purified by preparative HPLC (RP18 column; eluent: acetonitrile/water 30:70→90:10).

Yield: 40 mg (77% of th.)

HPLC (method 6): $R_t$=5.15 min, $\lambda_{max}$=200 nm

MS (ESIpos): m/z=602 (M+H)$^+$ $^1$H-NMR (300 MHz, DMSO-d$_6$): δ=12.95 (s, 1H), 7.94-7.40 (m, 12H), 5.51 (s, 1H), 5.00 (d, 1H), 4.21 (d, 1H), 2.77-2.60 (m, 1H), 1.80 (s, 3H), 1.68-1.36 (m, 5H), 1.29-0.90 (m, 5H) ppm.

Example 41

Diethyl {4-(4-cyanophenyl)-6-methyl-2-oxo-1-[3-(trifluoromethyl)phenyl]-1,2,3,4-tetrahydropyrimidin-5-yl}phosphonate

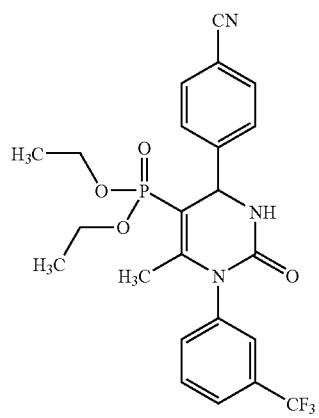

A solution of diethyl (2-oxopropyl)phosphonate (250 mg, 1.29 mmol), 4-cyanobenzaldehyde (168.84 mg, 1.29 mmol), N-[3-(trifluoromethyl)phenyl]urea (263 mg, 1.29 mmol) and polyphosphoric acid ethyl ester (0.70 g) in tetrahydrofuran (5 ml) is refluxed overnight with stirring. The reaction solution is purified directly by preparative HPLC (RP18 column; eluent: acetonitrile/water 10:90→90:10). The fractions containing product are concentrated in vacuo and re-purified by flash chromatography on silica gel 60 with dichloromethane/methanol as eluent.

Yield: 20 mg (3% of th.)

HPLC (method 1): $R_t$=4.31 min, $\lambda_{max}$=236 nm

MS (ESIpos): m/z=494 (M+H)$^+$ $^1$H-NMR (300 MHz, DMSO-d$_6$): δ=8.39-8.27 (m, 1H), 7.07-7.48 (m, 8H), 4.98-4.84 (m, 1H), 3.79-3.19 (m, 4H), 2.50 (s, 3H), 1.05 (t, 3H), 0.95 (t, 3H) ppm.

Example 42

Methyl 5-{[6-(4-cyanophenyl)-5-(cyclopropylcarbonyl)-4-methyl-2-oxo-3-[3-(trifluoromethyl)phenyl]-3,6-dihydropyrimidin-1(2H)-yl]methyl}-2-furoate

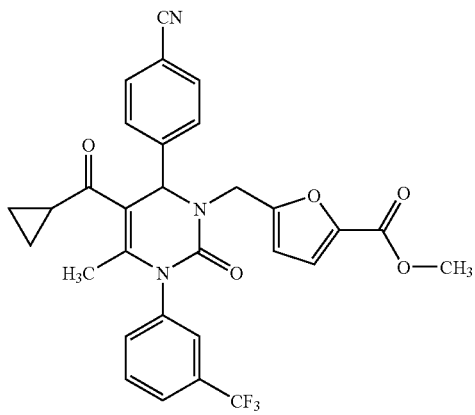

To a stirred suspension of 4-{5-(cyclopropylcarbonyl)-6-methyl-2-oxo-1-[3-(trifluoromethyl)phenyl]-1,2,3,4-tetrahydropyrimidin-4-yl}benzonitrile (Example 22) (150 mg, 0.35 mmol) and potassium carbonate (98 mg, 0.71 mmol) in dimethylformamide (3 ml) is added methyl 5-(chloromethyl)-2-furoate (92 mg, 0.53 mmol). The suspension is stirred at room temperature overnight (16 h), then additional methyl 5-(chloromethyl)-2-furoate (6.1 mg, 0.35 mmol) and potassium carbonate (49 mg, 0.35 mmol) are added, and the suspension is stirred an additional 72 hours. The reaction mixture is diluted with methanol (5 ml) and purified directly by preparative HPLC (RP 18 column; eluent: acetonitrile/water 10:90→90:10). The title compound is isolated as a brownish amorphous solid.

Yield: 72 mg (35% of th.)

LC-MS (method 4): $R_t$=2.75 min

MS (ESIpos): m/z=564 (M+H)$^+$

HPLC (method 1): $R_t$=4.98 min, $\lambda_{max}$=196 nm $^1$H-NMR (300 MHz, DMSO-d$_6$): δ=7.99-7.41 (m, 8H), 7.13 (d, 1H, J=3.58Hz), 6.47 (d, 1H, J=3.58Hz), 5.73 (s, 1H), 4.78 (d, 1H), 4.50 (d, 1H), 3.78 (s, 3H), 2.57-2.48 (m, 1H), 1.94 (s, 3H), 1.03-0.73 (m, 4H) ppm.

Example 43

Methyl 2-{[6-(4-cyanophenyl)-5-(cyclopropylcarbonyl)-4-methyl-2-oxo-3-[3-(trifluoromethyl)phenyl]-3,6-dihydropyrimidin-1(2H)-yl]methyl}-1,3-oxazole-4-carboxylate

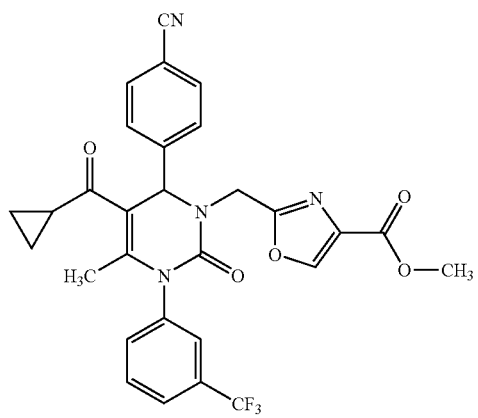

To a stirred suspension of 4-{5-(cyclopropylcarbonyl)-6-methyl-2-oxo-1-[3-(trifluoromethyl)phenyl]-1,2,3,4-tetrahydropyrimidin-4-yl}benzonitrile (Example 22) (150 mg, 0.35 mmol) and potassium carbonate (98 mg, 0.71 mmol) in dimethylformamide (3 ml) is added methyl 2-(chloromethyl)-1,3-oxazole-4-carboxylate (93 mg, 0.53 mmol). The reaction mixture is stirred at room temperature overnight, then an additional equivalent of potassium carbonate (0.35 mmol) and methyl 2-(chloromethyl)-1,3-oxazole-4-carboxylate (0.35 mmol) are added, and the solution is stirred an additional 72 hours. The reaction mixture is quenched with water (20 ml) and extracted with ethyl acetate (3×50 ml). The combined organic phases are washed with brine, dried over anhydrous magnesium sulfate, filtered and concentrated. The residue is purified by HPLC (RP18 column; eluent: acetonitrile/water 30:70→90:10).

Yield: 74 mg (37% of th.)

LC-MS (method 5): $R_t$=2.61 min

MS (ESIpos): m/z=565 (M+H)$^+$

HPLC (method 1): $R_t$=4.78 min, $\lambda_{max}$=196 nm $^1$H-NMR (300 MHz, DMSO-d$_6$): δ=8.68 (s, 1H), 7.92-7.48 (m, 8H), 5.84 (s, 1H), 4.91-4.51 (m, 2H), 3.79 (s, 3H), 2.37-2.23 (m, 1H), 1.96 (s, 3H), 0.96-0.72 (m, 4H) ppm.

Example 44

2-[6-(4-Cyanophenyl)-5-(cyclopropylcarbonyl)-4-methyl-2-oxo-3-[3-(trifluoromethyl)phenyl]-3,6-dihydropyrimidin-1(2H)-yl]-N-[(4-cyanophenyl)sulfonyl]acetamide

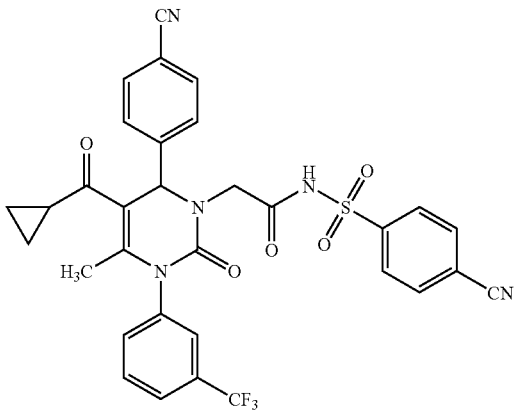

A mixture of [6-(4-cyanophenyl)-5-(cyclopropylcarbonyl)-4-methyl-2-oxo-3-[3-(trifluoromethyl)phenyl]-3,6-dihydropyrimidin-1(2H)-yl]acetic acid (Example 31) (100 mg, 0.21 mmol), 1,3-dicyclohexylcarbodiimide (41.5 mg, 0.23 mmol), 4-cyanobenzene-1-sulfonamide (41.5 mg, 0.23 mmol) and 4-dimethylaminopyridine (28 mg, 0.23 mmol) in dichloromethane (4 ml) is stirred for 48 hours. The product is extracted with dichloromethane, washed with 2 N hydrochloric acid and brine, dried over anhydrous magnesium sulfate, filtered and concentrated. The residue is purified by preparative HPLC (RP18 column; eluent: acetonitrile/water 10:90→90:10).

Yield: 45 mg (33% of th.)
LC-MS (method 3): $R_t$=2.56 min
MS (ESIpos): m/z=648 (M+H)$^+$
HPLC (method 1): $R_t$=4.83 min, $\lambda_{max}$=198 nm
$^1$H-NMR (300 MHz, DMSO-d$_6$): δ=8.22-7.98 (m, 4H), 7.93-7.45 (m, 9H), 5.65 (s, 1H), 4.30-3.63 (m, 2H), 2.34-2.13 (m, 1H), 1.94 (s, 3H), 0.98-0.70 (m, 4H) ppm.

Example 45

2-[6-(4-Cyanophenyl)-5-(cyclopropylcarbonyl)-4-methyl-2-oxo-3-[3-(trifluoromethyl)phenyl]-3,6-dihydropyrimidin-1(2H)-yl]-N-[(2,2,2-trifluoroethyl)sulfonyl]acetamide

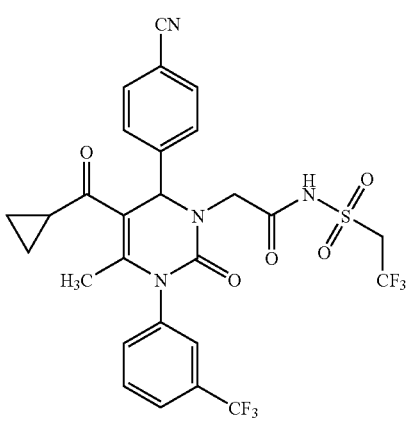

A mixture of [6-(4-cyanophenyl)-5-(cyclopropylcarbonyl)-4-methyl-2-oxo-3-[3-(trifluoromethyl)phenyl]-3,6-dihydropyrimidin-1(2H)-yl]acetic acid (Example 31) (100 mg, 0.21 mmol), 2,2,2-trifluoroethanesulfonamide (37 mg, 0.23 mmol), 1,3-dicyclohexylcarbodiimide (47 mg, 0.23 mmol) and 4-dimethylaminopyridine (28 mg, 0.23 mmol) in dichloromethane (4 ml) is stirred for 48 hours. The crude product is extracted with dichloromethane (100 ml), washed with 2 N hydrochloric acid and brine, dried over anhydrous magnesium sulfate, filtered and concentrated. The residue is purified by flash chromatography with silica gel 60 (50 g) and 2:1 cyclohexane/ethyl acetate as eluent.

Yield: 73 mg (56% of th.)
MS (ESIpos): m/z=629 (M+H)$^+$
HPLC (method 1): $R_t$=4.84 min, $\lambda_{max}$=234 nm
$^1$H-NMR (300 MHz, DMSO-d$_6$): δ=7.94-7.48 (m, 9H), 5.75 (s, 1H), 4.3 (d, 1H), 4.08 (q, 2H), 3.12 (d, 1H), 2.44-2.25 (m, 1H), 1.90 (s, 3H), 0.99-0.72 (m, 4H) ppm.

Example 46

Methyl 5-{[6-(4-cyanophenyl)-5-(cyclohexylcarbonyl)-4-methyl-2-oxo-3-[3-(trifluoromethyl)phenyl]-3,6-dihydropyrimidin-1(2H)-yl]methyl}-2-furoate

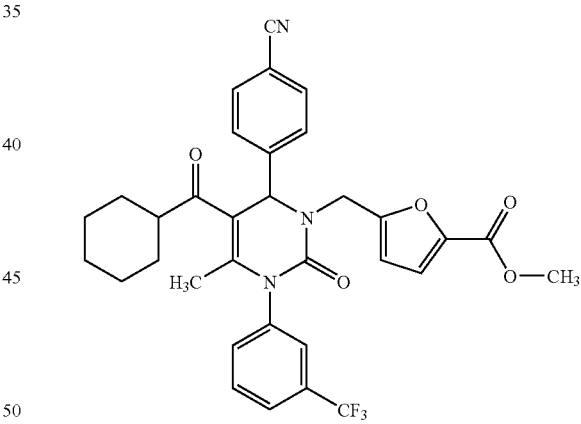

The title compound is prepared from Example 21 according to the procedure described for Example 42, with the exception that only 1.5 equivalents of methyl 5-(chloromethyl)-2-furoate and 2 equivalents of potassium carbonate are used. The title compound is purified by preparative HPLC (RP18 column; eluent: acetonitrile/0.1% aq. formic acid 30:70→90:10).

Yield: 65 mg (34% of th.)
LC-MS (method 4): $R_t$=3.10 min
MS (ESIpos): m/z=606 (M+H)$^+$
$^1$H-NMR (300 MHz, DMSO-d$_6$): δ=7.95-7.48 (m, 8H), 7.19 (m, 1H), 6.53 (m, 1H), 5.59 (s, 1H), 4.88 (d, 1H), 4.43 (d, 1H), 3.79 (s, 3H), 2.78-2.65 (m, 1H), 1.78 (s, 3H), 1.70-0.97 (m, 10H).

Example 47

Methyl 2-{[6-(4-cyanophenyl)-5-(cyclohexylcarbonyl)-4-methyl-2-oxo-3-[3-(trifluoromethyl)phenyl]-3,6-dihydropyrimidin-1(2H)-yl]methyl}-1,3-oxazole-4-carboxylate

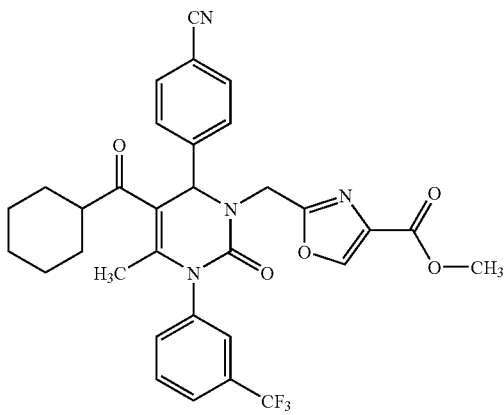

The title compound is prepared from Example 21 according to the procedure described for Example 43, with the exception that only 2 equivalents of potassium carbonate and 1.5 equivalents of methyl 2-(chloromethyl)-1,3-oxazole-4-carboxylate are used. The reaction time is 72 hours.

Yield: 80 mg (41% of th.)
LC-MS (method 4): $R_t$=2.76 min
MS (ESIpos): m/z=607 (M+H)$^+$
HPLC (method 1): $R_t$=5.41 min, $\lambda_{max}$=194 nm
$^1$H-NMR (300 MHz, DMSO-d$_6$): δ=8.71 (s, 1H), 7.93-7.54 (m, 8H), 5.74 (s, 1H), 4.93 (d, 1H), 4.53 (d, 1H), 3.80 (s, 3H), 2.79-2.67 (m, 1H), 1.81 (s, 3H), 1.69-0.97 (m, 10H) ppm.

Example 48

5-{[6-(4-Cyanophenyl)-5-(cyclopropylcarbonyl)-4-methyl-2-oxo-3-[3-(trifluoromethyl)phenyl]-3,6-dihydropyrimidin-1(2H)-yl]methyl}-2-furoic acid

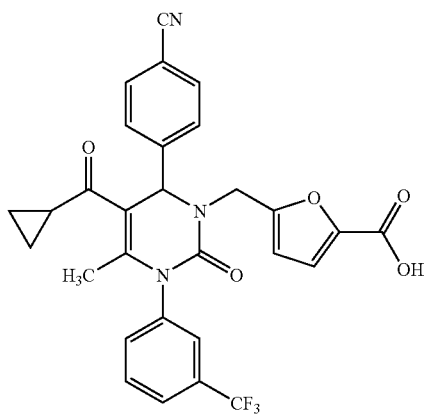

A stirred solution of methyl 5-{[6-(4-cyanophenyl)-5-(cyclopropylcarbonyl)-4-methyl-2-oxo-3-[3-(trifluoromethyl)phenyl]-3,6-dihydropyrimidin-1(2H)-yl]methyl}-2-furoate (Example 42) (50 mg, 0.09 mmol) in tetrahydrofuran (1.5 ml) is treated with a solution of lithium hydroxide (2.34 mg, 0.1 mmol) in water (1.5 ml). After three hours stirring at room temperature, additional lithium hydroxide (2.34 mg, 0.1 mmol) is added. The reaction solution is stirred overnight (16 h), then allowed to stand for 48 h. The solution is acidified with 1 N hydrochloric acid (500 µl). After 5 minutes stirring, a precipitate is obtained. Methanol (3 ml) is added, and the crude reaction solution is purified directly by preparative HPLC (RP18 column; eluent: acetonitrile/water 30:70→90:10). The title compound is isolated as a brownish solid.

Yield: 27.5 mg (56.4% of th.)
HPLC (method 6): $R_t$=4.71 min, $\lambda_{max}$=244 nm
MS (ESIpos): m/z=550 (M+H)$^+$
$^1$H-NMR (400 MHz, DMSO-d$_6$): δ=13.1 (br s, 1H), 7.90-7.76 (m, 4H), 7.74 (t, 1H), 7.63 (d, 1H), 7.51 (d, 2H), 7.03 (m, 1H), 6.45 (d, 1H), 5.72 (s, 1H), 4.84 (d, 1H), 4.38 (d, 1H), 2.28 (m, 1H), 1.95 (s, 3H), 0.98-0.75 (m, 4H) ppm.

Example 49

2-[6-(4-Cyanophenyl)-5-(cyclohexylcarbonyl)-4-methyl-2-oxo-3-[3-(trifluoromethyl)phenyl]-3,6-dihydropyrimidin-1(2H)-yl]-N-[(4-cyanophenyl)sulfonyl]acetamide

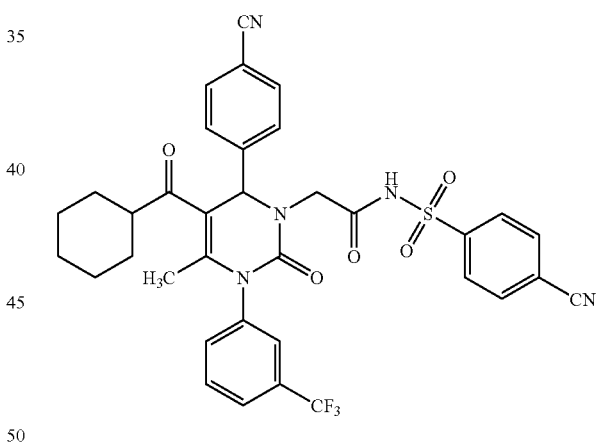

The title compound is prepared from Example 32 according to the procedure described for Example 44, with the exception that the title compound is purified by HPLC (RP18 column; eluent: acetonitrile/water 30:70→90:10).

Yield: 65 mg (48% of th.)
LC-MS (method 3): $R_t$=2.93 min
MS (ESIpos): m/z=690 (M+H)$^+$
HPLC (method 1): $R_t$=5.28 min, $\lambda_{max}$=198 nm
$^1$H-NMR (300 MHz, DMSO-d$_6$): δ=12.57 (br s, 1H), 8.06 (d of d, 4H), 7.84 (d, 2H), 7.75-7.62 (m, 3H), 7.58-7.49 (m, 3H), 5.56 (s, 1H), 4.16 (d, 1H), 3.86 (d, 1H), 2.64 (m, 1H), 1.79 (s, 3H), 1.68-0.93 (m, 10H) ppm.

Example 50

2-[6-(4-Cyanophenyl)-5-(cyclohexylcarbonyl)-4-methyl-2-oxo-3-[3-(trifluoromethyl)phenyl]-3,6-dihydropyrimidin-1(2H)-yl]-N-[(2,2,2-trifluoroethyl)sulfonyl]acetamide

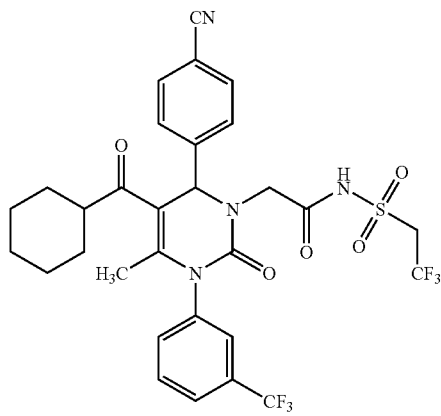

The title compound is prepared from Example 32 according to the procedure described for Example 45, with the exception that the title compound is purified by preparative HPLC (RP18 column; eluent: acetonitrile/water 30:70→90:10).

Yield: 52 mg (40% of th.)

HPLC (method 1): $R_t$=5.30 min, $\lambda_{max}$=238 nm

MS (ESIpos): m/z=671 (M+H)$^+$ $^1$H-NMR (300 MHz, DMSO-d$_6$): δ=7.89 (d, 2H), 7.80 (d, 1H), 7.71 (t, 2H), 7.62 (d, 2H), 7.59 (s, 1H), 5.66 (s, 1H), 4.70-4.50 (m, 2H), 4.28 (d, 1H), 3.86 (d, 1H), 2.72 (m, 1H), 1.82 (s, 3H), 1.91-0.96 (m, 10H) ppm.

Example 51

2-{[6-(4-Cyanophenyl)-5-(cyclopropylcarbonyl)-4-methyl-2-oxo-3-[3-(trifluoromethyl)phenyl]-3,6-dihydropyrimidin-1(2H)-yl]methyl}-1,3-oxazole-4-carboxylic acid

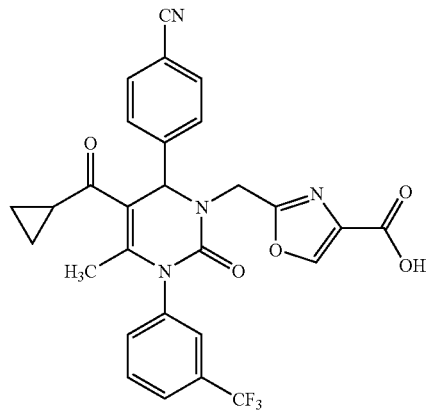

To a stirred solution of methyl 2-{[6-(4-cyanophenyl)-5-(cyclopropylcarbonyl)-4-methyl-2-oxo-3-[3-(trifluoromethyl)phenyl]-3,6-dihydropyrimidin-1(2H)-yl]methyl}-1,3-oxazole-4-carboxylate (Example 43) (50 mg, 0.09 mmol) in tetrahydrofuran (1.5 ml) is added a solution of lithium hydroxide (4.24 mg, 0.18 mmol) in water (1.5 ml). The reaction solution is stirred at room temperature overnight (16 h). The pH of the solution is adjusted to less than pH 7 with 1 N hydrochloric acid (500 μl). After 5 minutes stirring, a precipitate is obtained. Methanol (3 ml) is added, and the crude reaction solution is purified directly by preparative HPLC (RP18 column; eluent: acetonitrile/0.1% aq. formic acid 30:70→90:10). The title compound is isolated as a colourless solid.

Yield: 41 mg (84% of th.)

LC-MS (method 3): $R_t$=2.22 min

MS (ESIpos): m/z=551 (M+H)$^+$ $^1$H-NMR (300 MHz, DMSO-d$_6$): δ=13.01 (br s, 1H), 8.57 (s, 1H), 7.90-7.52 (m, 8H), 5.84 (s, 1H), 4.88 (d, 1H), 4.51 (d, 1H), 2.30 (m, 1H), 1.96 (s, 3H), 0-96-0.73 (m, 4H) ppm.

Example 52

5-{[6-(4-Cyanophenyl)-5-(cyclohexylcarbonyl)-4-methyl-2-oxo-3-[3-(trifluoromethyl)phenyl]-3,6-dihydropyrimidin-1(2H)-yl]methyl}-2-furoic acid

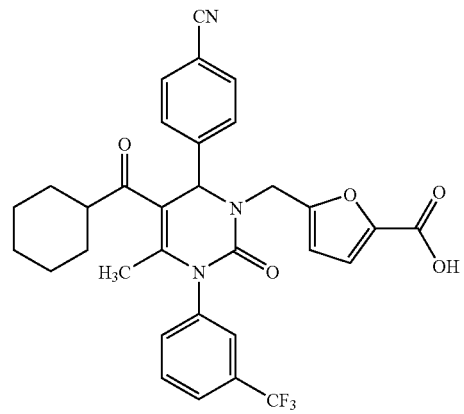

The title compound is prepared from Example 46 according to the procedure described for Example 48, with the exception that the title compound is purified by preparative HPLC (RP18 column; eluent: acetonitrile/0.1% aq. formic acid 10:90→90:10).

Yield: 43 mg (77% of th.)

HPLC (method 1): $R_t$=5.20 min, $\lambda_{max}$=202 nm

LC-MS (method 4): $R_t$=2.80 min

MS (ESIpos): m/z=592 (M+H)$^+$ $^1$H-NMR (300 MHz, DMSO-d$_6$): δ=13.0 (br s, 1H), 7.90-7.65 (m, 5H), 7.63-7.46 (m, 3H), 7.10 (d, 1H), 6.53 (d, 1H), 5.55 (s, 1H), 4.92 (d, 1H), 4.32 (d, 1H), 2.77-2.63 (m, 1H), 1.79 (s, 3H), 1.68-1.37 (m, 5H), 1.31-0.93 (m, 5H) ppm.

Example 53

2-{[6-(4-Cyanophenyl)-5-(cyclohexylcarbonyl)-4-methyl-2-oxo-3-[3-(trifluoromethyl)phenyl]-3,6-dihydropyrimidin-1(2H)-yl]methyl}-1,3-oxazole-4-carboxylic acid

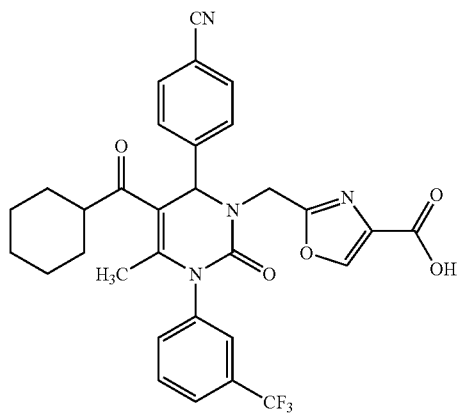

The title compound is prepared from Example 47 according to the procedure described for Example 51, with the exception that the title compound is purified by preparative HPLC (RP18 column; eluent: acetonitrile/0.1% aq. formic acid 10:90→90:10).

Yield: 46 mg (84% of th.)
LC-MS (method 3): $R_t$=2.52 min
MS (ESIpos): m/z=593 (M+H)$^+$
HPLC (method 1): $R_t$=5.07 min, $\lambda_{max}$=194 nm
$^1$H-NMR (300 MHz, DMSO-d$_6$): δ=13.0 (br s, 1H), 8.58 (s, 1H), 7.86 (d, 2H), 7.83-7.60 (m, 4H), 7.58 (d, 2H), 5.72 (s, 1H), 4.95 (d, 1H), 4.47 (d, 1H), 2.80-2.66 (m, 1H), 1.81 (s, 3H), 1.69-0.95 (m, 10H) ppm.

Example 54

Benzyl 2-({4-(4-cyanophenyl)-6-methyl-2-oxo-1-[3-(trifluoromethyl)phenyl]-1,2,3,4-tetrahydropyrimidin-5-yl}carbonyl)piperidine-1-carboxylate

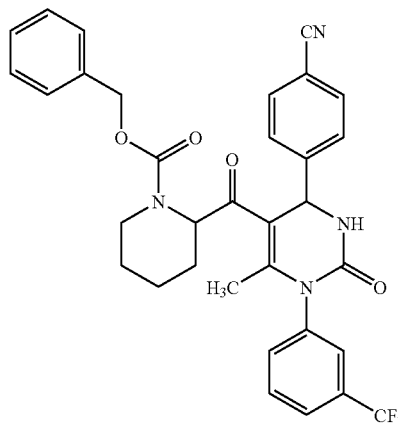

A stirred mixture of benzyl 2-acetoacetylpiperidine-1-carboxylate (Example 10A) (1.74 g, 5.74 mmol), 4-cyanobenzaldehyde (752 mg, 5.74 mmol), N-[3-(trifluoromethyl)phenyl]urea (976 mg, 4.78 mmol) and 2,4,6-tripropyl-1,3,5,2,4,6-trioxatriphosphinane 2,4,6-trioxide anhydride (6.1 g, 9.5 mmol) in methyl tert.-butyl ether (44 ml) is refluxed overnight (16 h). The product is extracted with methyl tert.-butyl ether (300 ml), washed with aq. saturated sodium bicarbonate solution (200 ml), dried with anhydrous magnesium sulfate, filtered and concentrated. The residue is chromatographed with silica gel 60 using cyclohexane/ethyl acetate as eluent.

Yield: 858 mg (30% of th.)
HPLC (method 1): $R_t$=5.16 min, $\lambda_{max}$=232 nm
MS (ESIpos): m/z=603 (M+H)$^+$
LC-MS (method 3): $R_t$=2.66 min
$^1$H-NMR (300 MHz, CDCl$_3$): δ=7.8-7.1 (m, 14H), 5.80-4.80 (m, 3H), 4.2-3.8 (m, 1H), 3.3-2.9 (m, 2H), 1.5 (s, 3H), 2.1-0.8 (m, 6H) ppm.

Example 55

Benzyl 2-({3-(2-tert.-butoxy-2-oxoethyl)-4-(4-cyanophenyl)-6-methyl-2-oxo-1-[3-(trifluoromethyl)phenyl]-1,2,3,4-tetrahydropyrimidin-5-yl}carbonyl)piperidine-1-carboxylate

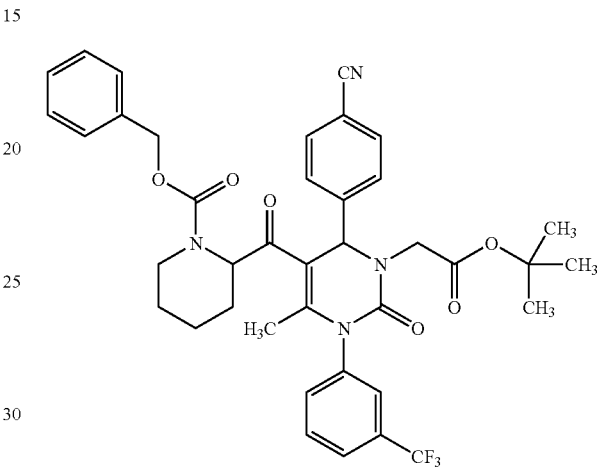

The title compound is prepared from Example 54 according to the procedure described for Example 26.

Yield: 53 mg (18% of th.)
LC-MS (method 3): $R_t$=3.08 min
HPLC (method 1): $R_t$=5.62 min, $\lambda_{max}$=234 nm
MS (ESIpos): m/z=712 (M+H)$^+$
$^1$H-NMR (300 MHz, CDCl$_3$): δ=7.72-7.12 (m, 13H), 5.64-4.56 (m, 5H), 4.18-3.92 (m, 1H), 3.52-3.12 (m, 2H), 2.35-0.73 (m, 6H), 1.52 (s, 3H), 1.48 (s, 9H) ppm.

Example 56

[5-({1-[(Benzyloxy)carbonyl]piperidin-2-yl}carbonyl)-6-(4-cyanophenyl)-4-methyl-2-oxo-3-[3-(trifluoromethyl)phenyl]-3,6-dihydropyrimidin-1(2H)-yl]acetic acid

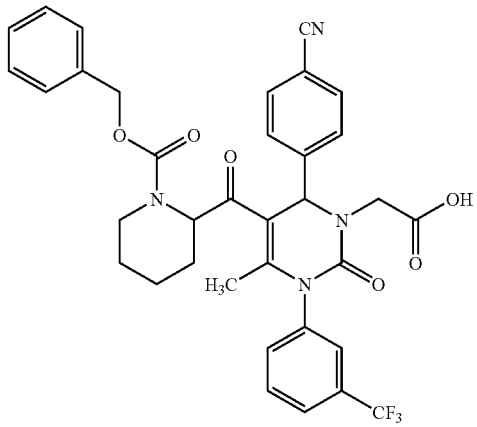

The title compound is prepared from Example 55 according to the procedure described for Example 30.

Yield: 35 mg (84% of th.)

HPLC (method 1): $R_t$=5.70 min, 254 nm $^1$H-NMR (300 MHz, DMSO-d$_6$): δ=12.5 (br s, 1H), 7.91-7.01 (m, 13H), 5.86 (d, 1H), 5.40-5.25 (m, 1H), 5.08 (s, 1H), 5.00-4.76 (m, 1H), 4.27 (m, 1H), 3.93-3.68 (m, 1H), 1.75 (s, 3H), 1.9-0.7 (m, 8H) ppm.

In analogy to the procedure for Example 2A, the following compounds are prepared:

| Example No. | Structure | Starting material | Yield [%] | $R_t$ [min] (method) | Mass [M + H]$^+$ |
|---|---|---|---|---|---|
| 57 | 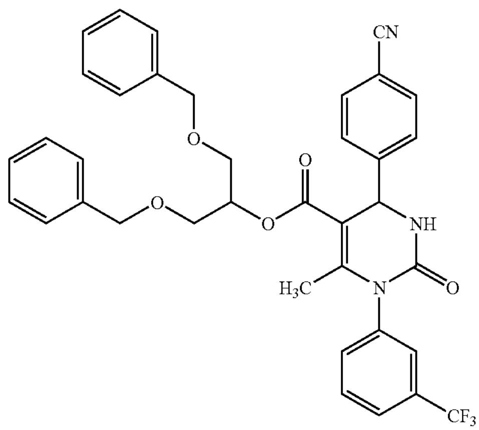 | Example 11A | 72 | 5.50 (1) | 656 |
| 58 | 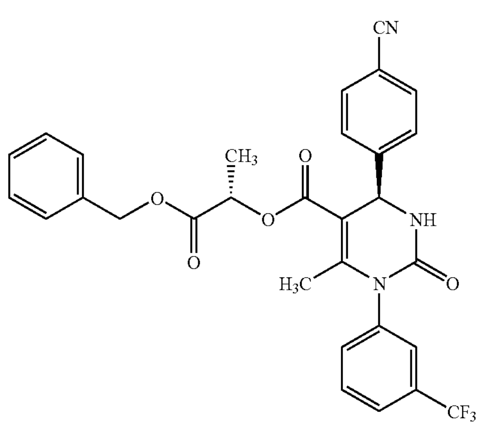 | Example 12A | 13 | 5.22 (6) | 564 |

Example 59

Benzyl tert.-butyl ({4-(4-cyanophenyl)-6-methyl-2-oxo-1-[3-(trifluoromethyl)phenyl]-1,2,3,4-tetrahydropyrimidin-5-yl}carbonyl)malonate

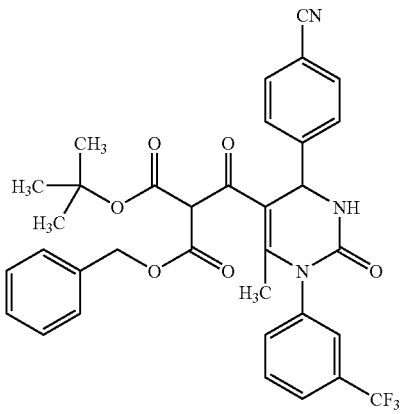

1401 mg (5.60 mmol) benzyl tert.-butyl malonate are dissolved in 4 ml tetrahydrofuran under an argon atmosphere. The solution is cooled to 0° C., 156 mg (3.92 mmol) sodium hydride are added, and the mixture is warmed to room temperature and stirred for 30 minutes. 580 mg (1.12 mmol) of Example 16A are added as a solution in 6 ml tetrahydrofuran. The reaction mixture is stirred under reflux overnight. The mixture is partitioned between ethyl acetate and 2 N hydrochloric acid, the organic phase is sequentially washed with water and saturated sodium chloride solution, dried over magnesium sulfate and evaporated in vacuo. The crude product is purified by column chromatography on silica gel (eluent: cyclohexane/ethyl acetate 2:1→0:1) and thereafter by RP-HPLC with a water/acetonitrile gradient.

Yield: 270 mg (38% of th.) as a mixture of diastereomers
$^1$H-NMR (300 MHz, DMSO-$d_6$): δ=1.21/1.36 (2s, 9H), 1.88/1.92 (2s, 3H), 4.95 (s, 1H), 5.10-5.23 (m, 2H), 5.47/5.51 (2d, 1H), 7.21-7.90 (m, 13H), 8.58/8.61 (2d, 1H) ppm.

Example 60

Benzyl 3-{4-(4-cyanophenyl)-6-methyl-2-oxo-1-[3-(trifluoromethyl)phenyl]-1,2,3,4-tetrahydropyrimidin-5-yl}-3-oxopropanoate

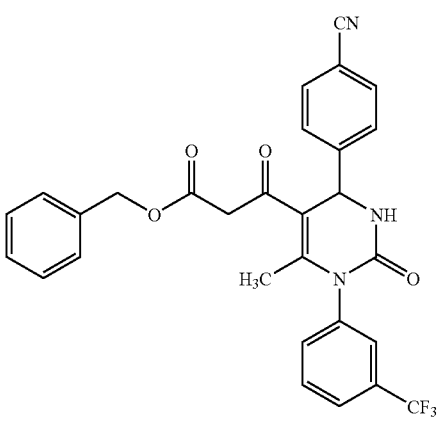

100 mg (0.16 mmol) of Example 59 are dissolved in 2 ml dichloromethane/trifluoroacetic acid (1:1) and stirred at room temperature for 1 hour. Volatiles are evaporated in vacuo and the crude product is purified by column chromatography on silica gel (eluent: cyclohexane/ethyl acetate 1:1).

Yield: 39 mg (42% of th.)
$^1$H-NMR (400 MHz, DMSO-$d_6$): δ=1.99 (s, 3H), 3.58 (d, 1H), 3.93 (d, 1H), 5.05 (s, 2H), 5.48 (d, 1H), 7.25-7.40 (m, 4H), 7.48-7.55 (br d, 1H), 7.60-7.73 (m, 4H), 7.80 (d, 1H), 7.86 (d, 2H), 8.55 (d, 1H) ppm.

Example 61

2-(Benzyloxy)-2-oxoethyl (4R)-4-(4-cyanophenyl)-6-methyl-2-oxo-1-[3-(trifluoromethyl)phenyl]-1,2,3,4-tetrahydropyrimidine-5-carboxylate

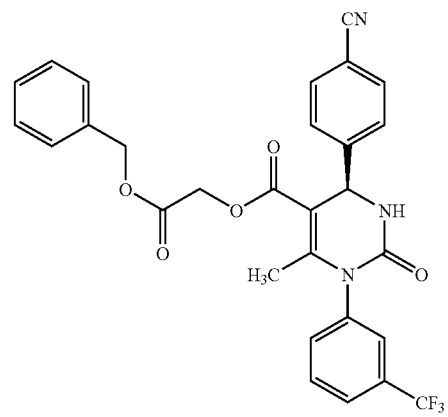

200 mg (0.50 mmol) of Example 6A are dissolved in 2.0 ml dimethylformamide. 456 mg (1.99 mmol) benzyl bromoacetate and 100 mg (1.00 mmol) triethylamine are added, and the mixture is stirred at room temperature for 2 hours. The reaction mixture is partitioned between ethyl acetate and 2 N hydrochloric acid, the organic layer is sequentially washed with water and saturated sodium chloride solution, dried over magnesium sulfate and evaporated to dryness in vacuo. The crude product is purified by column chromatography on silica gel (eluent: cyclohexane/ethyl acetate 1:1→0:1).

Yield: 260 mg (95% of th.)

$^1$H-NMR (200 MHz, DMSO-$d_6$): δ=2.05 (s, 3H), 4.74 (s, 1H), 5.12 (s, 1H), 5.41 (d, 1H), 7.28-7.42 (m, 5H), 7.53 (d, 1H), 7.61 (d, 2H), 7.65-7.75 (m, 2H), 7.77-7.86 (m, 3H), 8.45 (d, 1H) ppm.

In analogy to the procedure for Example 13A, the following compounds are prepared:

| Example No. | Structure | Starting material | Yield [%] | $R_t$ [min] (method) | Mass $[M + H]^+$ |
|---|---|---|---|---|---|
| 62 | 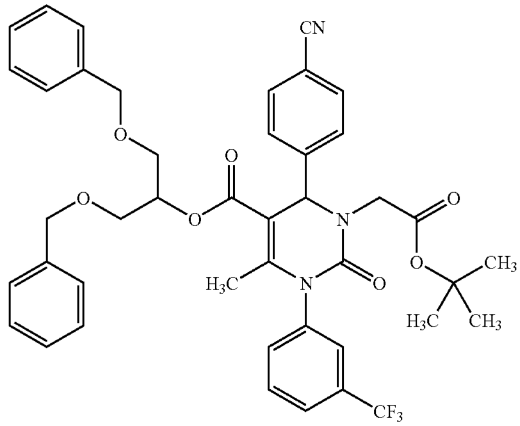 | Example 57 | 60 | 5.91 (1) | 770 |
| 63 | 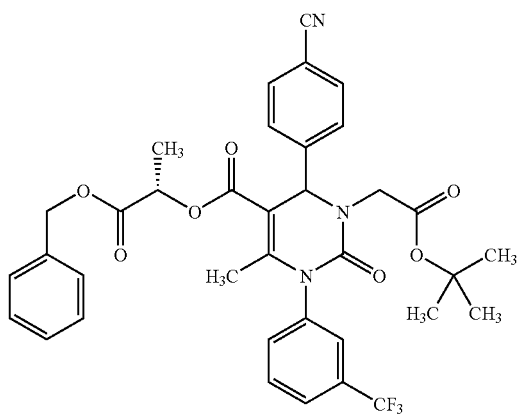 | Example 58 | 62 | 5.58 (1) | 678 |

Example 64

2-[(tert.-Butoxycarbonyl)amino]ethyl 3-(2-tert.-Butoxy-2-oxoethyl)-4-(4-cyanophenyl)-6-methyl-2-oxo-1-[3-(trifluoromethyl)phenyl]-1,2,3,4-tetrahydropyrimidine-5-carboxylate

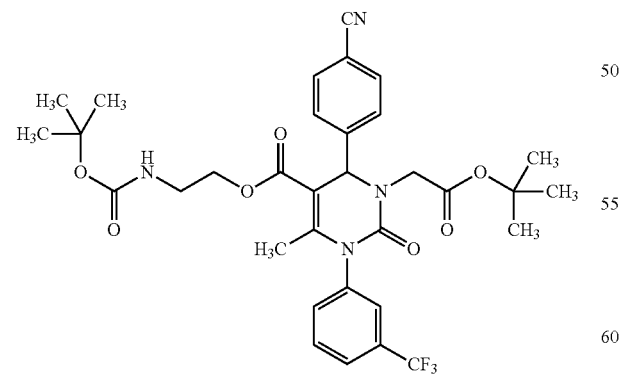

70 mg (0.12 mmol) of Example 15A and 521 mg (3.23 mmol) tert.-butyl-N-hydroxyethyl carbamate are reacted at 100° C. for 150 minutes. The reaction mixture is diluted with acetonitrile and purified using preparative RP-HPLC (eluent: acetonitrile/water gradient).

Yield: 41.9 mg (52% of th.)
$^1$H-NMR (200 MHz, DMSO-$d_6$): δ=1.28 (s, 9H), 1.36 (s, 9H), 2.05 (s, 3H), 3.03-3.18 (m, 2H), 3.80-4.1 (m, 4H), 5.10 (s, 1H), 6.82-6.95 (m, 1H), 7.60-7.93 (m, 8H) ppm.

Example 65

2-(2-Oxopyrrolidin-1-yl)ethyl 3-(2-tert.-butoxy-2-oxoethyl)-4-(4-cyanophenyl)-6-methyl-2-oxo-1-[3-(trifluoromethyl)phenyl]-1,2,3,4-tetrahydropyrimidine-5-carboxylate

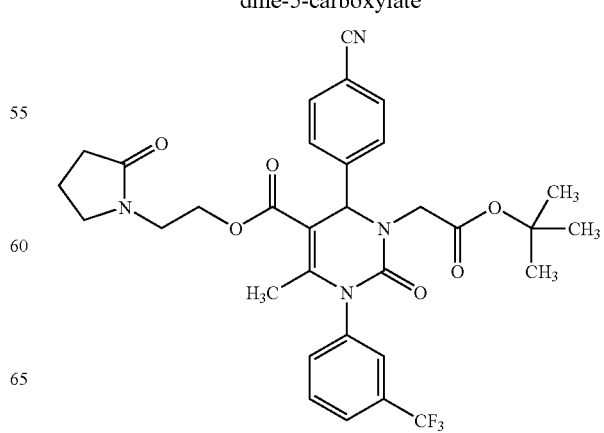

The title compound is synthesized in analogy to Example 64 from Example 15A using N-(2-hydroxyethyl)-2-pyrrolidone instead of tert.-butyl-N-hydroxyethyl carbamate.

Yield: 74% of th.

$^1$H-NMR (200 MHz, DMSO-d$_6$): δ=1.30 (s, 9H), 1.81 (q, 2H), 2.03 (s, 3H), 2.13 (t, 2H), 3.13-3.5 (m, 4H), 3.84 (d, 1H), 4.00-4.20 (m, 3H), 5.52 (s, 1H), 7.60-7.92 (m, 8H) ppm.

Example 66

2-(Benzyloxy)-2-oxoethyl 3-(2-tert.-butoxy-2-oxoethyl)-4-(4-cyanophenyl)-6-methyl-2-oxo-1-[3-(trifluoromethyl)phenyl]-1,2,3,4-tetrahydropyrimidine-5-carboxylate

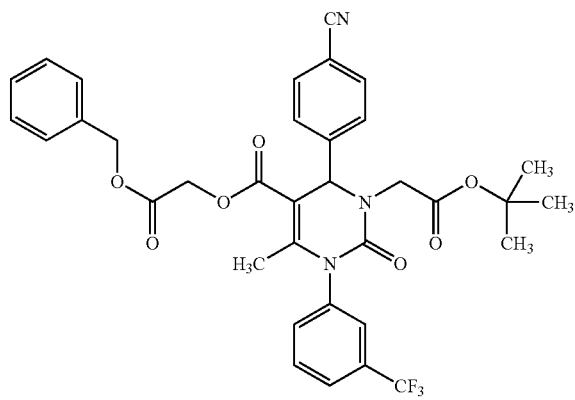

The title compound is synthesized in analogy to Example 64 from Example 15A using benzyl hydroxyacetate instead of tert.-butyl-N-hydroxyethyl carbamate.

Yield: 32% of th.

$^1$H-NMR (300 MHz, DMSO-d$_6$): δ=1.30 (s, 9H), 2.05 (s, 3H), 3.87 (d, 1H), 4.09 (d, 1H), 4.73 (d, 1H), 5.12 (s, 1H), 5.60 (s, 1H), 7.28-7.41 (m, 5H), 7.60-7.85 (m, 8H) ppm.

Example 67

[6-(4-Cyanophenyl)-4-methyl-2-oxo-5-{[2-(2-oxopyrrolidin-1-yl)ethoxy]carbonyl}-3-[3-(trifluoromethyl)phenyl]-3,6-dihydropyrimidin-1(2H)-yl]acetic acid

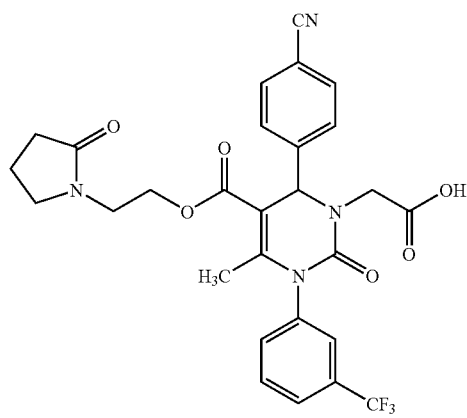

34.9 mg of Example 65 are dissolved in 2 ml dichloromethane/trifluoroacetic acid (1:1) and stirred at room temperature overnight. Volatiles are evaporated in vacuo and the remainder is purified by RP-HPLC using a water/acetonitrile gradient.

Yield: 18 mg (57% of th.)

$^1$H-NMR (200 MHz, DMSO-d$_6$): δ=1.81 (q, 2H), 2.02 (s, 3H), 2.13 (t, 2H), 3.10-3.55 (m, 4H), 3.72 (d, 1H), 4.00-4.22 (m, 3H), 5.52 (s, 1H), 7.58-7.93 (m, 8H), 12.75 (br s, 1H) ppm.

Example 68 tert.-Butyl [6-(4-cyanophenyl)-4-methyl-5-{[(methylsulfonyl)amino]carbonyl}-2-oxo-3-[3-(trifluoromethyl)phenyl]-3,6-dihydropyrimidin-1(2H)-yl]acetate

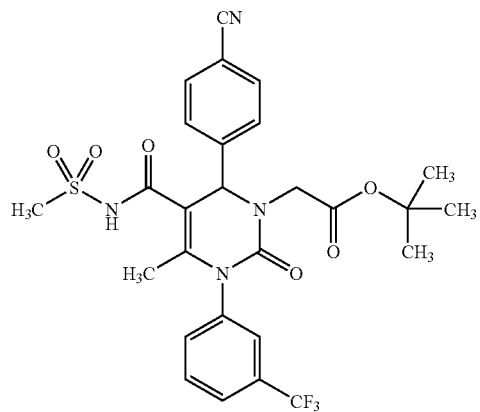

100 mg (0.19 mmol) of Example 14A, 36.9 mg (0.39 mmol) methanesulfonamide, 44.0 mg (0.21 mmol) dicyclohexylcarbodiimide and 26.1 mg (0.21 mmol) 4-N,N-dimethylaminopyridine are dissolved in dry dichloromethane (2 ml) and reacted overnight. The reaction mixture is filtered, the filtrate is sequentially washed with 2 M hydrochloric acid, water and saturated ammonium chloride solution, and the organic phase is dried over magnesium sulfate and evaporated to dryness. The crude product is purified by column chromatography on silica gel (eluent: cyclohexane/ethyl acetate/acetic acid 50:50:1).

Yield: 50 mg (41% of th.)

$^1$H-NMR (200 MHz, DMSO-d$_6$): δ=1.28 (s, 3H), 1.80 (s, 3H), 3.07 (s, 3H), 3.80 (d, 1H), 4.01 (d, 1H), 5.60 (s, 1H), 7.56-7.95 (m, 8H), 11.70 (br s, 1H) ppm.

In analogy to the procedure for Example 68, the following compounds are prepared:

| Example No. | Structure | Starting materials | Yield [%] | $R_t$ [min] (method) | Mass $[M + H]^+$ |
|---|---|---|---|---|---|
| 69 | 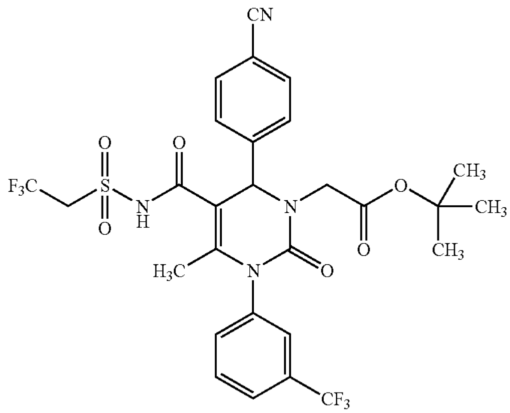 | Example 14A; 2,2,2-trifluoro-ethanesulfon-amide | 71 | 5.12 (1) | 661 |
| 70 | 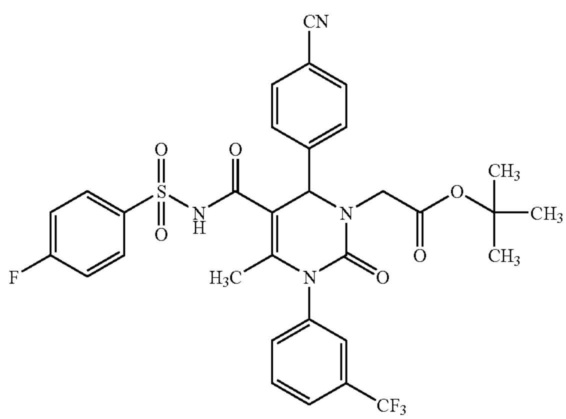 | Example 14A; 4-fluoro-benzene-sulfonamide | 43 | 5.17 (1) | 673 |
| 71 | 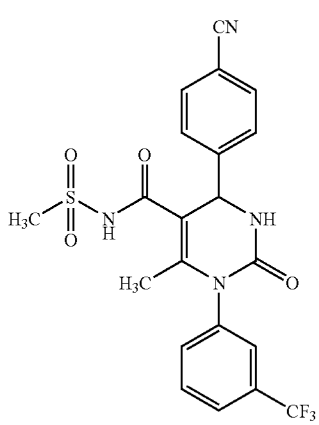 | Example 5A; methanesulfon-amide | 6 | 4.17 (6) | 479 |

| Example No. | Structure | Starting materials | Yield [%] | $R_t$ [min] (method) | Mass $[M + H]^+$ |
|---|---|---|---|---|---|
| 72 | 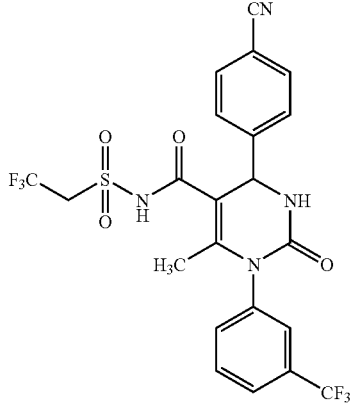 | Example 5A; 2,2,2-trifluoro-ethanesulfon-amide | 76 | 4.51 (6) | 547 |
| 73 | 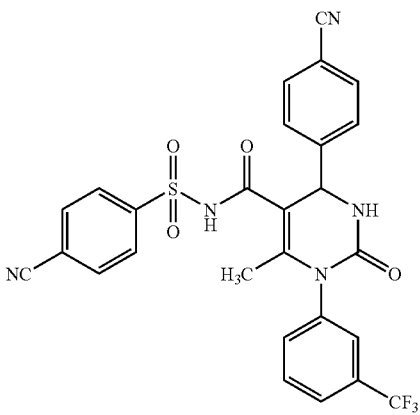 | Example 5A; 4-cyano-benzenesulfon-amide | 67 | 4.49 (6) | 566 |

Example 74

[6-(4-Cyanophenyl)-4-methyl-5-{[(methylsulfonyl)amino]carbonyl}-2-oxo-3-[3-(trifluoromethyl)phenyl]-3,6-dihydropyrimidin-1(2H)-yl]acetic acid

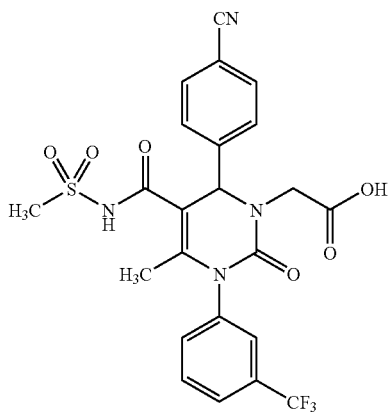

45.6 mg (0.08 mmol) of Example 68 are dissolved in 2 ml dichloromethane/trifluoroacetic acid (1:1) and stirred at room temperature for 1 hour. Volatiles are evaporated in vacuo and the remainder is purified by RP-HPLC with a water/acetonitrile gradient.

Yield: 13 mg (31% of th.)

$^1$H-NMR (200 MHz, DMSO-$d_6$): δ=1.28 (s, 3H), 1.78 (s, 3H), 3.11 (s, 3H), 3.69 (d, 1H), 4.10 (d, 1H), 5.62 (s, 1H), 7.52-8.10 (m, 8H), 11.70 (br s, 1H), 12.70 (br s, 1H) ppm.

In analogy to the procedure for Example 74, the following compounds are prepared:

| Example No. | Structure | Starting material | Yield [%] | $R_f$ [min] (method) | Mass [M + H]$^+$ |
|---|---|---|---|---|---|
| 75 | ![structure] | Example 69 | 41 | 4.56 (1) | 605 |
| 76 | ![structure] | Example 70 | 73 | 4.59 (1) | 617 |

Example 77 tert.-Butyl [6-(4-cyanophenyl)-5-(hydroxymethyl)-4-methyl-2-oxo-3-[3-(trifluoromethyl)phenyl]-3,6-dihydropyrimidin-1(2H)-yl]acetate

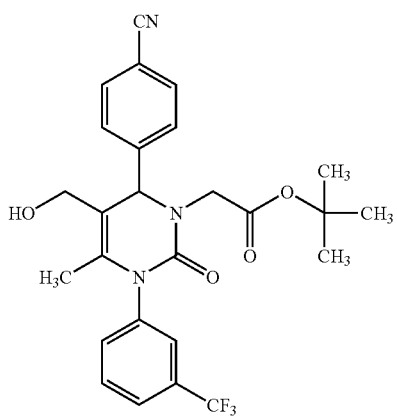

50 mg (0.13 mmol) of Example 1 are dissolved in 1 ml tetrahydrofuran, 10.8 mg (0.27 mmol) sodium hydride are added, and the mixture is stirred for 15 minutes at room temperature. 27 mg (0.14 mmol) tert.-butyl bromoacetate is added, and the mixture is stirred at room temperature for 1 hour. Saturated aq. ammonium chloride solution is added, and the reaction mixture is diluted with ethyl acetate. The organic phase is washed with water, dried over magnesium sulfate and evaporated to dryness. The crude product is purified by column chromatography over silica gel (eluent: cyclohexane/ethyl acetate).

Yield: 17.7 mg (27% of th.)

$^1$H-NMR (200 MHz, DMSO-$d_6$): δ=1.30 (s, 9H), 1.56 (s, 3H), 3.52 (dd, 1H), 3.62 (dd, 1H), 3.92-4.12 (m, 2H), 4.82 (t, 1H), 5.25 (s, 1H), 7.52-7.80 (m, 6H), 7.88 (d, 2H) ppm.

Example 78

3-{4-(4-Cyanophenyl)-6-methyl-2-oxo-1-[3-(trifluoromethyl)phenyl]-1,2,3,4-tetrahydropyrimidin-5-yl}propanoic acid

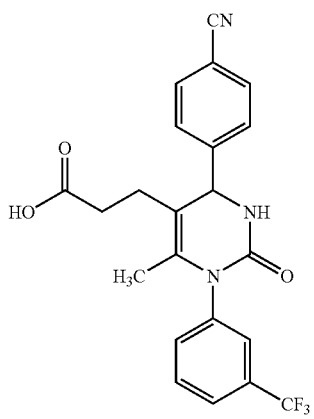

45.0 mg (0.057 mmol) of Example 17A und 5.00 mg palladium on charcoal (10%) are suspended in 5 ml ethanol and hydrogenated under 1 atm hydrogen at room temperature for 12 minutes. The reaction mixture is filtered over celite and the residue is washed with ethanol. The filtrate is evaporated to dryness in vacuo and the remainder is heated without solvent at 130° C. under an argon atmosphere for 20 minutes. The crude product is purified by RP-HPLC with a water/acetonitrile gradient.

Yield: 9 mg (26% of th.)

$^1$H-NMR (300 MHz, DMSO-$d_6$): δ=1.53 (s, 3H), 1.92-2.42 (m, 4H), 4.93 (s, 1H), 7.50-7.94 (m, 9H), 12.08 (br s, 1H) ppm.

Example 79

({(4R)-4-(4-Cyanophenyl)-6-methyl-2-oxo-1-[3-(trifluoromethyl)phenyl]-1,2,3,4-tetrahydropyrimidin-5-yl}methyl)malonic acid

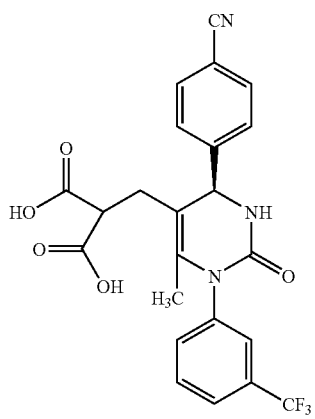

200 mg (0.25 mmol) of Example 19A und 5.0 mg palladium on charcoal (10%) are suspended in 10 ml ethanol and hydrogenated under 1 atm hydrogen at room temperature for 15 minutes. The reaction mixture is filtered over celite and the residue is washed with ethanol. The filtrate is evaporated to dryness in vacuo and the crude product is purified by RP-HPLC with a water/acetonitrile gradient.

Yield: 87 mg (72% of th.)

$^1$H-NMR (300 MHz, DMSO-$d_6$): δ=1.5 (s, 3H), 2.2 (dd, 2H), 2.6 (dd, 2H), 3.5 (dd, 1H), 5.0 (d, 1H), 7.5 (m, 2H), 7.6-7.7 (m, 4H), 7.8 (d, 1H), 7.9 (m, 2H), 12.8 (br s, 2H) ppm.

Example 80

3-{(4R)-4-(4-Cyanophenyl)-6-methyl-2-oxo-1-[3-(trifluoromethyl)phenyl]-1,2,3,4-tetrahydropyrimidin-5-yl}propanoic acid

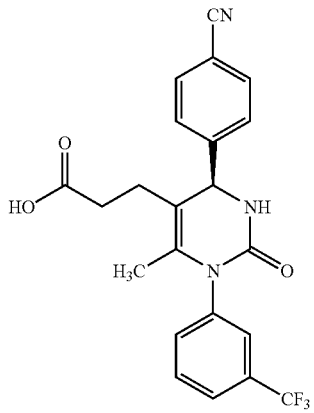

40 mg (0.08 mmol) of Example 79 are heated without solvent at 130° C. under an argon atmosphere for 20 minutes. The crude product is purified by column chromatography (silica, eluent: dichloromethane/methanol 20:1).

Yield: 36 mg (99% of th.)

$^1$H-NMR (300 MHz, DMSO-d$_6$): δ=1.5 (s, 3H), 1.9-2.2 (m, 2H), 2.3-2.4 (m, 2H), 4.9 (d, 1H), 7.50-7.7 (m, 6H), 7.8 (d, 1H), 7.9 (m, 2H), 12.1 (br s, 1H) ppm.

Examples 81 and 82

4-{(4R)-5-(1-Hydroxyethyl)-6-methyl-2-oxo-1-[3-(trifluoromethyl)phenyl]-1,2,3,4-tetrahydropyrimidin-4-yl}benzonitrile

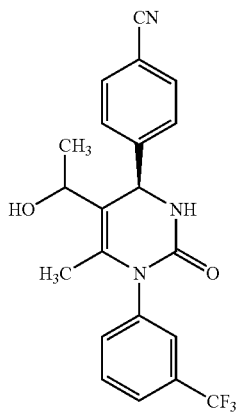

300 mg (0.75 mmol) of Example 18A are dissolved in 5 ml tetrahydrofuran. At 0° C., 28.5 mg (0.75 mmol) lithium aluminium hydride (as 1 M solution in tetrahydrofuran) are added slowly. The dark-red solution is stirred at 0° C. for 30 minutes, then water is added. The pH is adjusted to 3-4 with 1 N hydrochloric acid. The crude product is extracted with ethyl acetate and purified and separated by column chromatography (silica, eluent: dichloromethane/methanol 40:1).

Example 81

(Diastereomer I)

Yield: 15 mg (5% of th.)

$^1$H-NMR (400 MHz, DMSO-d$_6$): δ=1.2 (d, 3H), 1.6 (s, 3H), 4.6 (m, 2H), 4.9 (d, 1H), 7.4 (m, 1H), 7.5 (m, 1H), 7.7 (m, 4H), 7.8 (m, 2H), 7.9 (d, 1H) ppm.

Example 82

(Diastereomer II)

Yield: 15 mg (5% of th.)

$^1$H-NMR (300 MHz, DMSO-d$_6$): δ=0.8 (d, 3H), 1.6 (s, 3H), 4.6 (m, 1H), 5.0 (d, 1H), 5.1 (d, 1H), 7.5 (m, 1H), 7.6-7.7 (m, 5H), 7.8 (d, 1H), 7.9 (m, 2H) ppm.

Example 83

4-{5-(4-Bromobenzoyl)-6-methyl-2-oxo-1-[3-(trifluoromethyl)phenyl]-1,2,3,4-tetrahydropyrimidin-4-yl}benzonitrile

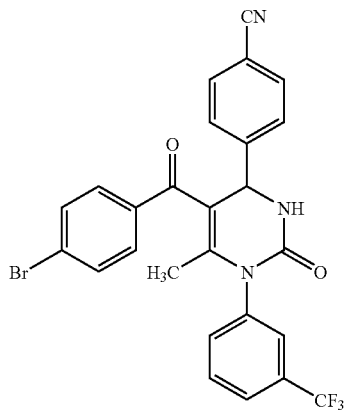

4.23 g (20.74 mmol) N-[3-(trifluoromethyl)phenyl]urea, 2.72 g (20.74 mmol) 4-cyanobenzaldehyde, 5.00 g (20.74 mmol) 1-(4-bromophenyl)butane-1,3-dione and 6.5 g polyphosphoric acid ethyl ester are suspended in 50 ml of tetrahydrofuran. The mixture is stirred at reflux for 20 hours. After cooling down to room temperature, the solvent is removed in vacuo and the residue is purified by column chromatography on silica with cyclohexane/ethyl acetate mixtures as eluent.

Yield: 5.32 g (45% of th.)

$^1$H-NMR (400 MHz, DMSO-d$_6$): δ=1.4 (s, 3H), 5.4 (d, 1H), 7.6-7.9 (m, 12H), 8.4 (d, 1H) ppm.

Example 84 tert.-Butyl [5-(4-bromobenzoyl)-6-(4-cyanophenyl)-4-methyl-2-oxo-3-[3-(trifluoromethyl)phenyl]-3,6-dihydropyrimidin-1(2H)-yl]acetate

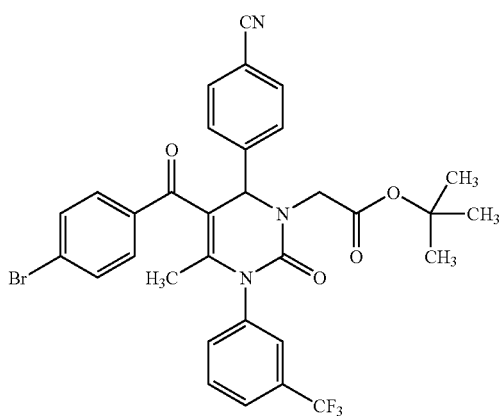

5.32 g (9.85 mmol) of Example 83 are dissolved in 150 ml tetrahydrofuran, and 0.98 g (24.61 mmol) sodium hydride (60% suspension in mineral oil) are added slowly. After stirring for one hour at room temperature, 2.88 g (14.77 mmol) tert.-butyl bromoacetate are added. After stirring at room temperature for one hour, the mixture is quenched with water, the solvent is removed in vacuo and the residue is purified by column chromatography (silica, eluent: cyclohexane/ethyl acetate 10:1, 5:1).

Yield: 3.12 g (48% of th.)

$^1$H-NMR (300 MHz, DMSO-$d_6$): δ=1.3 (s, 9H), 1.4 (s, 3H), 3.9 (d, 1H), 4.1 (d, 1H), 5.6 (s, 1H), 7.7 (m, 7H), 7.8 (m, 5H) ppm.

Example 85

[5-(4-Bromobenzoyl)-6-(4-cyanophenyl)-4-methyl-2-oxo-3-[3-(trifluoromethyl)phenyl]-3,6-dihydropyrimidin-1(2H)-yl]acetic acid

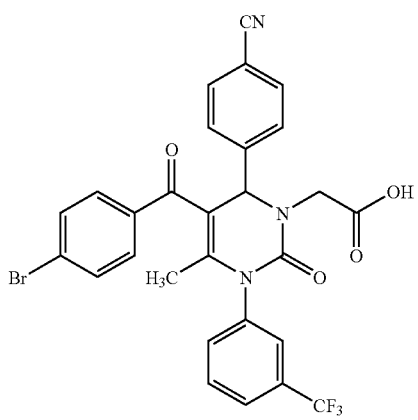

100 mg (0.15 mmol) of Example 84 are dissolved in 10 ml dichloromethane and 0.25 ml trifluoroacetic acid, and the mixture is stirred at room temperature overnight. Volatiles are evaporated in vacuo and the remainder is purified by RP-HPLC using a water/acetonitrile gradient.

Yield: 47 mg (52% of th.)

$^1$H-NMR (300 MHz, DMSO-$d_6$): δ=1.4 (s, 3H), 3.7 (d, 1H), 4.2 (d, 1H), 5.7 (s, 1H), 7.7 (m, 8H), 7.8 (m, 4H) ppm.

Example 86 tert.-Butyl [5-(biphenyl-4-ylcarbonyl)-6-(4-cyanophenyl)-4-methyl-2-oxo-3-[3-(trifluoromethyl)phenyl]-3,6-dihydropyrimidin-1(2H)-yl]acetate

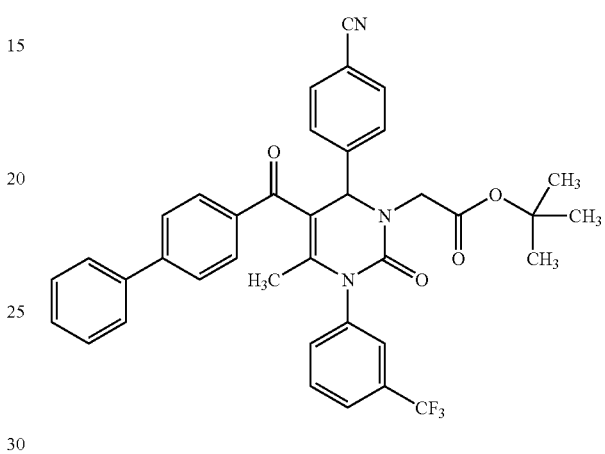

100 mg (0.15 mmol) of Example 84 are dissolved in 5 ml N,N-dimethylformamide under an argon atmosphere, and 19 mg (0.15 mmol) phenylboronic acid, 100 mg (0.31 mmol) cesium carbonate and 5 mg dichloro[bis(triphenylphosphino)]palladium are added. The reaction mixture is stirred at 120° C. for 18 hours. The product is purified by RP-HPLC using a water/acetonitrile gradient.

Yield: 39 mg (39% of th.)

$^1$H-NMR (300 MHz, DMSO-$d_6$): δ=1.3 (s, 9H), 1.5 (s, 3H), 3.9 (d, 1H), 4.2 (d, 1H), 5.7 (s, 1H), 7.5 (m, 3H), 7.7-7.9 (m, 14H) ppm.

Example 87

[5-(Biphenyl-4-ylcarbonyl)-6-(4-cyanophenyl)-4-methyl-2-oxo-3-[3-(trifluoromethyl)phenyl]-3,6-dihydropyrimidin-1(2H)-yl]acetic acid

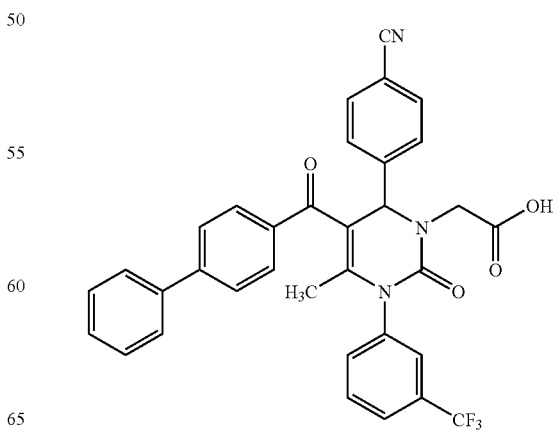

30 mg (0.05 mmol) of Example 86 are dissolved in 2 ml dichloromethane and 0.07 ml trifluoroacetic acid, and the mixture is stirred at room temperature overnight. Volatiles are evaporated in vacuo and the remainder is purified by RP-HPLC using a water/acetonitrile gradient.

Yield: 23 mg (83% of th.)

$^1$H-NMR (300 MHz, DMSO-$d_6$): δ=1.5 (s, 3H), 3.7 (d, 1H), 4.3 (d, 1H), 5.7 (s, 1H), 7.4-7.5 (m, 3H), 7.6-7.9 (m, 14H) ppm.

Example 88

4-{5-(4-Nitrobenzoyl)-6-methyl-2-oxo-1-[3-(trifluoromethyl)phenyl]-1,2,3,4-tetrahydropyrimidin-4-yl}benzonitrile

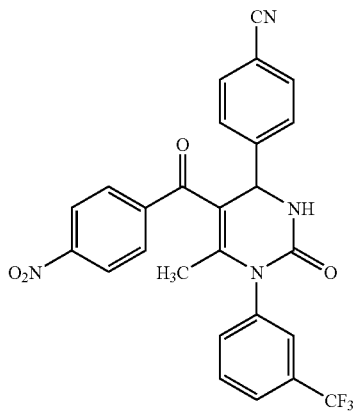

9.85 g (48.27 mmol) N-[3-(trifluoromethyl)phenyl]urea, 6.33 g (48.27 mmol) 4-cyanobenzaldehyde, 10.00 g (48.27 mmol) 1-(4-nitrophenyl)butane-1,3-dione and 15 g polyphosphoric acid ethyl ester are suspended in 100 ml of tetrahydrofuran. The mixture is stirred at reflux for 20 hours. After cooling down to room temperature, the solvent is removed in vacuo and the residue is purified by column chromatography on silica with cyclohexane/ethyl acetate mixtures as eluent.

Yield: 7.84 g (32% of th.)

$^1$H-NMR (400 MHz, DMSO-$d_6$): δ=1.4 (s, 3H), 5.4 (d, 1H), 7.6 (m, 3H), 7.7 (m, 1H), 7.8 (m, 2H), 7.8 (m, 1H), 7.9 (m, 3H), 8.3 (m, 2H), 8.5 (d, 1H) ppm.

Example 89 tert.-Butyl [5-(4-nitrobenzoyl)-6-(4-cyanophenyl)-4-methyl-2-oxo-3-[3-(trifluoromethyl)phenyl]-3,6-dihydropyrimidin-1(2H)-yl]acetate

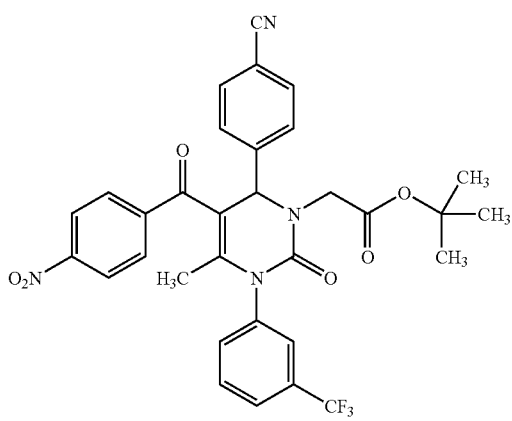

5.27 g (10.41 mmol) of Example 88 are dissolved in 150 ml tetrahydrofuran, and 1.04 g (26.02 mmol) sodium hydride (60% suspension in mineral oil) are added slowly. After stirring for one hour at room temperature, 3.04 g (15.61 mmol) tert.-butyl bromoacetate are added. After stirring at room temperature for one hour, the mixture is quenched with water, the solvent is removed in vacuo and the residue is purified by column chromatography (silica, eluent: cyclohexane/ethyl acetate 10:1, 5:1).

Yield: 0.16 g (3% of th.)

$^1$H-NMR (300 MHz, DMSO-$d_6$): δ=1.3 (s, 9H), 1.5 (s, 3H), 3.9 (d, 1H), 4.2 (d, 1H), 5.6 (s, 1H), 7.7 (m, 4H), 7.8-7.9 (m, 6H), 8.3 (m, 2H) ppm.

Example 90 tert.-Butyl [5-(4-aminobenzoyl)-6-(4-cyanophenyl)-4-methyl-2-oxo-3-[3-(trifluoromethyl)phenyl]-3,6-dihydropyrimidin-1(2H)-yl]acetate

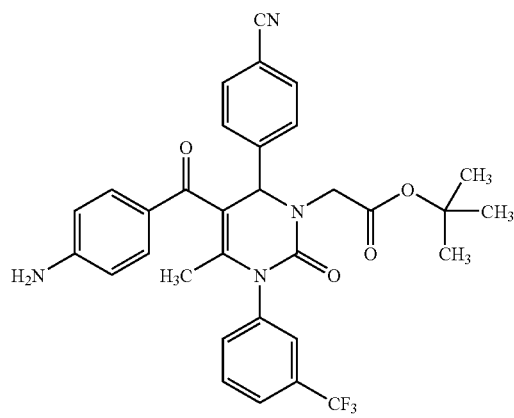

160 mg (0.26 mmol) of Example 89 und 5 mg palladium on charcoal (10%) are suspended in 20 ml tetrahydrofuran and hydrogenated under 1 atm hydrogen at room temperature for 18 hours. The reaction mixture is filtered over celite, the filtrate is evaporated to dryness in vacuo and the crude product is purified by RP-HPLC with a water/acetonitrile gradient.

Yield: 69 mg (45% of th.)

$^1$H-NMR (300 MHz, DMSO-$d_6$): δ=1.3 (s, 9H), 1.4 (s, 3H), 3.7 (d, 1H), 4.1 (d, 1H), 5.6 (s, 1H), 6.2 (m, 2H), 6.5 (m, 2H), 7.5 (m, 2H), 7.6 (m, 2H), 7.7 (m, 2H), 7.8 (m, 4H) ppm.

Example 91 tert.-Butyl [(6R)-6-(4-cyanophenyl)-5-(cyclopropyl-carbonyl)-4-methyl-2-oxo-3-[3-(trifluoromethyl)phenyl]-3,6-dihydropyrimidin-1(2H)-yl]acetate

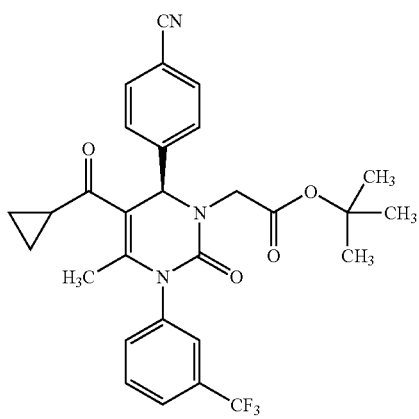

The title compound is prepared from Example 23 according to the procedure described for Example 26.

Yield: 108 mg (85% of th.)

$^1$H-NMR (300 MHz, DMSO-d$_6$): δ=7.90-7.58 (m, 8H), 5.74-5.67 (m, 1H), 4.15-3.85 (m, 2H), 2.30-2.19 (m, 1H), 1.97 (s, 3H), 1.30 (s, 9H), 0.90-0.73 (m, 4H) ppm.

Example 92

[(6R)-6-(4-Cyanophenyl)-5-(cyclopropylcarbonyl)-4-methyl-2-oxo-3-[3-(trifluoromethyl)phenyl]-3,6-dihydropyrimidin-1(2H)-yl]acetic acid

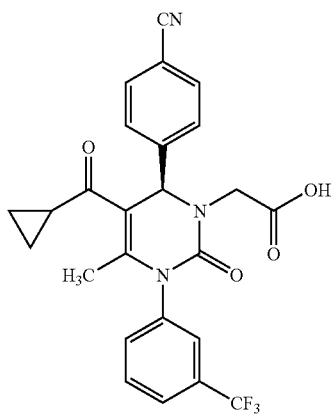

The title compound is prepared from Example 91 according to the procedure described for Example 30.

Yield: 80 mg (89% of th.)

$^1$H-NMR (300 MHz, DMSO-d$_6$): δ=12.62 (br s, 1H), 7.91-7.55 (m, 8H), 5.77 (s, 1H), 4.23-3.70 (m, 2H), 2.32-2.19 (m, 1H), 1.97 (s, 3H), 0.94-0.72 (m, 4H) ppm.

Example 93

4-{5-[(2,2-Dimethyl-1,3-dioxolan-4-yl)carbonyl]-6-methyl-2-oxo-1-[3-(trifluoromethyl)phenyl]-1,2,3,4-tetrahydropyrimidin-4-yl}benzonitrile

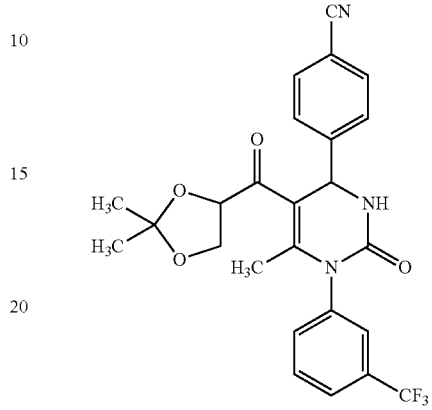

To a stirred solution of Example 20A (120 mg, 0.64 mmol), N-[3-(trifluoromethyl)phenyl]urea (109 mg, 0.54 mmol) and 4-cyanobenzaldehyde (84.5 mg, 0.64 mmol) in methyl tert.-butyl ether (5 ml) is added 2,4,6-tripropyl-1,3,5,2,4,6-trioxatriphosphinane 2,4,6-trioxide (683 mg, 1 mmol). The solution is refluxed overnight under argon, then cooled to room temperature, quenched with water (200 ml) and extracted with methyl tert.-butyl ether (3×100 ml). The combined organic phases are washed with brine, dried over anhydrous magnesium sulfate, filtered and concentrated. The residue is purified by preparative HPLC.

Yield: 15 mg (5% of th.)

$^1$H-NMR (300 MHz, DMSO-d$_6$): δ=8.48 (m, 1H), 8.00-7.38 (m, 8H), 5.66-5.40 (m, 1H), 4.99-4.74 (m, 1H), 4.16-3.85 (m, 2H), 1.94 (d, 3H), 1.35-1.11 (m, 6H) ppm.

Example 94

4-{5-(Cyclohexylcarbonyl)-3-[2-(diethylamino)ethyl]-6-methyl-2-oxo-1-[3-(trifluoromethyl)phenyl]-1,2,3,4-tetrahydropyrimidin-4-yl}benzonitrile

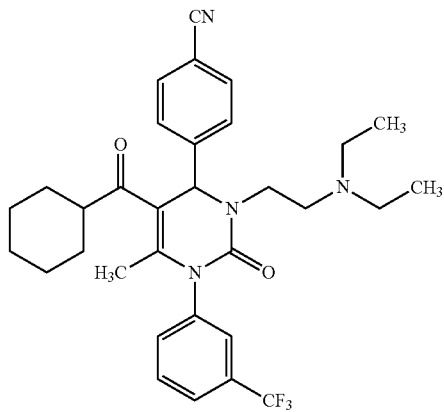

To a stirred solution of Example 21 (780 mg, 1.67 mmol) in THF (25 ml) is added sodium hydride (60% dispersion in mineral oil; 653 mg, 2.53 mmol). The mixture is stirred for 1 hour at room temperature, then 2-bromo-N,N-diethylethanamine (653 mg, 2.53 mmol) is added, and the solution is stirred overnight (16 h) at room temperature. The reaction mixture is quenched with methanol (10 ml), concentrated, and the crude product is purified by preparative HPLC.

Yield: 175 mg (18% of th.)

$^1$H-NMR (400 MHz, DMSO-$d_6$): δ=7.98-7.50 (m, 8H), 5.71 (s, 1H), 3.66-3.54 (m, 2H), 3.10-3.00 (m, 2H), 2.86-2.76 (m, 1H), 2.69-2.30 (m, 4H), 1.77 (s, 3H), 1.73-1.00 (m, 10H), 0.93 (t, 6H) ppm.

Example 95

4-{5-(Cyclopropylcarbonyl)-3-[2-(diethylamino)ethyl]-6-methyl-2-oxo-1-[3-(trifluoromethyl)phenyl]-1,2,3,4-tetrahydropyrimidin-4-yl}benzonitrile

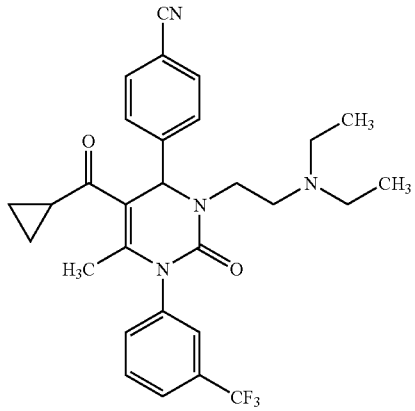

The title compound is prepared from Example 22 according to the procedure described for Example 94.

Yield: 235 mg (59% of th.)

$^1$H-NMR (400 MHz, DMSO-$d_6$): δ=7.93-7.54 (m, 8H), 5.81 (s, 1H), 3.68-3.59 (m, 2H), 3.12-3.01 (m, 2H), 2.60-2.56 (m, 5H), 1.92 (s, 3H), 0.97-0.78 (m, 10H) ppm.

Example 96 tert.-Butyl [6-(4-cyanophenyl)-5-[(2,2-dimethyl-1,3-dioxolan-4-yl)carbonyl]4-methyl-2-oxo-3-[3-(trifluoromethyl)phenyl]-3,6-dihydropyrimidin-1(2H)-yl]acetate

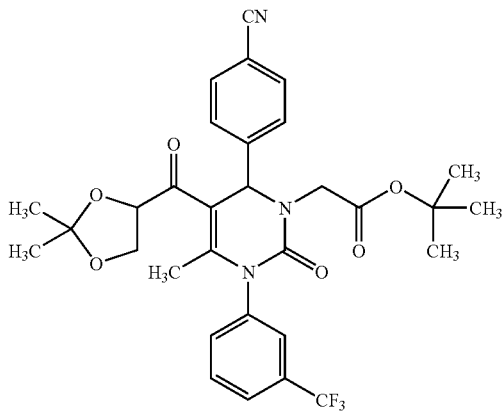

The title compound is prepared from Example 93 according to the procedure described for Example 26.

Yield: 145 mg (62% of th.)

$^1$H-NMR (400 MHz, DMSO-$d_6$): δ=7.92-7.56 (m, 8H), 5.77 and 5.62 (s, 1H; diastereomers A and B), 4.97 and 4.82 (t, 1H; diastereomers A and B), 4.19-3.83 (m, 4H), 1.96 and 1.93 (s, 3H; diastereomers A and B), 1.34-1.20 (m, 15H) ppm.

Example 97

Methyl [6-(4-cyanophenyl)-5-[(2,2-dimethyl-1,3-dioxolan-4-yl)carbonyl]-4-methyl-2-oxo-3-[3-(trifluoromethyl)phenyl]-3,6-dihydropyrimidin-1(2H)-yl]acetate

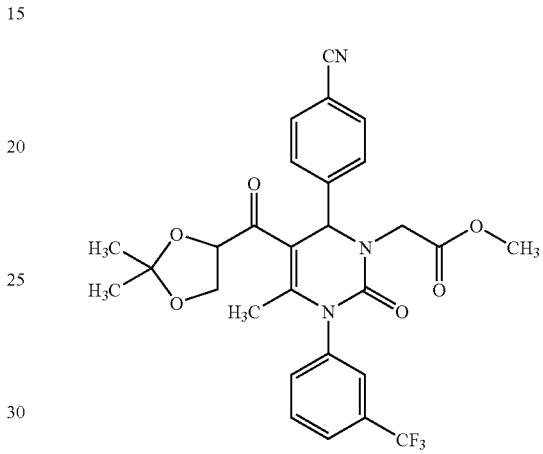

The title compound is prepared from Example 93 according to the procedure described for Example 26.

Yield: 77 mg (65% of th.)

$^1$H-NMR (300 MHz, DMSO-$d_6$): δ 7.94-7.55 (m, 8H), 5.81 and 5.66 (s, 1H; 2 diastereomers), 4.99 and 4.87 (t, 1H; 2 diastereomers), 4.35-3.85 (m, 4H), 3.57 and 3.55 (s, 3H; 2 diastereomers), 1.95 and 1.92 (s, 3H; 2 diastereomers), 1.25 (dd, 6H) ppm.

Example 98

4-{(4R)-5-(Cyclopropylcarbonyl)-3-[2-(diethylamino)ethyl]-6-methyl-2-oxo-1-[3-(trifluoromethyl)phenyl]-1,2,3,4-tetrahydropyrimidin-4-yl}benzonitrile

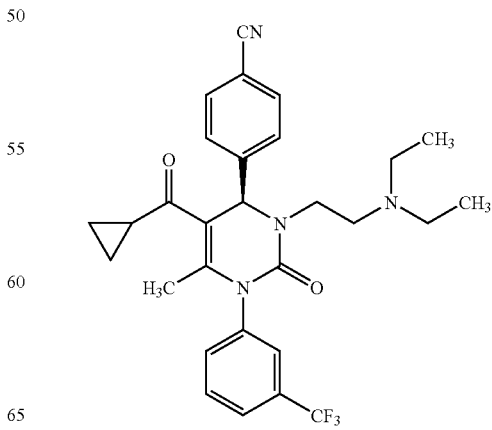

The enantiomers of Example 95 are separated by preparative HPLC on a chiral phase [Daicel Chiralpak AD-H, 5 μm; 250 mm×20 mm; eluent: 80:20 isohexane/isopropanol with 0.2% diethylamine; flow 15 ml/min; temperature 25° C.; detection 220 nm].

$R_t$=4.58 min. [Daicel Chiralpak AD-H, 5 μm; 250 mm×4.6 mm; eluent: 80:20 isohexane/isopropanol with 0.2% diethylamine; flow 1.0 ml/min; temperature 35° C.; detection 220 nm].

Example 99

4-{(4R)-5-(Cyclohexylcarbonyl)-3-[2-(diethylamino)ethyl]-6-methyl-2-oxo-1-[3-(trifluoromethyl)phenyl]-1,2,3,4-tetrahydropyrimidin-4-yl}benzonitrile

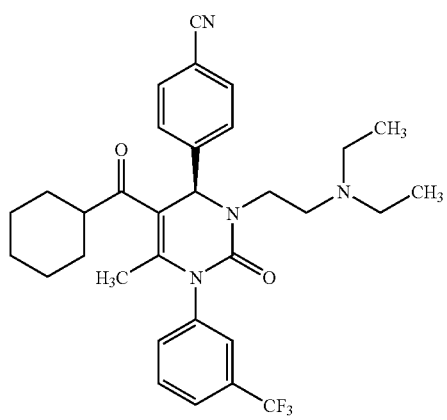

The enantiomers of Example 94 are separated by preparative HPLC on a chiral phase [Daicel Chiralpak AD-H, 5 μm; 250 mm×20 mm; eluent: 80:20 isohexane/isopropanol with 0.2% diethylamine; flow 15 ml/min; temperature 25° C.; detection 220 nm].

$R_t$=4.24 min. [Daicel Chiralpak AD-H, 5 μm; 250 mm×4.6 mm; eluent: 80:20 isohexane/isopropanol with 0.2% diethylamine; flow 1.0 ml/min; temperature 35° C.; detection 220 nm].

C. Operative Examples Relating to Pharmaceutical Compositions

The compounds according to the invention can be converted into pharmaceutical preparations as follows:

Tablet
Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension
Composition:

1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation:

The Rhodigel is suspended in ethanol and the active component is added to the suspension. The water is added with stirring. Stirring is continued for about 6 h until the swelling of the Rhodigel is complete.

We claim:
1. A compound of the formula (I)

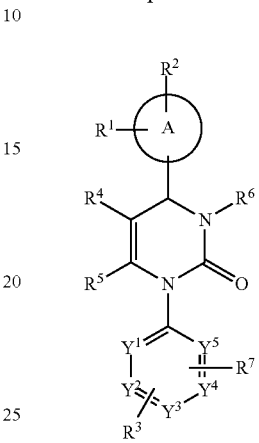

wherein
A represents an aryl or heteroaryl ring;
$R^1$, $R^2$, and $R^3$ independently from each other represent hydrogen, halogen, nitro, cyano, $C_1$-$C_6$-alkyl, hydroxy, or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxyl, and $C_1$-$C_4$-alkoxy;
$R^4$ represents: $C_1$-$C_6$-alkyl, which can be substituted by up to three radicals independently selected from the group consisting of hydroxy, $C_1$-$C_6$-alkoxycarbonyl, and hydroxycarbonyl; $C_3$-$C_8$-cycloalkylcarbonyl, which can be substituted by up to three radicals independently selected from the group consisting of $C_1$-$C_6$-alkyl, hydroxy, oxo, $C_1$-$C_6$-alkoxycarbonyl, and hydroxycarbonyl; $C_1$-$C_6$-alkylcarbonyl, which is substituted by phenyl-$C_1$-$C_6$-alkoxy or phenyl-$C_1$-$C_6$-alkoxycarbonyl, which in the phenyl moiety can be substituted by halogen, $C_1$-$C_6$-alkyl, hydroxy, $C_1$-$C_6$-alkoxy, $C_1$-$C_6$-alkoxycarbonyl, or hydroxycarbonyl; $C_6$-$C_{10}$-arylcarbonyl, which is substituted by one, two, or three radicals independently selected from the group consisting of halogen, cyano, nitro, $C_1$-$C_6$-alkyl, trifluoromethyl, hydroxy, $C_1$-$C_6$-alkoxy, trifluoromethoxy, amino, $C_1$-$C_6$-alkoxycarbonyl, hydroxycarbonyl, and phenyl; $C_1$-$C_6$-alkoxycarbonyl, which is substituted by one or two radicals independently selected from the group consisting of phenyl-$C_1$-$C_6$-alkoxy, phenyl-$C_1$-$C_6$-alkoxycarbonyl, $C_1$-$C_6$-alkoxy, $C_1$-$C_6$-alkoxycarbonylamino, and 5- or 6-membered heterocyclyl, wherein $C_1$-$C_6$-alkoxy is further substituted by $C_1$-$C_6$-alkoxycarbonyl, or hydroxycarbonyl, and 5- or 6-membered heterocyclyl is further substituted by hydroxy, $C_1$-$C_6$-alkoxycarbonyl, or hydroxycarbonyl; heteroarylcarbonyl, which is substituted by one or two radicals independently selected from the group consisting of hydroxy, amino, halogen, $C_1$-$C_6$-alkoxy, $C_1$-$C_6$-alkoxycarbonyl, and hydroxycarbonyl, and which can additionally be substituted by $C_1$-$C_6$-alkyl; mono- or di-$C_1$-$C_6$-alkylaminocarbonyl, wherein the alkyl moiety or at least one alkyl moiety, respectively, is substituted by $C_6$-$C_{10}$-aryl, which can be further substituted by up to three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl, and hydroxycarbonyl; $C_6$-$C_{10}$-arylaminocarbonyl or N—($C_1$-$C_6$-alkyl)-N—($C_6$-$C_{10}$-aryl)aminocarbonyl, wherein aryl is substituted by one, two, or three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl, and hydroxycarbonyl, and wherein alkyl, when present, can be substituted by up to three radicals independently selected from the group consisting of hydroxy, $C_1$-$C_6$-alkoxy, $C_1$-$C_6$-alkoxycarbonyl, and hydroxycarbonyl; $C_3$-$C_8$-cycloalkylaminocarbonyl or N—($C_1$-$C_6$-alkyl)-N—($C_3$-$C_8$-cycloalkyl)aminocarbonyl, wherein cycloalkyl can be substituted by up to three radicals independently selected from the group consisting of $C_1$-$C_6$-alkyl, hydroxy, oxo, $C_1$-$C_6$-alkoxycarbonyl, and hydroxycarbonyl, and wherein alkyl, when present, can be substituted by up to three radicals independently selected from the group consisting of hydroxy, $C_1$-$C_6$-alkoxy, $C_1$-$C_6$-alkoxycarbonyl, and hydroxycarbonyl; heterocyclylcarbonyl, which is substituted by one, two, or three radicals independently selected from the group consisting of $C_1$-$C_6$-alkyl, hydroxy, oxo, $C_1$-$C_6$-alkoxy, $C_1$-$C_6$-alkoxycarbonyl, phenyl-$C_1$-$C_6$-alkoxycarbonyl, hydroxycarbonyl, 5- or 6-membered heterocyclyl, 5- or 6-membered heteroaryl, and $C_6$-$C_{10}$-aryl, wherein $C_1$-$C_6$-alkyl is further substituted by hydroxy, $C_1$-$C_6$-alkoxy, $C_1$-$C_6$-alkoxycarbonyl, or hydroxycarbonyl, and wherein $C_6$-$C_{10}$-aryl can be further substituted by up to three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl, and hydroxycarbonyl; N-(heterocyclyl)aminocarbonyl, wherein heterocyclyl can be further substituted by up to three radicals independently selected from the group consisting of $C_1$-$C_6$-alkyl, hydroxy, oxo, $C_1$-$C_6$-alkoxy, $C_1$-$C_6$-alkoxycarbonyl, hydroxycarbonyl, and phenyl-$C_1$-$C_6$-alkyl; a group of the formula —C(=O)—NR$^a$SO$_2$—R$^b$, wherein R$^a$ represents hydrogen or $C_1$-$C_6$-alkyl, and R$^b$ represents $C_1$-$C_6$-alkyl, which can be substituted by trifluoromethyl, or R$^b$ represents $C_6$-$C_{10}$-aryl, which can be substituted by $C_1$-$C_6$-alkyl, halogen, cyano, nitro, or trifluoromethyl; or a group of the formula —P(=O)(OR$^c$)$_2$, wherein R$^c$ represents hydrogen or $C_1$-$C_6$-alkyl;

R$^5$ represents $C_1$-$C_4$-alkyl, which can be substituted with one to three identical or different radicals selected from the group consisting of halogen, hydroxy, $C_1$-$C_6$-alkoxy, $C_2$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl, and the radical —O—$C_1$-$C_4$-alkyl-O—$C_1$-$C_4$-alkyl;

R$^6$ represents hydrogen, $C_1$-$C_6$-alkyl, formyl, aminocarbonyl, mono- or di-$C_1$-$C_4$-alkylaminocarbonyl, $C_3$-$C_8$-cycloalkylcarbonyl, $C_1$-$C_6$-alkylcarbonyl, $C_1$-$C_6$-alkoxycarbonyl, N—($C_1$-$C_4$-alkylsulfonyl)-aminocarbonyl, N—($C_1$-$C_4$-alkylsulfonyl)-N—($C_1$-$C_4$-alkyl)-aminocarbonyl-, heteroaryl, heterocyclyl, heteroarylcarbonyl, or hetero-cyclylcarbonyl, wherein $C_1$-$C_6$-alkyl, mono- and di-$C_1$-$C_4$-alkylaminocarbonyl, $C_1$-$C_6$-alkylcarbonyl, $C_1$-$C_6$-alkoxycarbonyl, heteroaryl, and heterocyclyl can be substituted with one to three identical or different radicals selected from the group consisting of aryl, heteroaryl, hydroxy, $C_1$-$C_4$-alkoxy, hydroxycarbonyl, $C_1$-$C_4$-alkoxycarbonyl, aminocarbonyl, mono- and di-$C_1$-$C_4$-alkylaminocarbonyl, amino, mono- and di-$C_1$-$C_4$-alkylamino, $C_1$-$C_4$-alkylcarbonylamino, tri-($C_1$-$C_6$-alkyl)-silyl, cyano, N-(mono- or di-$C_1$-$C_4$-alkylamino-$C_1$-$C_4$-alkyl)-aminocarbonyl, N—($C_1$-$C_4$-alkoxy-$C_1$-$C_4$-alkyl)-aminocarbonyl, and halogen; or R$^6$ represents a moiety of the formula

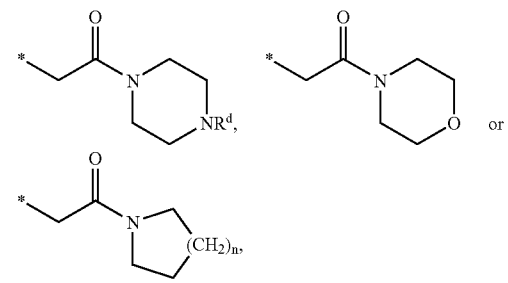

wherein R$^d$ is selected from the group consisting of hydrogen and $C_1$-$C_6$-alkyl, and n represents an integer of 1 or 2; or R$^6$ represents a group of the formula -T-U, wherein T represents a $C_1$-$C_6$-alkanediyl or $C_2$-$C_6$-alkenediyl group, and U represents: $C_6$-$C_{10}$-aryl or 5- or 6-membered heteroaryl, each of which is substituted by one, two, or three radicals independently selected from the group consisting of halogen, $C_1$-$C_6$-alkyl, 5- or 6-membered heteroaryl, and a group of the formula —V—W, wherein V represents a bond or a $C_1$-$C_6$-alkanediyl or $C_2$-$C_6$-alkenediyl group, both of which can be further substituted by $C_3$-$C_8$-cycloalkyl, and W represents $C_1$-$C_6$-alkoxycarbonyl or hydroxycarbonyl; a group of the formula —C(=O)—NR$^e$SO$_2$—R$^f$, wherein R$^e$ represents hydrogen or $C_1$-$C_6$-alkyl, and R$^f$ represents $C_1$-$C_6$-alkyl, which can be substituted by trifluoromethyl, or R$^f$ represents $C_6$-$C_{10}$-aryl, which can be substituted by $C_1$-$C_6$-alkyl, halogen, cyano, nitro, or trifluoromethyl; a group of the formula —C(=O)—NR$^g$R$^h$, wherein R$^g$ represents hydrogen or $C_1$-$C_6$-alkyl, and R$^h$ represents $C_6$-$C_{10}$-aryl, which can be substituted by $C_1$-$C_6$-alkoxycarbonyl or hydroxycarbonyl; a group of the formula —C(=O)—NR$^i$—OR$^k$, wherein R$^i$ and R$^k$ independently from each other represent hydrogen or $C_1$-$C_6$-alkyl; or $C_6$-$C_{10}$-arylalkoxy, which, in the aryl part, can be substituted by halogen, $C_1$-$C_6$-alkyl, $C_1$-$C_6$-alkoxycarbonyl, or hydroxycarbonyl; or R$^6$ represents: $C_3$-$C_8$-cycloalkyl, which can be substituted by up to three radicals independently selected from the group consisting of $C_1$-$C_6$-alkyl, hydroxy, oxo, $C_1$-$C_6$-alkoxycarbonyl, and hydroxycarbonyl; $C_2$-$C_6$-alkenyl, which can be substituted by $C_1$-$C_6$-alkoxycarbonyl or hydroxycarbonyl; $C_1$-$C_6$-alkylcarbonyl, which is substituted by $C_1$-$C_6$-alkoxycarbonylamino; $C_1$-$C_6$-alkoxycarbonyl, which is substituted by phenyl-$C_1$-$C_6$-alkoxycarbonyl, which in the phenyl moiety can be further substituted by halogen, $C_1$-$C_6$-alkyl, $C_1$-$C_6$-alkoxycarbonyl, or hydroxycarbonyl; or a group of the formula —SO$_2$—R$^m$, wherein R$^m$ represents $C_1$-$C_6$-alkyl, which can be substituted by trifluoromethyl, or R$^m$ represents $C_6$-$C_{10}$-aryl, which can be substituted by $C_1$-$C_6$-alkyl, halogen, cyano, nitro, trifluoromethyl, $C_1$-$C_6$-alkoxycarbonyl, or hydroxycarbonyl;

R⁷ represents halogen, nitro, cyano, $C_1$-$C_6$-alkyl, hydroxyl, or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxyl, and $C_1$-$C_4$-alkoxy; and $Y^1$, $Y^2$, $Y^3$, $Y^4$, and $Y^5$ independently from each other represent CH or N, wherein the ring contains either 0, 1, or 2 nitrogen atoms, and salts thereof.

2. The compound of formula (I) according to claim 1, wherein

A represents an aryl or heteroaryl ring;

$R^1$, $R^2$, and $R^3$ independently from each other represent hydrogen, halogen, nitro, cyano, $C_1$-$C_6$-alkyl, hydroxyl, or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxyl, and $C_1$-$C_4$-alkoxy;

$R^4$ represents: $C_1$-$C_6$-alkyl, which can be substituted by up to three radicals independently selected from the group consisting of hydroxyl, $C_1$-$C_6$-alkoxycarbonyl, and hydroxycarbonyl; $C_3$-$C_8$-cycloalkylcarbonyl, which can be substituted by up to three radicals independently selected from the group consisting of $C_1$-$C_6$-alkyl, hydroxy, oxo, $C_1$-$C_6$-alkoxycarbonyl, and hydroxycarbonyl; $C_6$-$C_{10}$-arylcarbonyl, which is substituted by one, two, or three radicals independently selected from the group consisting of halogen, cyano, $C_1$-$C_6$-alkyl, trifluoromethyl, hydroxy, $C_1$-$C_6$-alkoxy, trifluoromethoxy, $C_1$-$C_6$-alkoxycarbonyl, and hydroxycarbonyl; $C_1$-$C_6$-alkoxycarbonyl, which is substituted by one or two radicals independently selected from the group consisting of phenyl-$C_1$-$C_6$-alkoxy, phenyl-$C_1$-$C_6$-alkoxycarbonyl, $C_1$-$C_6$-alkoxy, $C_1$-$C_6$-alkoxycarbonylamino, and 5- or 6-membered heterocyclyl, wherein $C_1$-$C_6$-alkoxy is further substituted by $C_1$-$C_6$-alkoxycarbonyl, or hydroxycarbonyl, and 5- or 6-membered heterocyclyl is further substituted by hydroxy, $C_1$-$C_6$-alkoxycarbonyl, or hydroxycarbonyl; heteroarylcarbonyl, which is substituted by one or two radicals independently selected from the group consisting of hydroxy, amino, halogen, $C_1$-$C_6$-alkoxy, $C_1$-$C_6$-alkoxycarbonyl, and hydroxycarbonyl, and which can additionally be substituted by $C_1$-$C_6$-alkyl; mono- or di-$C_1$-$C_6$-alkylaminocarbonyl, wherein the alkyl moiety or at least one alkyl moiety, respectively, is substituted by $C_6$-$C_{10}$-aryl, which can be further substituted by up to three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl, and hydroxycarbonyl; heterocyclylcarbonyl, which is substituted by one, two, or three radicals independently selected from the group consisting of $C_1$-$C_6$-alkyl, hydroxy, oxo, $C_1$-$C_6$-alkoxy, $C_1$-$C_6$-alkoxycarbonyl, phenyl-$C_1$-$C_6$-alkoxycarbonyl, hydroxycarbonyl, 5- or 6-membered heterocyclyl, 5- or 6-membered heteroaryl, and $C_6$-$C_{10}$-aryl, wherein $C_1$-$C_6$-alkyl is further substituted by hydroxy, $C_1$-$C_6$-alkoxy, $C_1$-$C_6$-alkoxycarbonyl, or hydroxycarbonyl, and wherein $C_6$-$C_{10}$-aryl can be further substituted by up to three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl, and hydroxycarbonyl; or a group of the formula —C(=O)—NH—SO₂—$R^b$, wherein $R^b$ represents $C_1$-$C_6$-alkyl, which can be substituted by trifluoromethyl, or $R^b$ represents $C_6$-$C_{10}$-aryl, which can be substituted by $C_1$-$C_6$-alkyl, halogen, cyano, nitro, or trifluoromethyl;

$R^5$ represents $C_1$-$C_4$-alkyl, which can be substituted with one to three identical or different radicals selected from the group consisting of halogen, hydroxy, $C_1$-$C_6$-alkoxy, $C_2$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl, and the radical —O—$C_1$-$C_4$-alkyl-O—$C_1$-$C_4$-alkyl;

$R^6$ represents hydrogen, $C_1$-$C_6$-alkyl, aminocarbonyl, mono- or di-$C_1$-$C_4$-alkylaminocarbonyl, $C_3$-$C_8$-cycloalkylcarbonyl, $C_1$-$C_6$-alkylcarbonyl, $C_1$-$C_6$-alkoxycarbonyl, N—($C_1$-$C_4$-alkylsulfonyl)-aminocarbonyl, N—($C_1$-$C_4$-alkylsulfonyl)-N—($C_1$-$C_4$-alkyl)-aminocarbonyl-, heteroarylcarbonyl, or heterocyclylcarbonyl, wherein $C_1$-$C_6$-alkyl, mono- and di-$C_1$-$C_4$-alkylaminocarbonyl, $C_1$-$C_6$-alkylcarbonyl, and $C_1$-$C_6$-alkoxycarbonyl can be substituted with one to three identical or different radicals selected from the group consisting of aryl, heteroaryl, hydroxy, $C_1$-$C_4$-alkoxy, hydroxycarbonyl, $C_1$-$C_6$-alkoxycarbonyl, aminocarbonyl, mono- and di-$C_1$-$C_4$-alkylaminocarbonyl, amino, mono- and di-$C_1$-$C_4$-alkylamino, $C_1$-$C_4$-alkylcarbonylamino, N-(mono- or di-$C_1$-$C_4$-alkylamino-$C_1$-$C_4$-alkyl)-aminocarbonyl, N—($C_1$-$C_4$-alkoxy-$C_1$-$C_4$-alkyl)-aminocarbonyl, and halogen; or $R^6$ represents a moiety of the formula

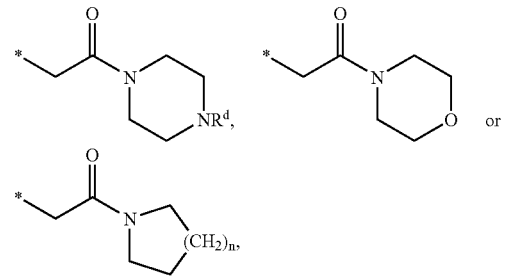

wherein $R^d$ is selected from the group consisting of hydrogen and $C_1$-$C_6$-alkyl, and n represents an integer of 1 or 2; or $R^6$ represents a group of the formula -T-U, wherein T represents a $C_1$-$C_4$-alkanediyl or $C_2$-$C_4$-alkenediyl group, and U represents: $C_6$-$C_{10}$-aryl or 5- or 6-membered heteroaryl, each of which is substituted by one, two, or three radicals independently selected from the group consisting of halogen, $C_1$-$C_6$-alkyl, 5- or 6-membered heteroaryl, and a group of the formula —V—W, wherein V represents a bond, a $C_2$-$C_6$-alkenediyl group, or a $C_1$-$C_6$-alkanediyl group, the latter of which can be further substituted by $C_3$-$C_8$-cycloalkyl, and W represents $C_1$-$C_6$-alkoxycarbonyl or hydroxycarbonyl; a group of the formula —C(=O)—NH—SO₂—$R^f$, wherein $R^f$ represents $C_1$-$C_6$-alkyl, which can be substituted by trifluoromethyl, or $R^f$ represents $C_6$-$C_{10}$-aryl, which can be substituted by $C_1$-$C_6$-alkyl, halogen, cyano, nitro, or trifluoromethyl; or a group of the formula —C(=O)—NHR$^h$, wherein R$^h$ represents $C_6$-$C_{10}$-aryl, which can be substituted by $C_1$-$C_6$-alkoxycarbonyl or hydroxycarbonyl; or $R^6$ represents: $C_3$-$C_8$-cycloalkyl, which can be substituted by up to three radicals independently selected from the group consisting of $C_1$-$C_6$-alkyl, hydroxy, oxo, $C_1$-$C_6$- alkoxycarbonyl, and hydroxycarbonyl; or $C_2$-$C_6$-alkenyl, which can be substituted by $C_1$-$C_6$-alkoxycarbonyl or hydroxycarbonyl;

$R^7$ represents halogen, nitro, cyano, $C_1$-$C_6$-alkyl, hydroxyl, or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxyl, and $C_1$-$C_4$-alkoxy; and $Y^1$, $Y^2$, $Y^3$, $Y^4$, and $Y^5$ independently from each other represent CH or N, wherein the ring contains either 0, 1, or 2 nitrogen atoms.

3. The compound of formula (I) according to claim 1, wherein

A represents a phenyl, naphthyl, or pyridyl ring;

$R^1$, $R^2$, and $R^3$ independently from each other represent hydrogen, fluoro, chloro, bromo, nitro, cyano, methyl, ethyl, trifluoromethyl, or trifluoromethoxy;

$R^4$ represents: $C_1$-$C_4$-alkyl, which can be substituted by up to two radicals independently selected from the group consisting of hydroxy, $C_1$-$C_4$-alkoxycarbonyl, and hydroxycarbonyl; $C_3$-$C_6$-cycloalkylcarbonyl, which can be substituted by up to two radicals independently selected from the group consisting of $C_1$-$C_4$-alkyl, hydroxy, oxo, $C_1$-$C_4$-alkoxycarbonyl, and hydroxycarbonyl; benzoyl, which is substituted by one, two, or three radicals independently selected from the group consisting of fluoro, chloro, bromo, cyano, $C_1$-$C_4$-alkyl, trifluoromethyl, hydroxy, $C_1$-$C_4$-alkoxy, trifluoromethoxy, $C_1$-$C_4$-alkoxycarbonyl, and hydroxycarbonyl; $C_1$-$C_4$-alkoxycarbonyl, which is substituted by one or two radicals independently selected from the group consisting of benzyloxy, benzyloxycarbonyl, $C_1$-$C_4$-alkoxy, $C_1$-$C_4$-alkoxycarbonylamino, pyrrolidinyl, piperidinyl, and morpholinyl, wherein $C_1$-$C_4$-alkoxy is further substituted by $C_1$-$C_4$-alkoxycarbonyl or hydroxycarbonyl, and wherein pyrrolidinyl, piperidinyl, and morpholinyl is further substituted by hydroxy, $C_1$-$C_4$-alkoxycarbonyl, or hydroxycarbonyl; furylcarbonyl, thienylcarbonyl, oxazolylcarbonyl, thiazolylcarbonyl, pyridylcarbonyl, or pyrimidinylcarbonyl, each of which is substituted by one or two radicals independently selected from the group consisting of hydroxy, amino, fluoro, chloro, bromo, $C_1$-$C_4$-alkoxy, $C_1$-$C_4$-alkoxycarbonyl, and hydroxycarbonyl, and each of which can additionally be substituted by $C_1$-$C_4$-alkyl; mono- or di-$C_1$-$C_4$-alkylaminocarbonyl, wherein the alkyl moiety or at least one alkyl moiety, respectively, is substituted by phenyl, which can be further substituted by up to three radicals independently selected from the group consisting of fluoro, chloro, bromo, cyano, trifluoromethyl, $C_1$-$C_4$-alkyl, hydroxy, $C_1$-$C_4$-alkoxy, trifluoromethoxy, $C_1$-$C_4$-alkoxycarbonyl, and hydroxycarbonyl; tetrahydrofurylcarbonyl, tetrahydropyranylcarbonyl, piperidinylcarbonyl, piperazinylcarbonyl, or morpholinylcarbonyl, each of which is substituted by one or two radicals independently selected from the group consisting of $C_1$-$C_4$-alkyl, hydroxy, oxo, $C_1$-$C_4$-alkoxy, $C_1$-$C_4$-alkoxycarbonyl, benzyloxycarbonyl, hydroxycarbonyl, piperidinyl, morpholinyl, pyridyl, and phenyl, wherein $C_1$-$C_4$-alkyl is further substituted by hydroxy, $C_1$-$C_4$-alkoxy, $C_1$-$C_4$-alkoxycarbonyl, or hydroxycarbonyl, and wherein phenyl can be further substituted by up to three radicals independently selected from the group consisting of fluoro, chloro, bromo, cyano, trifluoromethyl, $C_1$-$C_4$-alkyl, hydroxy, $C_1$-$C_4$-alkoxy, trifluoromethoxy, $C_1$-$C_4$-alkoxycarbonyl, and hydroxycarbonyl; or a group of the formula —C(=O)—NH—SO$_2$—R$^b$, wherein R$^b$ represents $C_1$-$C_4$-alkyl, which can be substituted by trifluoromethyl, or R$^b$ represents phenyl, which can be substituted by $C_1$-$C_4$-alkyl, fluoro, chloro, bromo, cyano, nitro, or trifluoromethyl;

$R^5$ represents methyl or ethyl;

$R^6$ represents hydrogen, $C_1$-$C_6$-alkyl, mono- or di-$C_1$-$C_4$-alkylaminocarbonyl, $C_1$-$C_6$-alkylcarbonyl, $C_1$-$C_6$-alkoxycarbonyl, or heterocyclylcarbonyl, wherein $C_1$-$C_6$-alkyl and $C_1$-$C_6$-alkoxycarbonyl can be substituted with one to three identical or different radicals selected from the group consisting of hydroxy, $C_1$-$C_4$-alkoxy, hydroxycarbonyl, $C_1$-$C_6$-alkoxycarbonyl, aminocarbonyl, mono- and di-$C_1$-$C_4$-alkylaminocarbonyl, amino, mono- and di-$C_1$-$C_4$-alkylamino; or $R^6$ represents a moiety of the formula

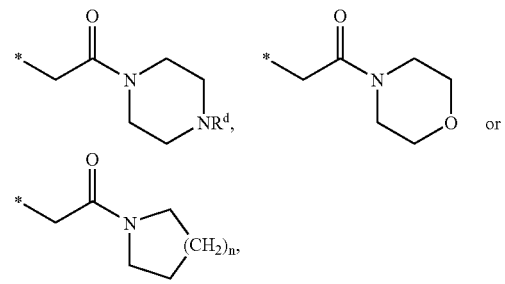

wherein $R^d$ is selected from the group consisting of hydrogen and $C_1$-$C_4$-alkyl, and n represents an integer of 1 or 2; or $R^6$ represents a group of the formula -T-U, wherein T represents a $C_1$-$C_4$-alkanediyl group, and U represents: phenyl, furyl, thienyl, oxazolyl, thiazolyl, or pyridyl, each of which is substituted by one or two radicals independently selected from the group consisting of fluoro, chloro, bromo, $C_1$-$C_4$-alkyl, thienyl, pyridyl, and a group of the formula —V—W, wherein V represents a bond or a $C_1$-$C_4$-alkanediyl or $C_2$-$C_4$-alkenediyl group, and W represents $C_1$-$C_4$-alkoxycarbonyl or hydroxycarbonyl; a group of the formula —C(=O)—NH—SO$_2$—R$^f$, wherein R$^f$ represents $C_1$-$C_4$-alkyl, which can be substituted by trifluoromethyl, or R$^f$ represents phenyl, which can be substituted by $C_1$-$C_4$-alkyl, fluoro, chloro, bromo, cyano, nitro, or trifluoromethyl; or a group of the formula —C(=O)—NHR$^h$, wherein R$^h$ represents phenyl, which can be substituted by $C_1$-$C_4$-alkoxycarbonyl or hydroxycarbonyl, or $R^6$ represents: $C_3$-$C_6$-cycloalkyl, which can be substituted by up to two radicals independently selected from the group consisting of $C_1$-$C_4$-alkyl, hydroxy, oxo, $C_1$-$C_4$-alkoxycarbonyl, and hydroxycarbonyl; or $C_2$-$C_4$-alkenyl, which is substituted by $C_1$-$C_4$-alkoxycarbonyl or hydroxycarbonyl;

$R^7$ represents halogen, nitro, cyano, trifluoromethyl, trifluoromethoxy, methyl, or ethyl; and $Y^1$, $Y^2$, $Y^3$, $Y^4$, and $Y^5$ each represent CH.

4. The compound of formula (I) according to claim 1, wherein

A represents a phenyl or a pyridyl ring;

$R^1$ and $R^3$ each represent hydrogen;

$R^2$ represents fluoro, chloro, bromo, nitro, or cyano;

$R^4$ represents: $C_1$-$C_4$-alkyl, which can be substituted by up to two radicals independently selected from the group consisting of hydroxy, $C_1$-$C_4$-alkoxycarbonyl, and hydroxycarbonyl; $C_3$-$C_6$-cycloalkylcarbonyl, which can be substituted by up to two radicals independently selected from the group consisting of $C_1$-$C_4$-alkyl, hydroxy, oxo, $C_1$-$C_4$-alkoxycarbonyl, and hydroxycarbonyl; benzoyl, which is substituted by one, two, or three radicals independently selected from the group consisting of fluoro, chloro, bromo, cyano, $C_1$-$C_4$-alkyl, trifluoromethyl, hydroxy, $C_1$-$C_4$-alkoxy, trifluoromethoxy, $C_1$-$C_4$-alkoxycarbonyl, and hydroxycarbonyl; $C_1$-$C_4$-alkoxycarbonyl, which is substituted by one or two radicals independently selected from the group consisting of benzyloxy, benzyloxycarbonyl, $C_1$-$C_4$-alkoxy, $C_1$-$C_4$-alkoxycarbonylamino, pyrrolidinyl, piperidinyl, and morpholinyl, wherein $C_1$-$C_4$-alkoxy is further substituted by $C_1$-$C_1$-alkoxycarbonyl or hydroxycarbonyl, and wherein pyrrolidinyl, piperidinyl, and morpholinyl is further substituted by hydroxy, $C_1$-$C_4$-alkoxycarbonyl, or hydroxycarbonyl; furylcarbonyl, oxazolylcarbonyl, thiazolylcarbonyl, or pyridylcarbonyl, each of which is substituted by one or two radicals independently selected from the group consisting of hydroxy, amino, fluoro, chloro, bromo, $C_1$-$C_4$-alkoxy, $C_1$-$C_4$-alkoxycarbonyl, and hydroxycarbonyl, and each of which can additionally be substituted by $C_1$-$C_4$-alkyl; mono- or di-$C_1$-$C_4$-alkylaminocarbonyl, wherein the alkyl moiety or at least one alkyl moiety, respectively, is substituted by phenyl, which can be further substituted by up to three radicals independently selected from the group consisting of fluoro, chloro, bromo, cyano, trifluoromethyl, hydroxy, $C_1$-$C_4$-alkoxy, trifluoromethoxy, $C_1$-$C_4$-alkoxycarbonyl, and hydroxycarbonyl; piperidinylcarbonyl, piperazinylcarbonyl, or morpholinylcarbonyl, each of which is substituted by one or two radicals independently selected from the group consisting of $C_1$-$C_4$-alkyl, hydroxy, oxo, $C_1$-$C_4$-alkoxy, $C_1$-$C_4$-alkoxycarbonyl, benzyloxycarbonyl, hydroxycarbonyl, piperidinyl, morpholinyl, pyridyl, and phenyl, wherein $C_1$-$C_4$-alkyl is further substituted by hydroxy, $C_1$-$C_4$-alkoxy, $C_1$-$C_4$-alkoxycarbonyl, or hydroxycarbonyl, and wherein phenyl can be further substituted by up to three radicals independently selected from the group consisting of fluoro, chloro, bromo, cyano, trifluoromethyl, $C_1$-$C_4$ alkyl, hydroxy, $C_1$-$C_4$-alkoxy, trifluoromethoxy, $C_1$-$C_4$-alkoxycarbonyl and hydroxycarbonyl; or a group of the formula —C(=O)—NH—SO$_2$—$R^b$, wherein $R^b$ represents $C_1$-$C_4$-alkyl, which can be substituted by trifluoromethyl, or $R^b$ represents phenyl, which can be substituted by $C_1$-$C_4$-alkyl, fluoro, chloro, bromo, cyano, nitro, or trifluoromethyl;

$R^5$ represents methyl;

$R^6$ represents hydrogen, $C_1$-$C_4$-alkyl, mono- or di-$C_1$-$C_4$-alkylaminocarbonyl, $C_1$-$C_4$-alkylcarbonyl, or $C_1$-$C_4$-alkoxycarbonyl, wherein $C_1$-$C_4$-alkyl and $C_1$-$C_4$-alkoxycarbonyl can be substituted with a radical selected from the group consisting of hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, amino, mono- and di-$C_1$-$C_4$-alkylamino; or $R^6$ represents a moiety of the formula

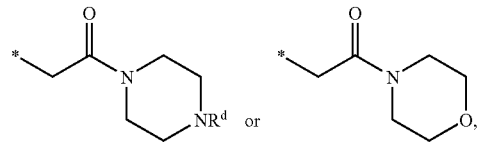

wherein $R^d$ is selected from the group consisting of hydrogen and methyl; or $R^6$ represents a group of the formula -T-U, wherein T represents a —CH$_2$— group, and U represents: phenyl, furyl, or oxazolyl, each of which is substituted by one or two radicals independently selected from the group consisting of fluoro, chloro, bromo, $C_1$-$C_4$-alkyl, and a group of the formula —V—W, wherein V represents a bond, a —CH$_2$— group, or a —CH=CH— group, and W represents $C_1$-$C_4$-alkoxycarbonyl or hydroxycarbonyl; a group of the formula —C(=O)—NH—SO$_2$—$R^f$, wherein $R^f$ represents $C_1$-$C_4$-alkyl, which can be substituted by trifluoromethyl, or $R^f$ represents phenyl, which can be substituted by $C_1$-$C_4$-alkyl, fluoro, chloro, bromo, cyano, nitro, or trifluoromethyl; or a group of the formula —C(=O)—NHR$^h$, wherein $R^h$ represents phenyl, which can be substituted by $C_1$-$C_4$-alkoxycarbonyl or hydroxycarbonyl; or $R^6$ represents: $C_3$-$C_6$-cycloalkyl, which can be substituted by $C_1$-$C_4$-alkoxycarbonyl or hydroxycarbonyl; or a —CH=CH— group, which is substituted by $C_1$-$C_4$-alkoxycarbonyl or hydroxycarbonyl;

$R^7$ represents trifluoromethyl or nitro; and $Y^1$, $Y^2$, $Y^3$, $Y^4$, and $Y^5$ each represent CH.

5. The compound of formula (I) according to any of the preceding claims, wherein A is phenyl or pyridyl.

6. The compound of formula (I) according to any of the preceding claims, wherein $R^1$ is hydrogen.

7. The compound of formula (I) according to any of the preceding claims, wherein $R^2$ is cyano.

8. The compound of formula (I) according to any of the preceding claims, wherein $R^3$ is hydrogen.

9. The compound of formula (I) according to any of the preceding claims, wherein $R^5$ is methyl.

10. The compound of formula (I) according to any of the preceding claims, wherein $R^7$ is trifluoromethyl or nitro.

11. A compound of formula (IA)

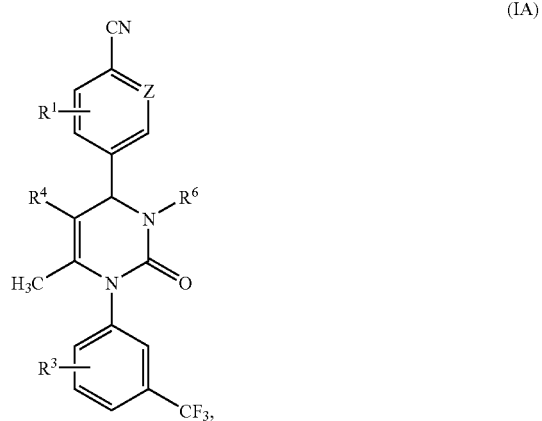

wherein

Z represents CH or N;

$R^1$ and $R^3$ independently from each other represent hydrogen, halogen, nitro, cyano, $C_1$-$C_6$-alkyl, hydroxy, or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxyl, and $C_1$-$C_4$-alkoxy;

$R^4$ represents: $C_1$-$C_6$-alkyl, which can be substituted by up to three radicals independently selected from the group consisting of hydroxy, $C_1$-$C_6$-alkoxycarbonyl, and hydroxycarbonyl; $C_3$-$C_8$-cycloalkylcarbonyl, which can be substituted by up to three radicals independently selected from the group consisting of $C_1$-$C_6$-alkyl, hydroxy, oxo, $C_1$-$C_6$-alkoxycarbonyl, and hydroxycarbonyl; $C_1$-$C_6$-alkylcarbonyl, which is substituted by phenyl-$C_1$-$C_6$-alkoxy or phenyl-$C_1$-$C_6$-alkoxycarbonyl, which in the phenyl moiety can be substituted by halogen, $C_1$-$C_6$-alkyl, hydroxy, $C_1$-$C_6$-alkoxy, $C_1$-$C_6$-alkoxycarbonyl, or hydroxycarbonyl; $C_6$-$C_{10}$-arylcarbonyl, which is substituted by one, two, or three radicals independently selected from the group consisting of halogen, cyano, nitro, $C_1$-$C_6$-alkyl, trifluoromethyl, hydroxy, $C_1$-$C_6$-alkoxy, trifluoromethoxy, amino, $C_1$-$C_6$-alkoxycarbonyl, hydroxycarbonyl, and phenyl; $C_1$-$C_6$-alkoxycarbonyl, which is substituted by one or two radicals independently selected from the group consisting of phenyl-$C_1$-$C_6$-alkoxy, phenyl-$C_1$-$C_6$-alkoxycarbonyl, $C_1$-$C_6$-alkoxy, $C_1$-$C_6$-alkoxycarbonylamino, and 5- or 6-membered heterocyclyl, wherein $C_1$-$C_6$-alkoxy is further substituted by $C_1$-$C_6$-alkoxycarbonyl, or hydroxycarbonyl, and 5- or 6-membered heterocyclyl is further substituted by hydroxy, $C_1$-$C_6$-alkoxycarbonyl, or hydroxycarbonyl; heterocyclylcarbonyl, which is substituted by one or two radicals independently selected from the group consisting of hydroxy, amino, halogen, $C_1$-$C_6$-alkoxy, $C_1$-$C_6$-alkoxycarbonyl, and hydroxycarbonyl, and which can additionally be substituted by $C_1$-$C_6$-alkyl; mono- or di-$C_1$-$C_6$-alkylaminocarbonyl, wherein the alkyl moiety or at least one alkyl moiety, respectively, is substituted by $C_6$-$C_{10}$-aryl, which can be further substituted by up to three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl, and hydroxycarbonyl; $C_6$-$C_{10}$-arylaminocarbonyl or N—($C_1$-$C_6$-alkyl)-N—($C_6$-$C_{10}$-aryl)aminocarbonyl, wherein aryl is substituted by one, two, or three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl, and hydroxycarbonyl, and wherein alkyl, when present, can be substituted by up to three radicals independently selected from the group consisting of hydroxy, $C_1$-$C_6$-alkoxy, $C_1$-$C_6$-alkoxycarbonyl, and hydroxycarbonyl; $C_3$-$C_8$-cycloalkylaminocarbonyl or N—($C_1$-$C_6$-alkyl)-N—($C_3$-$C_8$-cycloalkyl)aminocarbonyl, wherein cycloalkyl can be substituted by up to three radicals independently selected from the group consisting of $C_1$-$C_6$-alkyl, hydroxy, oxo, $C_1$-$C_6$-alkoxycarbonyl, and hydroxycarbonyl, and wherein alkyl, when present, can be substituted by up to three radicals independently selected from the group consisting of hydroxy, $C_1$-$C_6$-alkoxy, $C_1$-$C_6$-alkoxycarbonyl, and hydroxycarbonyl; heterocyclylcarbonyl, which is substituted by one, two, or three radicals independently selected from the group consisting of $C_1$-$C_6$-alkyl, hydroxy, oxo, $C_1$-$C_6$-alkoxy, $C_1$-$C_6$-alkoxycarbonyl, phenyl-$C_1$-$C_6$-alkoxycarbonyl, hydroxycarbonyl, 5- or 6-membered heterocyclyl, 5- or 6-membered heteroaryl, and $C_6$-$C_{10}$-aryl, wherein $C_1$-$C_6$-alkyl is further substituted by hydroxy, $C_1$-$C_6$-alkoxy, $C_1$-$C_6$-alkoxycarbonyl, or hydroxycarbonyl, and wherein $C_6$-$C_{10}$-aryl can be further substituted by up to three radicals independently selected from the group consisting of halogen, cyano, trifluoromethyl, $C_1$-$C_6$-alkyl, hydroxy, $C_1$-$C_6$-alkoxy, trifluoromethoxy, $C_1$-$C_6$-alkoxycarbonyl, and hydroxycarbonyl; N-(heterocyclyl)aminocarbonyl, wherein heterocyclyl can be further substituted by up to three radicals independently selected from the group consisting of $C_1$-$C_6$-alkyl, hydroxy, oxo, $C_1$-$C_6$-alkoxy, $C_1$-$C_6$-alkoxycarbonyl, hydroxycarbonyl, and phenyl-$C_1$-$C_6$-alkyl; a group of the formula —C(=O)—NR$^a$—SO$_2$R$^b$, wherein R$^a$ represents hydrogen or $C_1$-$C_6$-alkyl, and R$^b$ represents $C_1$-$C_6$-alkyl, which can be substituted by trifluoromethyl, or R$^b$ represents $C_6$-$C_{10}$-aryl, which can be substituted by $C_1$-$C_6$-alkyl, halogen, cyano, nitro, or trifluoromethyl; or a group of the formula —P(=O)(OR$^c$)$_2$, wherein R$^c$ represents hydrogen or $C_1$-$C_6$-alkyl; and $R^6$ represents hydrogen, $C_1$-$C_6$-alkyl, formyl, aminocarbonyl, mono- or di-$C_1$-$C_4$-alkylaminocarbonyl, $C_3$-$C_8$-cycloalkylcarbonyl, $C_1$-$C_6$-alkylcarbonyl, $C_1$-$C_6$-alkoxycarbonyl, N—($C_1$-$C_4$-alkylsulfonyl)-aminocarbonyl, N—($C_1$-$C_4$-alkylsulfonyl)-N—($C_1$-$C_4$-alkyl)-aminocarbonyl-, heteroaryl, heterocyclyl, heteroarylcarbonyl, or hetero-cyclylcarbonyl, wherein $C_1$-$C_6$-alkyl, mono- and di-$C_1$-$C_4$-alkylaminocarbonyl, $C_1$-$C_6$-alkylcarbonyl, $C_1$-$C_6$-alkoxycarbonyl, heteroaryl, and heterocyclyl can be substituted with one to three identical or different radicals selected from the group consisting of aryl, heteroaryl, hydroxy, $C_1$-$C_4$-alkoxy, hydroxycarbonyl, $C_1$-$C_6$-alkoxycarbonyl, aminocarbonyl, mono- and di-$C_1$-$C_4$-alkylaminocarbonyl, amino, mono- and di-$C_1$-$C_4$-alkylamino, $C_1$-$C_4$-alkylcarbonylamino, cyano, N-(mono- or di-$C_1$-$C_4$-alkylamino-$C_1$-$C_4$-alkyl)-aminocarbonyl, N—($C_1$-$C_4$-alkoxy-$C_1$-$C_4$-alkyl)-aminocarbonyl, and halogen; or $R^6$ represents a moiety of the formula

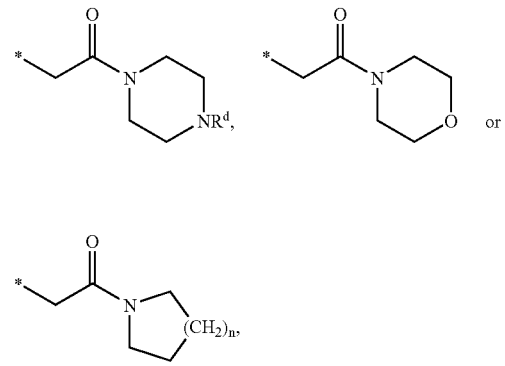

wherein R$^d$ is selected from the group consisting of hydrogen and $C_1$-$C_6$-alkyl, and n represents an integer of 1 or 2; or $R^6$ represents a group of the formula -T-U, wherein T represents a $C_1$-$C_6$-alkanediyl or $C_2$-$C_6$-alkenediyl group, and U represents: $C_6$-$C_{10}$-aryl or 5- or 6-membered heteroaryl, each of which is substituted by one, two, or three radicals independently selected from the group consisting of halogen, $C_1$-$C_6$-alkyl, 5- or 6-membered heteroaryl, and a group of the formula —V—W, wherein V represents a bond or a $C_1$-$C_6$-alkanediyl or $C_2$-$C_6$-alkenediyl group, both of which can be further substituted by $C_3$-$C_8$-cycloalkyl, and W represents $C_1$-$C_6$-alkoxycarbonyl or hydroxycarbonyl; a group of the formula —C(=O)—NR$^e$—SO$_2$—R$^f$, wherein R$^e$ represents hydrogen or $C_1$-$C_6$-alkyl, and R$^f$ represents $C_1$-$C_6$-alkyl, which can be substituted by trifluoromethyl, or R$^f$ represents $C_6$-$C_{10}$-aryl, which can be substituted by $C_1$-$C_6$-alkyl, halogen, cyano, nitro, or trifluoromethyl; a group of the formula —C(=O)—NR$^g$R$^h$, wherein R$^g$ represents hydrogen or $C_1$-$C_6$-alkyl, and R$^h$ represents $C_6$-$C_{10}$-aryl, which can be substituted by $C_1$-$C_6$-alkoxycarbonyl or hydroxycarbonyl; a group of the formula —C(=O)—NR$^i$OR$^k$, wherein R$^i$ and R$^k$ independently from each other represent hydrogen or $C_1$-$C_6$-alkyl; or $C_6$-$C_{10}$-arylalkoxy, which, in the aryl part, can be substituted by halogen, $C_1$-$C_6$-alkyl, $C_1$-$C_6$-alkoxycarbonyl, or hydroxycarbonyl; or R$^6$ represents: $C_3$-$C_8$-cycloalkyl, which can be substituted by up to three radicals independently selected from the group consisting of $C_1$-$C_6$-alkyl, hydroxy, oxo, $C_1$-$C_6$-alkoxycarbonyl, and hydroxycarbonyl; $C_2$-$C_6$-alkenyl, which can be substituted by $C_1$-$C_6$-alkoxycarbonyl or hydroxycarbonyl; $C_1$-$C_6$-alkylcarbonyl, which is substituted by $C_1$-$C_6$-alkoxycarbonylamino; $C_1$-$C_6$-alkoxycarbonyl, which is substituted by phenyl-$C_1$-$C_6$-alkoxycarbonyl, which in the phenyl moiety can be further substituted by halogen, $C_1$-$C_6$-alkyl, $C_1$-$C_6$-alkoxycarbonyl, or hydroxycarbonyl; or a group of the formula —SO$_2$—R$^m$ wherein R$^m$ represents $C_1$-$C_6$-alkyl, which can be substituted by trifluoromethyl, or R$^m$ represents $C_6$-$C_{10}$-aryl, which can be substituted by $C_1$-$C_6$-alkyl, halogen, cyano, nitro, trifluoromethyl, $C_1$-$C_6$-alkoxycarbonyl, or hydroxycarbonyl.

12. Process for synthesizing a compound of formula (I) according to claim 1 by condensing a compound of general formula (II)

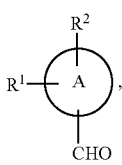
(II)

wherein A, R$^1$, and R$^2$ have the meaning indicated in claim 1, with a compound of formula (III)

(III)

wherein R$^4$ and R$^5$ have the meaning indicated in claim 1, and a compound of formula (IV)

(IV)

wherein R$^3$, R$^7$, and Y$^1$ to Y$^5$ have the meaning indicated in claim 1, in the presence of an acid or acid anhydride to give a compound of the formula (IB)

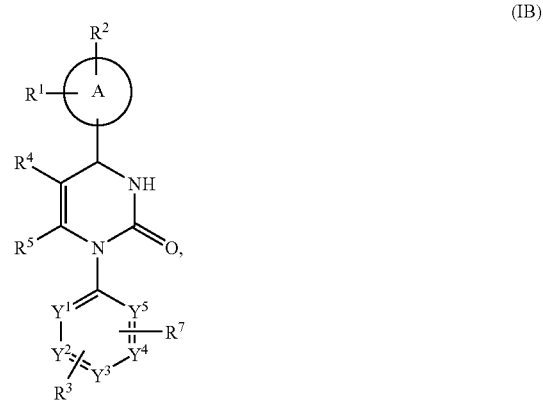
(IB)

wherein A, R$^1$ to R$^5$, R$^7$, and Y$^1$ to Y$^5$ have the meaning indicated in claim 1, optionally followed, in case R$^6$ does not represent hydrogen, by reaction of the compound of general formula (IB) with a compound of formula (V)

R$^{6*}$—X  (V), wherein R$^{6*}$ has the meaning of R$^6$ as indicated in claim 1, but does not represent hydrogen, and X represents a leaving group, in the presence of a base.

13. A composition comprising a compound of formula (I) according to claim 1 and a pharmacologically acceptable excipient.

14. A method for treating chronic obstructive pulmonary disease, acute coronary syndrome, acute myocardial infarction or heart failure in humans and animals comprising the step of administering a therapeutically effective amount of at least one compound of formula (I) according to claim 1.

15. A composition comprising a compound of formula (I) according to claim 2 and a pharmacologically acceptable excipient.

16. A composition comprising a compound of formula (I) according to claim 3 and a pharmacologically acceptable excipient.

17. A composition comprising a compound of formula (I) according to claim 4 and a pharmacologically acceptable excipient.

18. A method for treating chronic obstructive pulmonary disease, acute coronary syndrome, acute myocardial infarction or heart failure in humans and animals comprising the step of administering a therapeutically effective amount of at least one compound of formula (I) according to claim 2.

19. A method for treating chronic obstructive pulmonary disease, acute coronary syndrome, acute myocardial infarction or heart failure in humans and animals comprising the step of administering a therapeutically effective amount of at least one compound of formula (I) according to claim 3.

20. A method for treating chronic obstructive pulmonary disease, acute coronary syndrome, acute myocardial infarction or heart failure in humans and animals comprising the step of administering a therapeutically effective amount of at least one compound of formula (I) according to claim 4.

* * * * *